(12) United States Patent
Suto et al.

(10) Patent No.: US 8,278,120 B2
(45) Date of Patent: *Oct. 2, 2012

(54) METHOD OF CHANGING FLUORESCENCE WAVELENGTH OF FLUORESCENT PROTEIN

(75) Inventors: Kyoko Suto, Tokyo (JP); Hiromi Takenaka, Tokyo (JP); Yasuhiro Takenaka, Tsukuba (JP)

(73) Assignee: NEC Soft, Ltd., Tokyo (JP)

( * ) Notice: Subject to any disclaimer, the term of this patent is extended or adjusted under 35 U.S.C. 154(b) by 689 days.

This patent is subject to a terminal disclaimer.

(21) Appl. No.: 12/162,460

(22) PCT Filed: Jan. 25, 2007

(86) PCT No.: PCT/JP2007/051188
§ 371 (c)(1),
(2), (4) Date: Jul. 28, 2008

(87) PCT Pub. No.: WO2007/086473
PCT Pub. Date: Aug. 2, 2007

(65) Prior Publication Data
US 2009/0318673 A1    Dec. 24, 2009

(30) Foreign Application Priority Data

Jan. 26, 2006 (JP) .................................. 2006-018236

(51) Int. Cl.
G01N 33/536 (2006.01)
G01N 33/533 (2006.01)
C07K 1/00 (2006.01)
C07K 14/00 (2006.01)
C07K 17/00 (2006.01)

(52) U.S. Cl. ........ 436/546; 436/544; 530/350; 530/401; 530/402; 532/26.6

(58) Field of Classification Search .................. None
See application file for complete search history.

(56) References Cited

U.S. PATENT DOCUMENTS 6,593,135 B2 * 7/2003 Wachter et al. ............... 435/325
(Continued)

FOREIGN PATENT DOCUMENTS

EP    1734117 A1    12/2006
(Continued)

OTHER PUBLICATIONS

Masuda et al., (Gene. 2006. vol. 372.18-25).*
(Continued)

*Primary Examiner* — Ja'na Hines
(74) *Attorney, Agent, or Firm* — Sughrue Mion, PLLC

(57) ABSTRACT

The present invention provides: a method of changing the fluorescence wavelength of a GFP-like fluorescent protein from copepod while maintaining recombinant expression efficiency, which comprises identifying a structural factor for determining the fluorescence wavelength thereof in the three-dimensional structure of the protein and modifying amino acid residues associated with the structural factor; and a modified fluorescent protein obtained by applying said method. For example, with regard to a GFP-like fluorescent protein from *Chiridius poppei*, $His^{52}$ in an α helix-like secondary structure: PFLLSHCMGYGFYHF ($α_1$ 47-61) comprising a fluorescent moiety site $\overline{GYG}$ is replaced with an aromatic amino acid selected from Phe, Tyr and Trp, so as to cause a red shift of the fluorescent peak wavelength; or it is replaced with Ala, Val, Ile, Leu, Gly, Cys, Met, Ser, Thr, or Asp, Asn, Glu or Gln, so as to cause a blue shift of the fluorescence peak wavelength.

5 Claims, 9 Drawing Sheets

U.S. PATENT DOCUMENTS

| | | | | |
|---|---|---|---|---|
| 6,780,975 | B2 * | 8/2004 | Tsien et al. | 530/350 |
| 2004/0203013 | A1 * | 10/2004 | Matsui et al. | 435/6 |
| 2005/0221388 | A1 * | 10/2005 | Lu et al. | 435/7.1 |

FOREIGN PATENT DOCUMENTS

| | | | |
|---|---|---|---|
| EP | 2050332 A1 | | 4/2009 |
| WO | 01/90147 A2 | | 11/2001 |
| WO | WO 01/90147 | * | 11/2001 |
| WO | 2004/058973 A1 | | 7/2004 |
| WO | 2005/095599 A1 | | 10/2005 |

OTHER PUBLICATIONS

Afolabi et al., (African J. of Biotechnology. 2005. vol. 4(6):531-540).*

Dopf et al., ("Deletion mapping of the Aequorea Victoria Green Fluorescent Protein" Gene. 1996. vol. 173:39-44).*

Li et al., ("Deletions of the Aequorea Victoria Green Fluorescent Protein Define the Minimal Domain Required for Fluorescence" J. of Biol. Chem. 1997. vol. 272(45):28545-28549).*

Cubitt et al., ("Understanding, Improving and Using Green Fluorescent Proteins" Trends in Biochemical Sciences. 1995. vol. 20(11):448-455).*

Andrew B. Cubitt, et al.; "Understanding, Improving and Using Green Fluorescent Proteins"; Trends in Biochemical Sciences; Nov. 1995; pp. 448-455; vol. 20, No. 11.

Atsushi Miyawaki, et al.; "Mechanisms of Protein Fluorophore Formation and Engineering"; Current Opinion in Chemical Biology; 2003; pp. 557-562; vol. 7, No. 5.

Mikhail V. Matz, et al.; "Fluorescent Proteins from Nonbioluminescent Anthozoa Species"; Nature Biotechnology; Oct. 1999; pp. 969-973; vol. 17, No. 10.

Rajul K. Jain, et al.; "Local Complexity of Amino Acid Interactions in a Protein Core"; Proceeding of the National Academy of Sciences of the United States of America; Jan. 6, 2004; pp. 111-116; vol. 101, No. 1.

Dmitry A. Shagin, et al.; "GFP-like Proteins as Ubiquitous Metazoan Superfamily: Evolution of Functional Features and Structural Complexity", Molecular Biology and Evolution; 2004; pp. 841-850; vol. 21, No. 5.

R.Y. Tsien, "The Green Fluorescent Protein", Annual Review of Biochemistry, vol. 67, pp. 509-544 (1998).

A.B. Cubitt et al. "Understanding Structure-Function Relationships in the Aequorea victoria Green Fluorescent Protein", Methods in Cell Biology, vol. 58, pp. 19-30 (1999).

P.G. Wilmann "The 2.1 Å Crystal Structure of copGFP, a Representative Member of the Copepod Clade Within the Green Fluorescent Protein Superfamily", Journal of Molecular Biology, vol. 359, No. 4, pp. 890-900 (published Jun. 16, 2006).

Kyoto Suto et al. "Structural basis for red-shifted emission of a GFP-like protein from the marine copepod *Chiridius poppei*", Genes to Cells: Devoted to Molecular & Cellular Mechanisms, vol. 14, No. 6, pp. 727-737 (published on Jun. 2009).

International Preliminary Search Report on Patentability from Corresponding Patent Application PCT/JP2007/051188 dated Sep. 18, 2008.

* cited by examiner

Fig. 1

```
Cop-Green  M P A M K I E C R I T G T L N G V E F E L V G G G E G T P E
CpYGFP     M T T F K I E S R I H G N L N G E K F E L V G G G - - V G E
           * . : * * * . * * . * . * * *   * * * * * * *       .   *
                [  β₁ 4-14        ]   [   β₂ 17-28            ]

Cop-Green  Q G R M T N K M K S T K G A L T F S P Y L L S H V M G Y G F
CpYGFP     E G R L E I E M K T K D K P L A F S P F L L S H C M G Y G F
           : * *     : * * . .   . * * * * : * * * *   * * * * *
              [  β₂ 31-39      ]          [   α₁ 47-61

Cop-Green  Y H F G T Y P S G Y E N P F L H A I N N G G Y T N T R I E K
CpYGFP     Y H F A S F P K G T K N I Y L H A A T N G G Y T N T R K E I
           * * * .   : : * . *   : *   : * * *   * * * * * * * *   *
                    ] [β x]         [  α₂ 71-77  ]   [  β₄ 80-89

Cop-Green  Y E D G G V L H V S F S Y R Y E A G R V I G D F K V V G T G
CpYGFP     Y E D G G I L E V N F R Y T Y E F N K I I G D V E C I G H G
           * * * * * : * . * . *   * * *   * *   . : : * * * . :   : * *
             ]      [   β₅ 93-104    ]    [   β₆ 107-117     ]

Cop-Green  F P E D S V I F T D K I I R S N A T V E H L H P M G D N V L
CpYGFP     F P S Q S P I F K D T I V K S C P T V D L M L P M S G N I I
           * * . : *   * * . * . * : * *   . * * :   :   * * . . * : :
                              [    β₇ 132-143      ]      [

Cop-Green  V G S F A R T F S L R D G G Y Y S F V V D S H M H F K S A I
CpYGFP     A S S Y A R A F Q L K D G S F Y T A E V K N N I D F K N P I
           . . * : * * : * . * : * * . : * :     * . . : : . * * . . *
              β₈ 147-158 .    ]     [    β₉ 162-174          ]

Cop-Green  H P S I L Q N G G P M F A F R R V E E L H S N T E L G I V E
CpYGFP     H E S F S K S G - P M F T H R R V E E T H T K E N L A M V E
           *   * : .   . *   * * * : . * * * * *   * : :   : * . : * *
                             [    β₁₀ 188-199    ]     [ β₁₁ 202-212

Cop-Green  Y Q H A F K T P I A F A
CpYGFP     Y Q Q V F N S A P R D M
           * * : . . * : : .
                                ]
```

Fig. 4
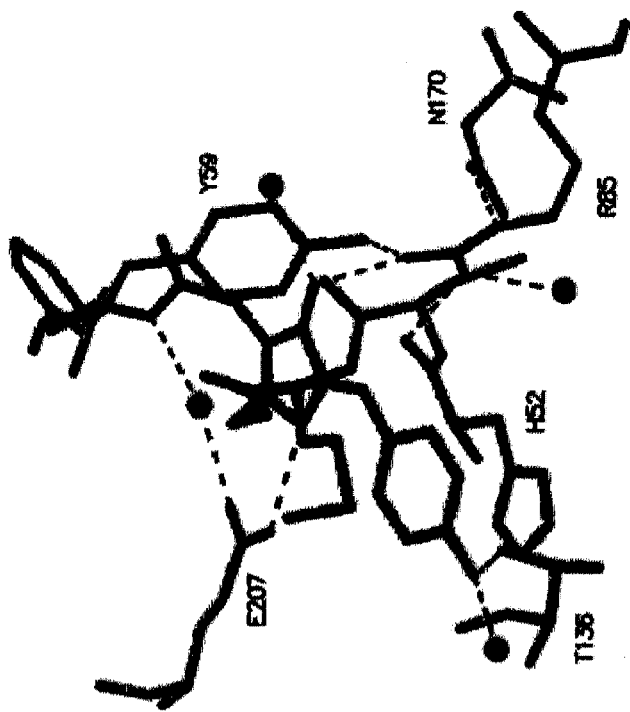
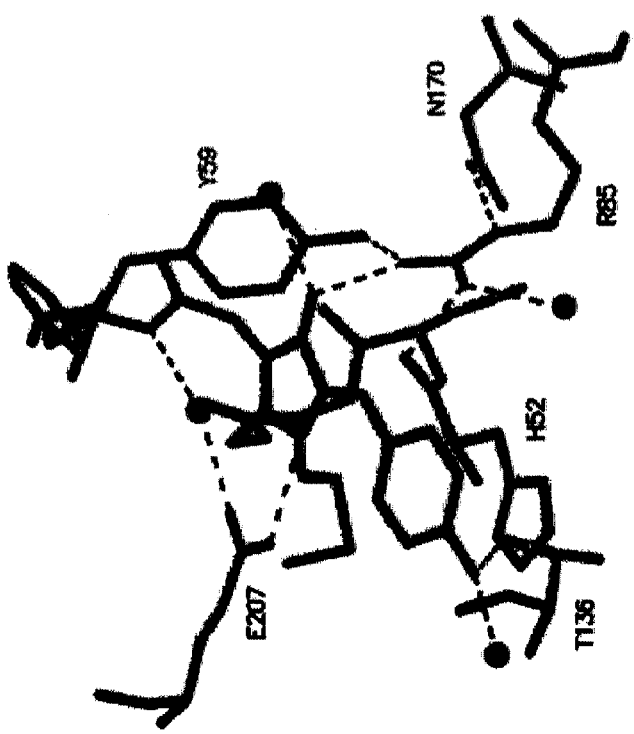

Fig. 5

```
                        10                  20                  30
CpGFP   - - - - - - - - M T T F K I E S R I H G N L N G E K F E L V G G G V G E - E - G
OsRed   M R S S K N V I K E F M R F K V R M E G T V N G H E F E I E G E G E G R P Y E G
aqGFP   M S K G E E L F T G V V P I L V E L D G D V N H K F S V S G E G E G D A T Y G
              [    β₁ 4-14    ]    [   β₂ 17-28    ]

```
CpYGFP native    M T T F K I E S R I H G N L N G E K F E
CpYGFP mutant1   M T T F K I E S R I H G N L N G E K F E
CpYGFP mutant2   M T T F K I E S R I H G N L N G E K F E 30                    40                   50
L V G G G V G E E G R L E I E M K T K D K P L A F S P F L L
L V G G G V G E E G R L E I E M K T K D K P L A F S P F L L
L V G G G V G E E G R L E I E M K T K D K P L A F S P F L L 60                    70                   80
S H C M G Y G F Y H F A S F P K G T K N I Y L H A A T N G G
S H C M G W G F Y H F A S F P K G T K N I Y L H A A T N G G
S H C M G W G F Y H F A S F P K G T K N I Y L H A A T N G G 90                   100                  110
Y T N T R K E I Y E D G G I L E V N F R Y T Y E F N K I I G
Y T N T R K E I Y E D G G I L E V N F R Y T Y E F N K I I G
Y T N T R K E I Y E D G G I L E V N F R Y T Y E F N K I I G 120                   130                  140
D V E C I G H G F P S Q S P I F K D T I V K S C P T V D L M
D V E C I G H G F P S Q S P I F K D T I V K S C P T V D L M
D V E C I G H G F P S Q S P I F K D T I V K S C P A V D L M 150                   160                  170
L P M S G N I I A S S Y A R A F Q L K D G S F Y T A E V K N
L P M S G N I I A S S Y A R A F Q L K D G S F Y T A E V K N
L P M S G N I I A S S Y A R A F Q L K D G S F Y T A E V K N 180                   190                  200
N I D F K N P I H E S F S K S G P M F T H R R V E E T H T K
N I D F K N P I H E S F S K S G P M F T H R R S E E T H T K
N I D F K N P I H E S F S K S G P M F T H R R S E E T H T K 210                   220
E N L A M V E Y Q Q V F N S A P R D M *
E N L A M V E Y Q Q V F N S A P R D M *   (murant1: Y56W, V194S)
E N L A M V E Y Q Q V F N S A P R D M *   (mutant2: Y56W, V194S, T136A)
```

Excitation (fluorescence 458 nm) Fluorescence (excitation 400 nm)

Excitation (fluorescence 458 nm) Fluorescence (excitation 400 nm)

METHOD OF CHANGING FLUORESCENCE WAVELENGTH OF FLUORESCENT PROTEIN

TECHNICAL FIELD

The present invention relates to a method of changing a fluorescence wavelength of a GFP-like fluorescent protein and a modified fluorescent protein obtained by applying said method. The present invention particularly relates to a method of changing the fluorescence wavelength of a GFP-like fluorescent protein, ppluGFP2, from *Pontellina plumata*, or the fluorescence wavelength of a fluorescent protein, CpYGFP, from *Chiridius poppei* that is Copepoda belonging to Aetideidae, and a modified fluorescent protein obtained by applying said method.

BACKGROUND ART

A green fluorescent protein (GFP) from a jellyfish, *Aequorea victoria*, or a modified protein thereof, is capable of recombinant expression in heterologous cells, and in particular, in various types of mammalian cells. Moreover, the obtained recombinant protein exhibits fluorescent properties in host cells. With use of such features, the GFP from *A. victoria* and a homologue thereof have been used as in vivo fluorescent marker proteins capable of expressing in animal cells for various types of targets or intended uses in the fields of biochemistry, cell physiology, and medicine (See Reference 1: Lippincott-Schwartz, J., G. H. Patterson, Science, Vol. 300, 87-91 (2003); Reference 2: Tsien, R. Y., Annu. Rev. Biochem. Vol. 67, 509-544 (1998)).

With regard to the GFP from *A. victoria*, a mechanism required for exhibiting the fluorescent properties thereof has been studied. First, it has been revealed that in the process of the folding of the translated polypeptide of the GFP into its natural steric structure, it folds in the form of mature GFP having fluorescent properties through the steps of cyclization of its internal tripeptide site, from which the fluorescent moiety is constructed, and the subsequent oxidation thereof. Moreover, it has also been confirmed that SYG at the positions 65-67 in the deduced amino acid sequence of wild-type GFP from *A. victoria* is such an internal tripeptide site, from which the fluorescent moiety is formed. With regard to the wild-type GFP from *A. victoria*, the result of X-ray crystal structure analysis thereof has been published. In the three-dimensional structure thereof, 11 β strands constitute a barrel form, and one α helix is positioned in the center portion of the barrel form so as to pass through from the upper portion to the lower portion thereof. This form as a whole is referred to as can "β". The SYG at the positions 65-67 exists in the α helix, and the fluorescent moiety formed therefrom is located almost in the center of the "β can", so that it can be maintained in a hydrophobic environment isolated from the surrounding solvent molecules (water molecules) (See Reference 3: Ormo, M. et al., Science Vol. 273, 1392-1395 (1996); Reference 4: Yang, F. et al., Nature Biotech., Vol. 14, 1246-1251 (1996)).

It is assumed that a mechanism of conversion of the peptide into mature GFP, post to the translation, namely, such formation of a p-hydroxybenzolideneimidazolinone structure of the fluorescent moiety from the SYG existing in the α helix is carried out through the following process.

Folding post to translation (transition to distorted configuration)

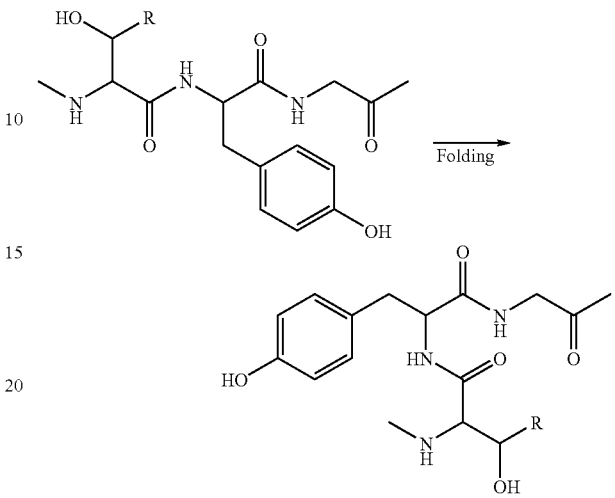

[Chemcial formula 1]

Cyclization and dehydration steps

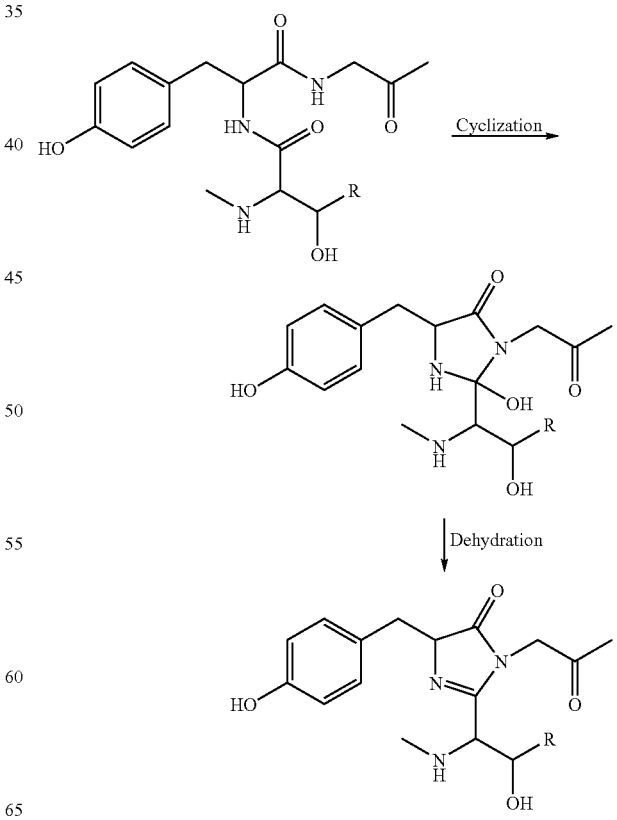

[Chemical formula 2]

Oxidation step: completion of p-hydroxybenzylideneimidazolinone structure

[Chemical formula 3]

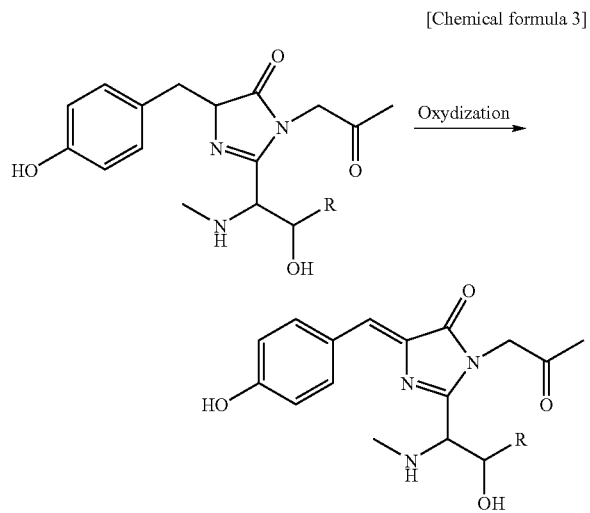

Finally, the fluorescent moiety, p-hydroxybenzylideneimidazolinone structure, is in a state of equilibrium between the following neutral form and ionized form.

Equilibrium between the ionized form and neutral form in p-hydroxybenzylideneimidazolinone structure "idene" structure. If such a structure as a whole has a plane configuration, a π-electron conjugated system is expanded, and the energy difference between the lowest electronically excited state and the ground state is decreased. Specifically, since hyperconjugation of the aforementioned tautomeric form is present in the ionized form structure, the whole structure has a plane configuration. On the other hand, in the neutral form structure, if the 6-membered ring of "p-hydroxybenzyl" is slightly tilted from a plane on which the "idene" structure and the 5-membered ring of "imidazolinone" lie, the π-electron conjugated systems of both portions are divided, and light absorption is mainly observed from the ground state localized in the 6-membered ring of "p-hydroxybenzyl".

Moreover, many attempts to modify the amino acid sequence of the wild-type GFP from *A. victoria* to change the fluorescence wavelength have been reported. Specifically, a way for introducing a mutation that influences on a π-electron conjugated system acting as the fluorescent moiety into the amino acid sequence, so that the resulted fluorescence is blue-shifted from the original green color to a blue or blue green color, or so that the resulted fluorescence is red-shifted to a yellow color, has been reported.

In the case of S65T-GFP formed by replacing Ser at position 65 with Thr in SYG at positions 65-67 that constitutes the fluorescent moiety, when TYG forms a fluorescent moiety in the same manner, the state of equilibrium between the neutral form and the ionized form is inclined to the ionized form. As a result, in S65T-GFP, a peak at 489 to 490 nm of the maximum absorption wavelength corresponding to absorption of

[Chemical formula 4]

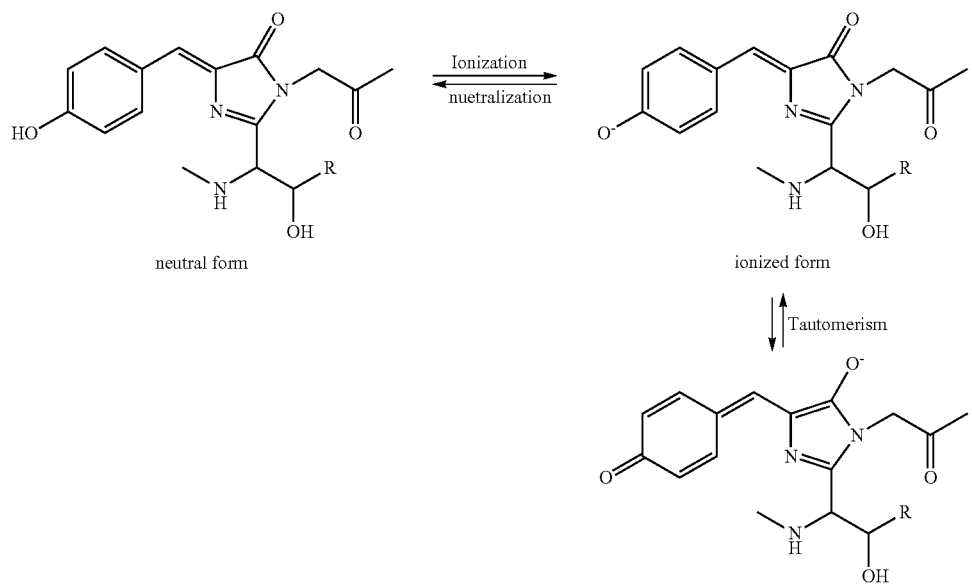

Accordingly, with regard to the wild-type GFP from *A. victoria*, a peak at 395 to 397 nm of the maximum absorption wavelength corresponding to absorption of the neutral form and a peak at 470 to 475 nm of the maximum absorption wavelength corresponding to absorption of the ionized form are observed on an excitation spectrum. On the other hand, on a fluorescence spectrum, a peak at 504 nm of the maximum fluorescence wavelength corresponding to the fluorescence of the ionized form is observed. The 6-membered ring of "p-hydroxybenzyl" contained in the fluorescent moiety is coupled with the 5-membered ring of "imidazolinone" via an the ionized form is mainly observed on an excitation spectrum. In addition, on a fluorescence spectrum, a peak at 510 to 511 nm of the maximum fluorescence wavelength corresponding to the fluorescence of an ionized form is measured, and thus it is somewhat red-shifted, when compared with the fluorescence of the wild-type GFP.

Even if a mutation is not introduced into SYG at positions 65-67 constituting a fluorescent moiety, when the folding into a natural steric structure is conducted as a means for promoting ionization of the phenolic hydroxyl group of Tyr, a method of introducing a mutation by replacing Glu at position 222 existing in two β strands ($\beta_{10}$, $\beta_{11}$) on the C-terminal side existing around the p-hydroxybenzylideneimidazolinone structure as a fluorescent moiety with Gly has been reported, for example. That is to say, if a carboxyl group on the side chain of Glu at position 222 that functions as a proton donator is eliminated, the phenolic hydroxyl group of Tyr makes up for such an eliminated carboxyl group. As a result, ionization of the phenolic hydroxyl group of Tyr is promoted.

Although the "idene" structure and the 5-membered ring portion of "imidazolinone" included in the p-hydroxybenzylideneimidazolinone structure that constitutes the aforementioned fluorescent moiety of GFP are basically employed in the same manner, an attempt to replace a p-hydroxyphanyl group (phenol ring) from the side chain of Tyr at position 66 with a imidazole ring derived from His or a indole ring derived from Trp, so as to change the fluorescence wavelength of the wild-type GFP, has also been made.

In the case of Y66H-GFP wherein Tyr at position 66 is replaced with His, for example, it has been reported that its fluorescence is blue-shifted from the green fluorescence of the wild-type GFP and that it exhibits a blue fluorescence at 447 nm of the maximum wavelength. This Y66H-GFP having a fluorescent moiety formed from SHG is also referred to as BFP (Blue Fluorescent Protein). The fluorescent moiety in this BFP has a 1H-imiazol-4-yl-methylideneimidazolinone structure, in which the p-hydroxyphanyl group (phenol ring) derived from Tyr is changed with an imidazole ring derived from His. It is likely that such a 1H-imiazol-4-yl-methylideneimidazolinone structure is in a state of equilibrium between the following ionized form and neutral form.

Equilibrium between the ionized form and neutral form in 1H-imidazol-4-yl-methylideneimidazolinone structure fluorescence is blue-shifted from the green fluorescence of the wild-type GFP, and that it exhibits a blue green fluorescence at 485 nm of the maximum wavelength. This Y66W-GFP having a fluorescent moiety formed from SWG is also referred to as CFP (Cyan Fluorescent Protein). In the fluorescent moiety in this CFP, p-hydroxyphanyl group (phenol ring) derived from Tyr is replaced with an indole ring derived from Trp, and it has an indole-3-yl-methylideneimidazolinone structure.

Indole-3-yl methylideneimidazolinone structure

[Chemical formula 6]

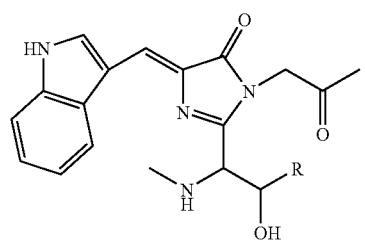

The fluorescence spectrum of the aforementioned CFP shows a form obtained by overlapping two fluorescence peaks having only a small energy difference. Even on the corresponding excitation spectrum, a form obtained by overlapping two peaks having a small energy difference is shown. As a factor for giving such two types of peaks, it has been suggested that two fluorescent states (photoexcited states) coexist and that a certain state of equilibrium exists between the two fluorescent states (photoexcited states).

[Chemical formula 5]

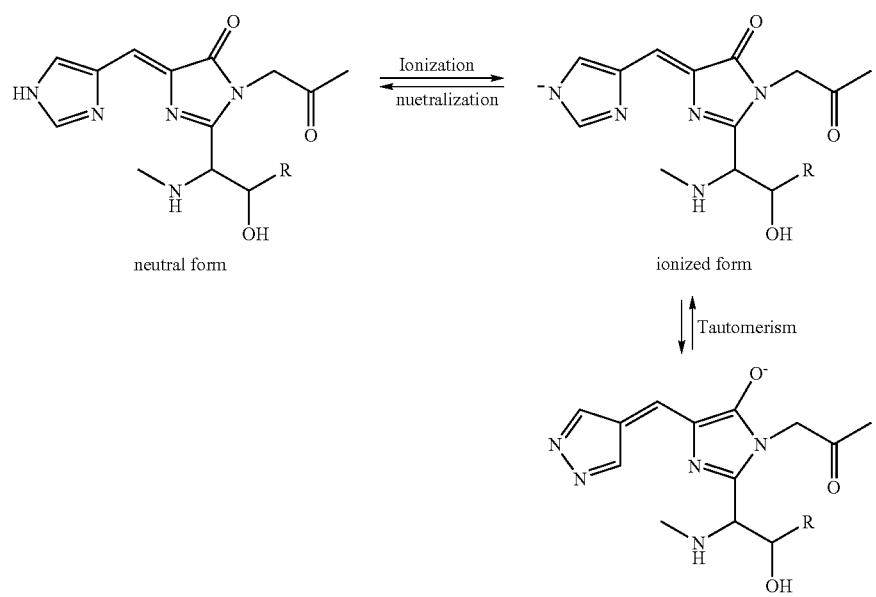

In either case, due to the difference in π-electron conjugated systems, a peak at 383 nm of the maximum absorption wavelength is measured on its excitation spectrum, and a peak at 447 nm of the maximum fluorescence wavelength is measured on its fluorescence spectrum. The two peaks exhibit a blue shift.

On the other hand, in the case of Y66W-GFP wherein Tyr at position 66 is replaced with Trp, it has been reported that its With regard to such BFP and CFP, in addition to the way for changing an aromatic ring group constituting a π-electron conjugated system itself by replacing Tyr at position 66 that forms a fluorescence moiety with another aromatic amino acid residue, a technique for red-shifting a fluorescence wavelength thereof by interaction (π-π-stacking) that is due to the overlapping of the π-electrons of both substances caused by the overlapping of plurality of the aromatic ring groups has also been reported. Specifically, when the folding into a natural steric structure is conducted, if Thr at position 203 existing in a β strand ($β_{10}$) on the C-terminal side existing around the p-hydroxybenzylideneimidazolinone structure as a fluorescent moiety is replaced with an aromatic amino acid residue, an aromatic ring group from said aromatic amino acid residue is overlapped with the π-electron conjugated system of the indole-3-yl-methylideneimidazolinone structure, and in particular, with a p-hydroxyphanyl group (phenol ring) portion derived from Tyr. In the case of a modified form obtained by replacing Thr at position 203 with Tyr, for example, a peak around 516 nm of the maximum absorption wavelength is measured on an excitation spectrum, whereas a peak around 529 nm of the maximum fluorescence wavelength is measured on a fluorescence spectrum. The two peaks exhibit a red shift. A modified protein exhibiting a yellow fluorescence as a result of this type of π-π-stacking is named as YFP (Yellow Fluorescent Protein) (See Reference 5: Cubitt, A. B. et al., Trends Biochem. Sci., Vol. 20, 448-455 (1995)).

Aside from the aforementioned GFP from *A. victoria* and modified proteins thereof, a fluorescent protein from *Discosoma striata* has been known. In the case of this fluorescent protein, a peak around 558 nm of the maximum absorption wavelength is measured on an excitation spectrum, whereas a peak around 583 nm of the maximum fluorescence wavelength is measured on a fluorescence spectrum. That is to say, this is a fluorescent protein exhibiting a red fluorescence, and it is referred to as DsRFP, which indicates a red fluorescent protein from *Discosoma striata*. The fluorescent moiety of this DsRFP is formed from QYG. In the DsRFP, in addition to the p-hydroxybenzylideneimidazolinone structure, a region including the amide bond on the N-terminal side of Glu at position 65 functions as a fluorescent moiety. As a result, the aforementioned great red shift has been achieved (See Reference 6: Matz, M. V. et al., Nature Biotech., Vol. 17, 969-973 (1999); Reference 7: Verkhusha, et al., Nature Biotech., Vol. 22, 289-296 (2004)).

Non-Patent Document 1: Lippincott-Schwartz, J. G. H. Patterson, Science Vol. 300, 87-91 (2003)

Non-Patent Document 2: Tsien, R. Y., Annu. Rev. Biochem. Vol. 67, 509-544 (1998)

Non-Patent Document 3: Ormo, M. et al., Science Vol. 273, 1392-1395 (1996)

Non-Patent Document 4: Yang, F. et al., Nature Biotech., Vol. 14, 1246-1251 (1996)

Non-Patent Document 5: Cubitt, A. B. et al., Trends Biochem. Sci., Vol. 20, 448-455 (1995)

Non-Patent Document 6: Matz, M. V. et al., Nature Biotech., Vol. 17, 969-973 (1999)

Non-Patent Document 7: Verkhusha, et al., Nature Biotech., Vol. 22, 289-296 (2004)

DISCLOSURE OF THE INVENTION

Problems to be Solved by the Invention

Moreover, other than GFP from *A. victoria*, a GFP-like protein has been cloned from class Hydrozoa of Cnidaria. Furthermore, such a GFP-like protein has also been cloned from class Anthozoa of Cnidaria. It has been reported that, from the viewpoint of biological evolution, such a GFP-like protein discovered from class Anthozoa of Cnidaria would constitute a fluorescent protein family having the same origin (please refer to Reference 8: Y. A. Labas et al., Proc. Natl. Acad. Sci. U.S.A., Vol. 99, 4256-4261 (2002)).

In addition, it has been reported that, other than Cnidaria, several types of copepods belonging to Arthropoda phylum, Mandibulata subphylum, Crustacea class, and Copepoda subclass, produce fluorescent proteins emitting a green fluorescence. For example, it has been reported that total 4 types of copepods (Copepoda subclass), namely, *Pontellina plutellina, Labidocera aestiva, Pontella meadi*, and unidentified one type, belonging to Pontellidae (Pontellidae family) classified into Calanoida order, maintain GFP-like fluorescent proteins (See Reference 9: SHAGIN et al., Mol. Biol. Evol., (2004), Vol. 21, No. 5, pp. 841-850). Furthermore, the present inventors have also discovered a GFP-like fluorescent protein (CpYGFP) from *Chiridius poppei* belonging to Aetideidae (Aetideidae family) classified into Calanoida order from among copepods (Copepoda subclass) (Reference 10: International Publication WO 2005/095599 A1, or U.S. Patent Application Publication US 2005/0221338 A1).

Such GFP-like fluorescent proteins from copepods show low homology at the amino acid sequence level with the GFP from *A. victoria*. Thus, it is assumed that a large number of mutations have occurred on the amino acid sequence in the evolutionary process. However, based on a predicted secondary structure, it is predicted that such GFP-like fluorescent proteins from copepods comprise 11 β strands and a single α helix including GYG associated with the structure of a fluorescent moiety, just as with the GFP from *A. victoria* and DsRFP from *Discosoma striata*. In addition, it is also predicted that their three-dimensional structure as a whole has a barrel shape, which is referred to as "β can".

However, the three-dimensional structures of such GFP-like fluorescent proteins from copepods, and in particular, the detailed structure of the fluorescent moiety formed in the mature fluorescent protein and the vicinity thereof, have not yet been analyzed. Thus, there have been no grounds for determining whether or not the approach applied to GFP from *A. victoria* can also be applied to the GFP-like fluorescent proteins from copepods as a technique for modifying the amino acid sequences of the fluorescent proteins so as to change the fluorescence wavelengths thereof. Also, there have been no grounds for determining whether or not a new approach effective for changing fluorescence wavelengths emitted from the GFP-like fluorescent proteins from copepods exists as a technique for changing the fluorescence wavelength by modifying the amino acid sequence of such a GFP-like fluorescent protein from copepod, other than the approach applied to the GFP from *A. victoria*.

The present invention has been made to solve the aforementioned problems. It is an object of the present invention to provide: a method, which comprises newly analyzing the three-dimensional structure of the GFP-like fluorescent protein from copepod, identifying a structural factor for determining the fluorescence wavelength emitted from the GFP-like fluorescent protein from copepod based on the analyzed three-dimensional structure, modifying amino acid residues associated with such a structural factor, so as to change the fluorescence wavelength, while maintaining recombinant expression efficiency that is equivalent to that of the wild-type fluorescent protein; and a modified fluorescent protein obtained by applying the aforementioned method. In particular, it is an object of the present invention to provide: a method, which comprises modifying the amino acid sequence of a wild-type protein, for instance, CpYGFP, the GFP-like fluorescent protein from *Chiridius poppei*, or ppluGFP2 (or a product named as "Cop-Green"), the GFP-like fluorescent protein from *Pontellina plutellina*, so as to change the fluorescence wavelength thereof, while maintaining recombinant expression efficiency that is equivalent to that of the wild-type fluorescent protein; and a modified fluorescent protein obtained by applying the aforementioned method.

Means for Solving the Problems

In order to solve the aforementioned problems, first, the present inventors have newly analyzed the three-dimensional structure of the GFP-like fluorescent protein from the copepod, and have identified structural factors for determining such fluorescence wavelength emitted from the GFP-like fluorescent protein from copepod based on the analyzed three-dimensional structures. In particular, using a GFP-like fluorescent protein from *Chiridius poppei*, CpYGFP, discovered by the present inventors, the inventors have conducted the recombinant expression of a mature fluorescent protein thereof having the wild-type amino acid sequence, which had obtained fluorescent property after the cyclization of its internal tripeptide site "GYG" forming the fluorescent moiety and the subsequent oxidation, so as to prepare a purified CpYGFP sample. The thus purified CpYGFP sample was subjected to crystallization, and the obtained crystals were subjected to X-ray crystal structure analysis. Thus, the three-dimensional structure of CpYGFP in such crystals was determined. As shown in FIG. 3, in the determined three-dimensional structure of CpYGFP, 11 β strands, one α helix ($\alpha_1$-helix) including GYG associated with the structure of the fluorescent moiety, and another short α helix ($\beta_2$-helix) constitute a barrel form referred to as "β can", which is an entire form commonly shown in GFP from *A. victoria* and DsRFP from *Discosoma striata*. In addition, such GYG included in the α helix located inside the barrel is subjected to cyclization and the subsequent oxidation, so as to form the following fluorescent moiety of p-hydroxybenzylideneimidazolinone structure.

Equilibrium between the ionized form and neutral form in p-hydroxybenzylideneimidazolinone structure of the wild-type CpYGFP, the imidazole ring on the side chain of His at position 52 is placed so as to overlap with a p-hydroxyphanyl group (phenol ring) portion derived from Tyr in the fluorescent moiety of p-hydroxybenzylideneimidazolinone structure. It is predicted that such an interaction (π-π-stacking) via the overlapping of the π-electrons of both rings has a function of red-shifting the fluorescence wavelength measured therein.

The aforementioned two points are considered to be structural differences in vicinity of the fluorescent moiety, which are characteristic for the three-dimensional structure of CpYGFP from *Chiridius poppei*, when compared with the three-dimensional structure of GFP from *A. victoria*. Based on such findings, the imidazole ring on the side chain of His at position 52 was indeed replaced with various amino acid residues, so as to produce modified proteins. A comparison was made in terms of the fluorescent properties of the modified proteins. From such comparison results, it is concluded that the modified proteins have the following effects.

That is to say, the imidazole ring on the side chain of His, the benzene ring on the side chain of Phe, the p-hydroxyphanyl group (phenol ring) on the side chain of Tyr, and the indole ring on the side chain of Trp, which are used as the amino acid residue at position 52, all have a π-π-stacking effect onto the p-hydroxyphanyl group (phenol ring) portion derived from Tyr in the fluorescent moiety of p-hydroxybenzylideneimidazolinone structure, and have a function to red-shift the fluorescence wavelength. On the other hand, when said amino acid residue at position 52 is replaced with Ala (side chain: $CH_3$—), Val (side chain: $CH_3$—$CH(CH_3)$—), Ile (side chain: $C_2H_5$—$CH(CH_3)$—), Leu (side chain: $CH_3$—$CH(CH_3)$—$CH_2$—), Gly (no side chain), Cys (side chain: HS—$CH_2$—), Met ($CH_3$—S—$C_2H_4$—), Ser (side chain: HO—$CH_2$—), or Thr (side chain: $CH_3$—CH(OH)—), all of which have no π-electron conjugated systems, there are no corresponding

[Chemical formula 7]

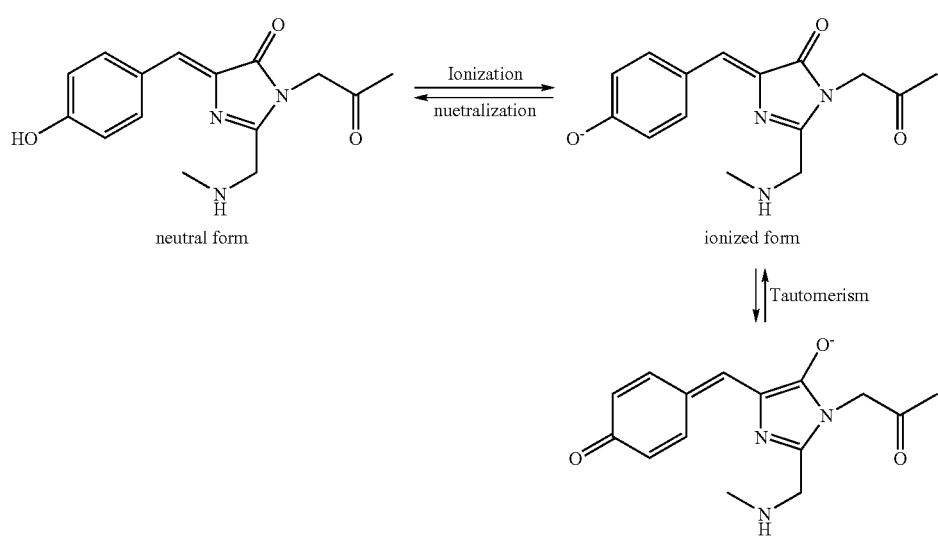

It has been revealed that a local steric configuration including amino acid residues existing in the vicinity of this fluorescent moiety is as shown in FIG. 4. Even in the case of wild-type CpYGFP, a form associated with fluorescence is the aforementioned ionized form. It is predicted that Thr at position 136 existing in a β strand ($\beta_6$) contributes to stabilization of the ionized form in some way. In addition, in the case interactions, and thus, the red-shift effect caused by the imidazole ring on the His side chain is lost. Moreover, when the amino acid residue at position 52 is replaced with Asp (side chain: HOOC—$CH_2$—) or Glu (side chain: HOOC—$C_2H_4$—) having ability to donate a proton, it exhibits the effect of decreasing the ionization ratio of the p-hydroxyphanyl group on the side chain of Tyr, and as a result, the ratio of the neutral form is increased. For example, a peak around 400 nm originated from the neutral form is added onto the excitation spectrum, and at the same time, a decrease in the apparent fluorescence intensity occurs.

On the other hand, as with the aforementioned GFP from *A. victoria*, even in the case of the wild-type CpYGFP, if Tyr in the "GYG" forming the fluorescent moiety thereof is replaced with His or Trp, it is predicted that a shift of the fluorescence wavelength occurs due to a difference in the π-electron conjugated systems of the formed fluorescent moieties. At that time, the present inventors have found that, when Tyr is replaced with Trp, the level of a blue shift found in such a modified form in the case of CpYGFP is significantly greater than the level of a blue shift observed in the CFP as to the GFP from *A. victoria*, and that the fluorescence thereof exceeds the wavelength range of a blue green color and reaches the wavelength range of a blue color.

Based on the aforementioned findings, the present inventors have conceived of a method of introducing a mutation into the amino acid sequence of CpYGFP from *Chiridius poppei* based on the three-dimensional structure of said CpYGFP, so as to change the maximum fluorescence wavelength of the fluorescence emitted from the obtained modified protein, thereby completing the present invention. In addition, as shown in FIG. 1, the CpYGFP from *Chiridius poppei* shows high homology at the amino acid sequence level with the ppluGFP2 from *Pontellina plutellina* (or a product named as "Cop-Green"). Accordingly, it can be considered that a local steric configuration including amino acid residues existing around this fluorescent moiety in the three-dimensional structure thereof, and in particular, the relative configuration between His at position 52 and the fluorescent moiety, exhibits extremely high similarity. Thus, the present inventors have also found that the method of the present invention is effective also for the ppluGFP2 from *Pontellina plutellina* (or a product named as "Cop-Green").

That is to say, one modified fluorescent protein of a first embodiment of the present invention is a modified fluorescent protein of a GFP-like fluorescent protein CpYGFP from *Chiridius poppei*, which is characterized in that it is any one of:

a modified fluorescent protein comprising an amino acid sequence wherein His at the $52^{nd}$ amino acid position is replaced with one amino acid selected from the aromatic amino acid group consisting of Phe, Tyr and Trp in the full-length amino acid sequence (SEQ ID NO: 1) of the CpYGFP:

```
MTTFKIESRI HGNLNGEKFE LVGGGVGEEG RLEIEMKTKD KPLAFSPFLL SHCMGYGFYH    60

FASFPKGTKN IYLHAATNGG YTNTRKEIYE DGGILEVNFR YTYEFNKIIG DVECIGHGFP   120

SQSPIFKDTI VKSCPTVDLM LPMSGNIIAS SYARAFQLKD GSFYTAEVKN NIDFKNPIHE   180

SFSKSGPMFT HRRVEETHTK ENLAMVEYQQ VFNSAPRDM                          219
``` and exhibiting a red shifted fluorescence peak wavelength, when compared with the fluorescence peak wavelength of the CpYGFP;

a modified fluorescent protein comprising an amino acid sequence wherein His at the $52^{nd}$ amino acid position is replaced with one amino acid selected from the amino acid group consisting of Ala, Val, Ile, Leu, Gly, Cys, Met, Ser and Thr in the full-length amino acid sequence of the CpYGFP, and exhibiting a blue shifted fluorescence peak wavelength, when compared with the fluorescence peak wavelength of the CpYGFP; and a modified fluorescence protein comprising an amino acid sequence wherein His at the $52^{nd}$ amino acid position is replaced with one amino acid selected from the amino acid group consisting of Asp, Asn, Glu and Gln in the full-length amino acid sequence of the CpYGFP, and exhibiting a blue shifted fluorescence peak wavelength, when compared with the fluorescence peak wavelength of the CpYGFP.

One of preferred examples of said group of the modified fluorescent proteins from the CpYGFP is a modified fluorescent protein CpYGFP-H52F (SEQ ID NO:6) comprising an amino acid sequence wherein the His at the $52^{nd}$ amino acid position is replaced with Phe in the full-length amino acid sequence of the CpYGFP, and exhibiting a red shifted fluorescence peak wavelength, when compared with the fluorescence peak wavelength of the CpYGFP.

Another one of the preferred examples of said group of modified fluorescent proteins from the CpYGFP is a modified fluorescent protein CpYGFP-H52T (SEQ ID NO:8) comprising an amino acid sequence wherein the His at the $52^{nd}$ amino acid position is replaced with Thr in the full-length amino acid sequence of the CpYGFP, and exhibiting a blue shifted fluorescence peak wavelength, when compared with the fluorescence peak wavelength of the CpYGFP.

Another one of the preferred examples of said group of modified fluorescent proteins from the CpYGFP is a modified fluorescent protein CpYGFP-H52D (SEQ ID NO:10) comprising an amino acid sequence wherein the His at the $52^{nd}$ amino acid position is replaced with Asp in the full-length amino acid sequence of the CpYGFP, and exhibiting a blue shifted fluorescence peak wavelength, when compared with the fluorescence peak wavelength of the CpYGFP.

Another modified fluorescent protein of the first embodiment of the present invention is a modified fluorescent protein of a GFP-like fluorescent protein ppluGFP2 from *Pontellina plutellina* showing high homology with a GFP-like fluorescent protein CpYGFP from *Chiridius poppei*, which is characterized in that it is any one of:

a modified fluorescent protein comprising an amino acid sequence wherein His at the $54^{th}$ amino acid position in the full-length amino acid sequence (SEQ ID NO: 4) of the ppluGFP2, which corresponds to the His at the $52^{nd}$ amino acid position in the full-length amino acid sequence of the CpYGFP, is replaced with one amino acid selected from the aromatic amino acid group consisting of Phe, Tyr and Trp:

```
MPAMKIECRI TGTLNGVEFE LVGGGEGTPE QGRMTNKMKS TKGALTFSPY LLSHVMGYGF    60

YHFGTYPSGY ENPFLHAINN GGYTNTRIEK YEDGGVLHVS FSYRYEAGRV IGDFKVVGTG   120

FPEDSVIFTD KIIRSNATVE HLHPMGDNVL VGSFARTFSL RDGGYYSFVV DSHMHFKSAI   180

HPSILQNGGP MFAFRRVEEL HSNTELGIVE YQHAFKTPIA FA                     222
``` and exhibiting a red shifted fluorescence peak wavelength, when compared with the fluorescence peak wavelength of the ppluGFP2;

a modified fluorescent protein comprising an amino acid sequence wherein the His at the 54$^{th}$ amino acid position is replaced with one amino acid selected from the amino acid group consisting of Ala, Val, Ile, Leu, Gly, Cys, Met, Ser and Thr in the full-length amino acid sequence of the ppluGFP2, and exhibiting a blue shifted fluorescence peak wavelength, when compared with the fluorescence peak wavelength of the ppluGFP2; and a modified fluorescent protein comprising an amino acid sequence wherein the His at the 54$^{th}$ amino acid position is replaced with one amino acid selected from the amino acid group consisting of Asp, Asn, Glu and Gln in the full-length amino acid sequence of the ppluGFP2, and exhibiting a blue shifted fluorescence peak wavelength, when compared with the fluorescence peak wavelength of the ppluGFP2.

One of the preferred examples of said group of modified fluorescent proteins from the ppluGFP2 is a modified fluorescent protein comprising an amino acid sequence wherein the His at the 54$^{th}$ amino acid position is replaced with Phe in the full-length amino acid sequence of the ppluGFP2.

One of preferred examples of said group of modified fluorescent proteins from the ppluGFP2 is a modified fluorescent protein comprising an amino acid sequence wherein the His at the 54$^{th}$ amino acid position is replaced with Thr in the full-length amino acid sequence of the ppluGFP2.

Another one of preferred examples of said group of modified fluorescent proteins from the ppluGFP2 is a modified fluorescent protein comprising an amino acid sequence wherein the His at the 54$^{th}$ amino acid position is replaced with Asp in the full-length amino acid sequence of the ppluGFP2.

On the other hand, one modified fluorescent protein of a second embodiment of the present invention is a modified fluorescent protein of the GFP-like fluorescent protein CpYGFP from *Chiridius poppei*, which is characterized in that it is any one of:

a modified fluorescent protein CpYGFP-Y56W comprising an amino acid sequence wherein Tyr at the 56$^{th}$ amino acid position is replaced with Trp in the full-length amino acid sequence (SEQ ID NO: 1) of the CpYGFP:

```
MTTFKTESRI HGNLNGEKFE LVGGGVGEEG RLEIEMKTKD KPLAFSPFLL SHCMGYGFYH    60

FASFPKGTKN IYLHAATNGG YTNTRKEIYE DGGILEVNFR YTYEFNKIIG DVECIGHGFP   120

SQSPIFKDTI VKSCPTVDLM LPMSGNIIAS SYARAFQLKD GSFYTAEVKN NIDFKNPIHE   180

SFSKSGPMFT HRRVEETHTK ENLAMVEYQQ VFNSAPRDM                         219
``` and exhibiting a blue shifted fluorescence peak wavelength, when compared with the fluorescence peak wavelength of the CpYGFP;

a modified fluorescent protein CpYGFP-Y56W, V194S, comprising an amino acid sequence wherein the Tyr at the 56$^{th}$ amino acid position is replaced with Trp, and Val at the 194$^{th}$ amino acid position is further replaced with Ser in the full-length amino acid of the CpYGFP, and exhibiting a blue shifted fluorescence peak wavelength, when compared with the fluorescence peak wavelength of the CpYGFP; and a modified fluorescence protein CpYGFP-Y56W, V194S, T136A, comprising an amino acid sequence wherein the Tyr at the 56$^{th}$ amino acid position is replaced with Trp, the Val at the 194$^{th}$ amino acid position is replaced with Ser, and Thr at the 136$^{th}$ amino acid position is further replaced with Ala, and exhibiting a blue shifted fluorescence peak wavelength, when compared with the fluorescence peak wavelength of the CpYGFP.

Another modified fluorescent protein of the second embodiment of the present invention is a modified fluorescent protein of the GFP-like fluorescent protein ppluGFP2 from *Pontellina plutellina* showing high homology with the GFP-like fluorescent protein CpYGFP from *Chiridius poppei*, which is characterized in that it is any one of:

a modified fluorescent protein comprising an amino acid sequence wherein Tyr at the 58$^{th}$ amino acid position in the full-length amino acid sequence (SEQ ID NO: 4) of the ppluGFP2, which corresponds to Tyr at the 56$^{th}$ amino acid position in the full-length amino acid sequence of the CpYGFP, is replaced with Trp:

```
MPAMKIECRI TGTLNGVEFE LVGGGEGTPE QGRMTNKMKS TKGALTFSPY LLSHVMGYGF    60

YHFGTYPSGY ENPFLHAINN GGYTNTRIEK YEDGGVLHVS FSYRYEAGRV IGDFKVVGTG   120

FPEDSVIFTD KIIRSNATVE HLHPMGDNVL VGSFARTFSL RDGGYYSFVV DSHMHFKSAI   180

HPSILQNGGP MFAFRRVEEL HSNTELGIVE YQHAFKTPIA FA;                    222
``` a modified fluorescent protein comprising an amino acid sequence wherein Tyr at the 58$^{th}$ amino acid position is replaced with Trp, and Val at the 197$^{th}$ amino acid position is further replaced with Ser in the full-length amino acid sequence of the ppluGFP2; and a modified fluorescence protein comprising an amino acid sequence wherein the Tyr at the 58$^{th}$ amino acid position is replaced with Trp, the Val at the 197$^{th}$ amino acid position is replaced with Ser, and the Thr at the 138$^{th}$ amino acid position is further replaced with Ala, in the full-length amino acid of the ppluGFP2.

Effect of Invention

In the case of the modified fluorescent protein of the first embodiment of the present invention obtained by applying a method of changing the fluorescence wavelength of a fluorescent protein, instead of a method of replacing with another amino acid residue having an aromatic ring group, such as His or Trp, Tyr in "XYG" constituting the fluorescent moiety of a wild-type GFP-like fluorescent protein from Copepoda, including, as typical examples, the GFP-like fluorescent protein from *Chiridius poppei*, CpYGFP, and the GFP-like fluorescent protein from *Pontellina plutellina*, ppluGFP2, when the position of the aforementioned Tyr is defined as the n$^{th}$ position, the amino acid residue located at the (n−4)$^{th}$ position is defined as an amino acid residue having an aromatic ring group, so as to cause the "π-π-stacking" between the p-hydroxyphenyl group (phenol ring) on the side chain of Tyr and the aromatic ring group on the side chain of the amino acid residue at the (n−4)$^{th}$ position. Thereby, the fluorescence wavelength emitted from the modified fluorescent protein can be shifted to a long wavelength side, when compared with the fluorescence wavelength emitted from the wild-type fluorescent protein. To the contrary, when the position of the Tyr is defined as the n$^{th}$ position, if the amino acid residue at the (n−4)$^{th}$ position is defined as an amino acid residue having no aromatic ring groups, the aforementioned effect caused by the "π-π-stacking" is eliminated. Thereby, the fluorescence wavelength emitted from the modified fluorescent protein can be shifted to a short wavelength side, when compared with the fluorescence wavelength emitted from the wild-type fluorescent protein. When the method of the present invention is applied, a mutation is not introduced into the "XYG" constituting the fluorescent moiety of a wild-type fluorescent protein. Thus, the process of forming a fluorescent moiety through the cyclization and the subsequent oxidation in such a modified fluorescent protein is substantially equivalent to said process in the wild-type fluorescent protein.

Moreover, in the case of the modified fluorescent protein of the second embodiment of the present invention obtained by applying a method of changing the fluorescence wavelength of a fluorescent protein, Tyr in "XYG" constituting the fluorescent moiety of a wild-type GFP-like fluorescent protein from Copepoda, including, as typical examples, the GFP-like fluorescent protein from *Chiridius poppei*, CpYGFP (SEQ ID NO:1), and the GFP-like fluorescent protein from *Pontellina plutellina*, ppluGFP2 (SEQ ID NO:4), is replaced with Trp, so that a fluorescence wavelength emitted from the modified fluorescent protein can be shifted to a short wavelength side, when compared with a fluorescence wavelength emitted from a wild-type fluorescent protein. In particular, if a method of changing the fluorescence wavelength of the fluorescent protein of the second embodiment of the present invention is applied to modify the GFP-like fluorescent protein from *Chiridius poppei*, CpYGFP, or the GFP-like fluorescent protein from *Pontellina plutellina*, ppluGFP2, a modified fluorescent protein having a blue color tone, which exhibits a fluorescence spectrum showing a substantially single peak wavelength, can be obtained.

BRIEF DESCRIPTION OF THE DRAWINGS

FIG. 4 is a partial structural view showing the location of the fluorescent moiety of the p-hydroxybenzylideneimidazolinone structure that is constructed from "GYG" of the GFP-like fluorescent protein from *Chiridius poppei*, CpYGFP, and the side chains of amino acid residues located in the vicinity of said fluorescent moiety, such as His$^{52}$, Tyr$^{59}$, Arg$^{85}$, Thr$^{136}$, Asn$^{170}$ and Glu$^{207}$, and hydrogen-bondings presumed and the position of the oxygen atoms of water molecules fixed by the hydrogen-bonding;

FIG. 5 shows the results obtained by the alignment of amino acid sequences constituting the corresponding secondary structures based on a comparison made among the newly analyzed structure in crystal of the GFP-like fluorescent protein from *Chiridius poppei*, CpYGFP (SEQ ID NO:1), the previously reported structures in crystal of DsRed (SEQ ID NO:31) and of aqGFP (SEQ ID NO:32), wherein the partial sequences of such secondary structures identified in the structure in crystal of CpYGFP from the alignment of the amino acid sequences are indicated below the sequences;

FIG. 6 is a view showing the amino acid sequences of cpYGFP (SEQ ID NO:1), CpYGFP-Y56W, V194S (CpYGFP mutant 1; SEQ ID NO:14) and CpYGFP-Y56W, V194S, T136A (CpYGFP mutant 2; SEQ ID NO:16), which are modified fluorescent proteins produced by replacing "GYG" forming the fluorescent moiety of the GFP-like fluorescent protein from *Chiridius poppei*, CpYGFP, with "GWG";

FIG. 7-1 is a view showing a comparison made between the shapes of the fluorescence/excitation spectra of the GFP-like fluorescent protein from *Chiridius poppei*, CpYGFP, and the shapes of the fluorescence/excitation spectra of the modified fluorescent protein, CpYGFP-H52T;

FIG. 7-2 is a view showing a comparison made between the shapes of the fluorescence/excitation spectra of the modified fluorescent protein, CpYGFP-H52D, and the shapes of the fluorescence/excitation spectra of the modified fluorescent protein, CpYGFP-H52F;

BEST MODE FOR CARRYING OUT THE INVENTION

Figure 2:
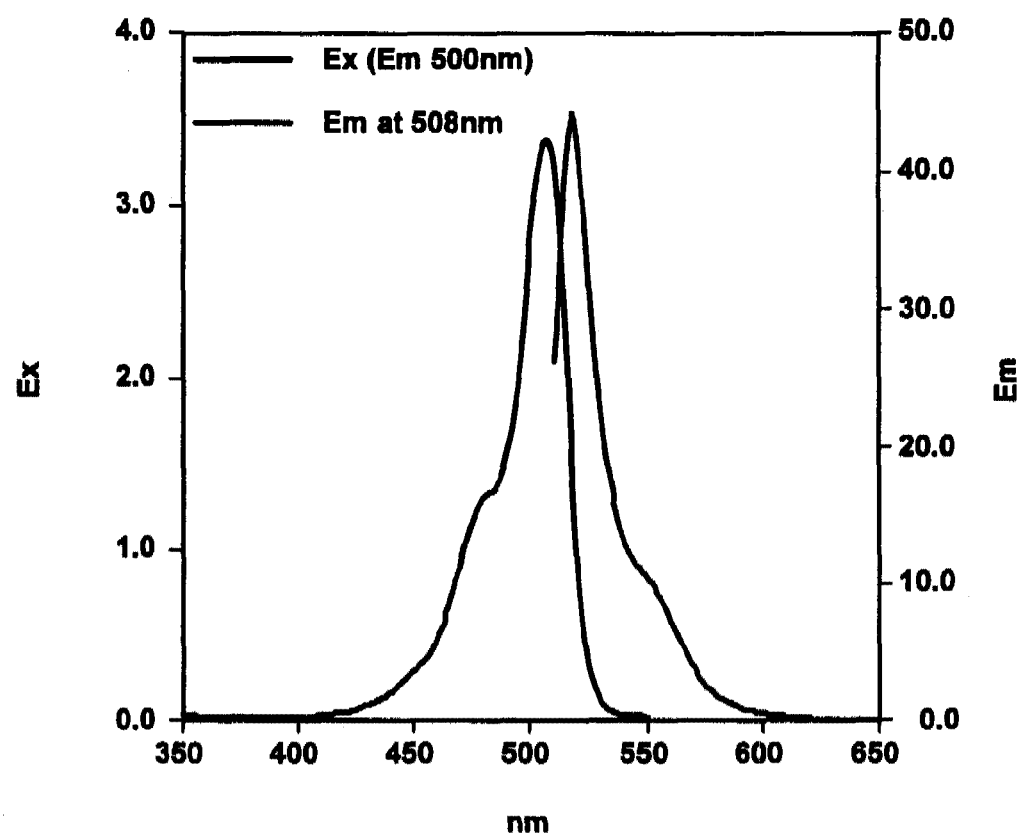
FIG. 2 is a view showing the fluorescence spectrum and excitation spectrum of the GFP-like fluorescent protein from *Chiridius poppei*, CpYGFP.

The present invention will be explained more in detail below.

A method of changing the fluorescence wavelength of the GFP-like fluorescent protein of the first embodiment of the present invention is one of methods of producing a modified fluorescent protein based on the GFP-like fluorescent protein from *Chiridius poppei*, CpYGFP, or the GFP-like fluorescent protein from *Pontellina plutellina*, ppluGFP2, which shifts the color tone of the fluorescence emitted from the wild-type GFP-like fluorescent proteins, namely, the maximum fluorescence wavelength (fluorescence peak wavelength) observed on their fluorescence spectra, to the long wavelength side (red shift) or to the short wavelength side (blue shift).

Specifically, as a result of newly analyzing the crystal structure of the GFP-like fluorescent protein from *Chiridius poppei*, CpYGFP, it was confirmed that a fluorescent moiety existing in said GFP-like fluorescent protein is a p-hydroxybenzylideneimidazolinone structure formed via the cyclization and dehydration process of "GYG". Moreover, it was found that the imidazole ring on the side chain of $His^{52}$ is located at an arrangement capable of "π-π-stacking" with a p-hydroxyphenyl group (phenol ring) derived from $Tyr^{56}$ contained in the fluorescent moiety of p-hydroxybenzylideneimidazolinone structure.

In the first embodiment of the present invention, utilizing this structural characteristics, the imidazole ring derived from $His^{52}$ is replaced with an aromatic amino acid capable of adapting the corresponding configuration, a benzene ring derived from Phe, or a phenol ring (p-hydroxyphenyl group) derived from Tyr, or the indole ring derived from Trp, so that the interactions of π-electron conjugated systems caused by the "π-π-stacking" can be increased, and so that the excitation energy in a fluorescent state can be decreased. As a result, the maximum fluorescence wavelength (fluorescence peak wavelength) of such a modified fluorescent protein is shifted to the long wavelength side (red-shifted), when compared with the maximum fluorescence wavelength (fluorescence peak wavelength) of wild-type CpYGFP.

Otherwise, $His^{52}$ having an imidazole ring is replaced with an amino acid with a chain structure having no π-electron conjugated systems that is capable of adapting the corresponding configuration, such as Ala (side chain: $CH_3$—), Val (side chain: $CH_3$—$CH(CH_3)$—), Ile (side chain: $C_2H_5$—CH($CH_3$)—), Leu (side chain: $CH_3$—$CH(CH_3)$—$CH_2$—), Gly (no side chain), Cys (side chain: HS—$CH_2$—), Met ($CH_3$—S—$C_2H_4$—), Ser (side chain: HO—$CH_2$—), or Thr (side chain: $CH_3$—CH(OH)—), so as to eliminate the interaction caused by the "π-π-stacking." As a result, the maximum fluorescence wavelength (fluorescence peak wavelength) of such a modified fluorescent protein is shifted to the short wavelength side (blue-shifted), when compared with the maximum fluorescence wavelength (fluorescence peak wavelength) of a wild-type CpYGFP.

In addition, $His^{52}$ having an imidazole ring is replaced with an amino acid having no π-electron conjugated systems that is capable of adapting the corresponding configuration, such as Asp (side chain: —$CH_2$—COOH), Glu (side chain: —$C_2H_4$—COOH), Asn (side chain: —$CH_2$—$CONH_2$), or Gln (side chain: —$C_2H_4$—$CONH_2$). As a result, the maximum fluorescence wavelength (fluorescence peak wavelength) of such a modified fluorescent protein is shifted to the short wavelength side (blue-shifted), when compared with the maximum fluorescence wavelength (fluorescence peak wavelength) of wild-type CpYGFP.

At that time, an amino acid replaced for $His^{52}$, the side chain of which has a size equivalent to that of the imidazole ring, does not cause steric hindrance to the structural change of "GYG" during its cyclization process, and thus it is more preferable. For example, among aromatic amino acids, the benzene ring of Phe replaced for $His^{52}$ has a size equivalent to the imidazole ring of His, and thus it is more preferable.

Moreover, as shown in FIG. 5, from the results obtained by aligning partial amino acid sequences constituting secondary structures based on crystal structures, it is found that such "XYG" constituting a fluorescent moiety is comprised in an α helix-like secondary structure ($α_1$-helix) having the corresponding length in all of the GFP from *A. victoria*, the DsRFP from *Discosoma striata*, and the CpYGFP from *Chiridius poppei*. At that time, in the case of the GFP from *A. Victoria* (aqGFP), Thr exists at the position of the amino acid corresponding to $His^{52}$ of the CpYGFP from *Chiridius poppei*. Taking into consideration this point, when such $His^{52}$ of the CpYGFP from *Chiridius poppei* is replaced with an amino acid with a chain structure having no π-electron conjugated systems, so that the maximum fluorescence wavelength (fluorescence peak wavelength) is shifted to the short wavelength side when compared with the maximum fluorescence wavelength of wild-type CpYGFP (blue shift), it is considered that substitution with Thr is one of more preferred choices.

On the other hand, if the $His^{52}$ of the CpYGFP from *Chiridius poppei* is replaced with Asp (side chain: —$CH_2$—COOH) or Glu (side chain: —$C_2H_4$—COOH) having ability to donate protons, the equilibrium between the ionized form and the neutral form is inclined to the neutral form in the p-hydroxybenzylideneimidazolinone structure of its fluorescent moiety. Thus, it is considered that a tendency to decrease fluorescence intensity attended with a decrease in pH is suppressed at a level higher than the case of the CpYGFP from *Chiridius poppei*. From this viewpoint, a modified fluorescent protein obtained by replacing $His^{52}$ with Asp (side chain: —$CH_2$—COOH) or Glu (side chain: —$C_2H_4$—COOH) having ability to donate a proton has the effect of shifting its maximum fluorescence wavelength (fluorescence peak wavelength) to the short wavelength side, when compared with the maximum fluorescence wavelength (fluorescence peak wavelength) of the wild-type fluorescent protein. At the same time, the aforementioned modified fluorescent protein also has the effect of suppressing a tendency to decrease fluorescence intensity attended with a decrease in pH. Thus, such a modified fluorescent protein is one of preferred modified fluorescent proteins.

Figure 1:
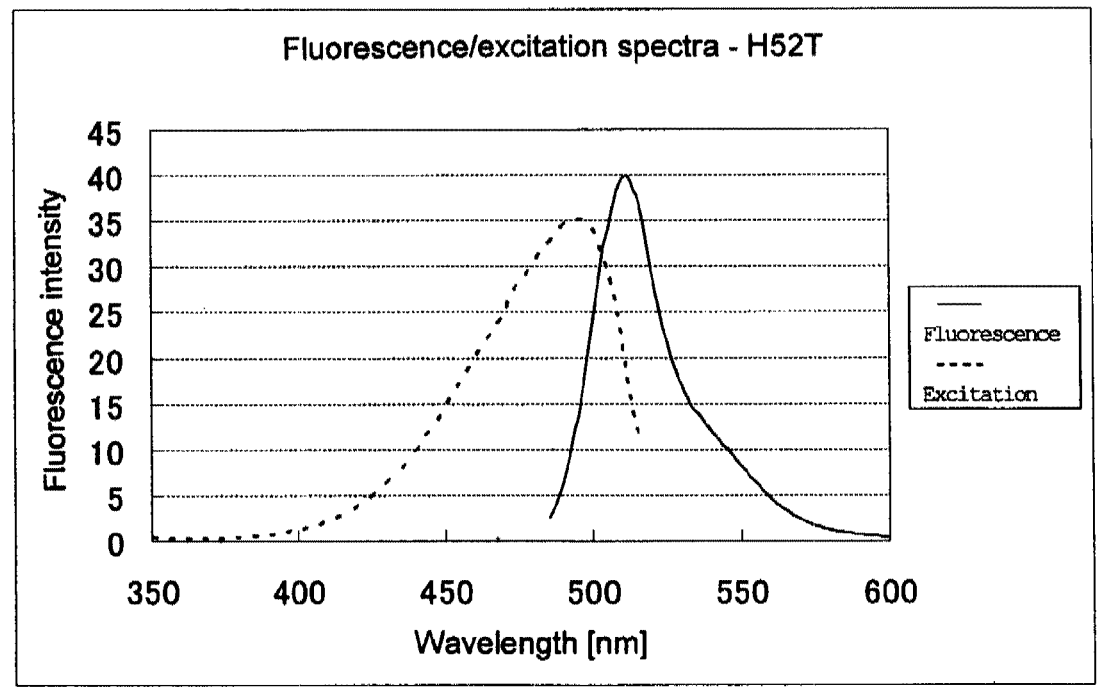
FIG. 1 shows the results obtained by aligning the amino acid sequence of the GFP-like fluorescent protein from *Chiridius poppei*, CpYGFP (SEQ ID NO:1), with the amino acid sequence of the GFP-like fluorescent protein from *Pontellina plutellina*, ppluGFP2 (SEQ ID NO:4) (or a product named as "Cop-Green"), wherein the alignment of the amino acid sequences shows homology between the two proteins.
Figure 7:
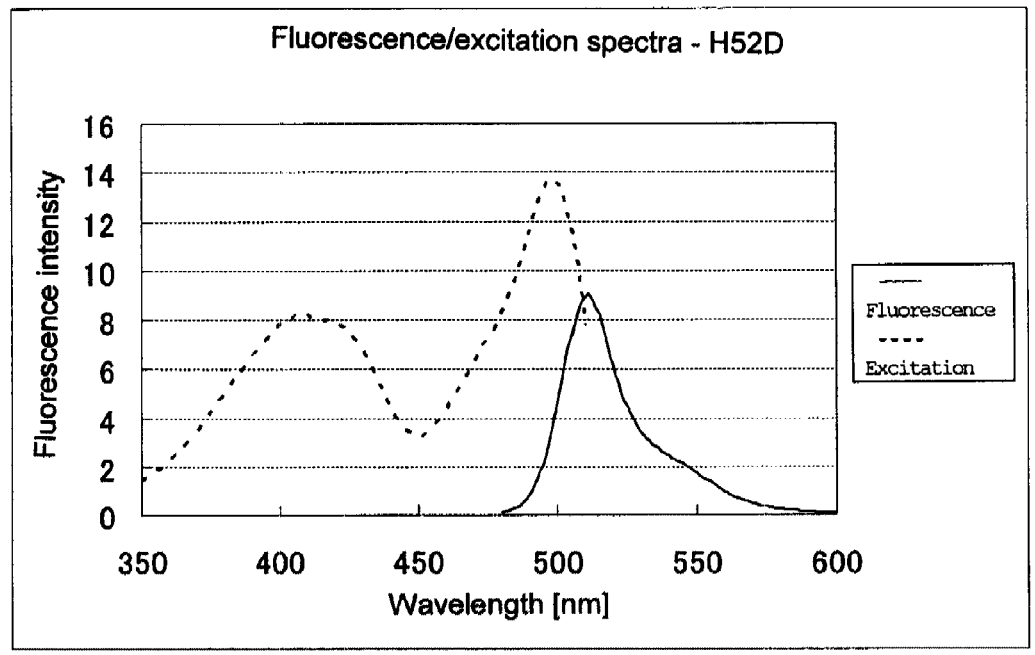
Figure 2:
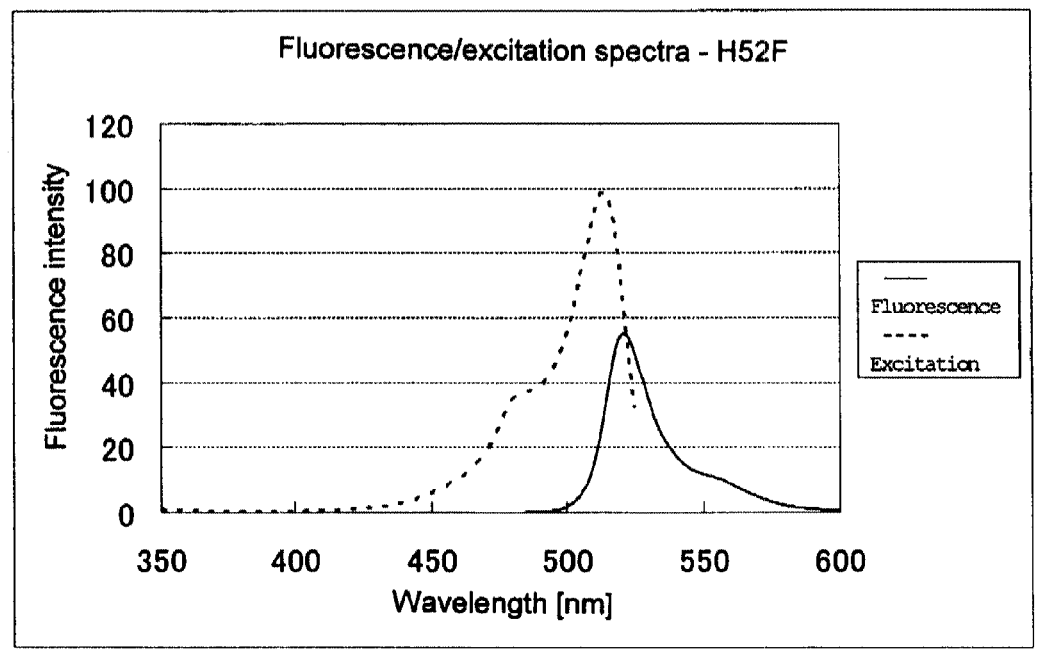

As shown in FIG. 1, when the primary structure (amino acid sequence) of the CpYGFP from *Chiridius poppei* is compared with that of the GFP-like fluorescent protein from *Pontellina plutellina*, ppluGFP2, they have significantly high similarity. In addition, if focusing on the partial amino acid sequence forming a secondary structure identified on basis of the newly analyzed crystal structure of the wild-type CpYGFP, it is assumed that the two fluorescent proteins have almost the same three-dimensional structure. In particular, in terms of the partial amino acid sequence of the α helix-like secondary structure ($α_1$-helix) including "GYG" constituting the fluorescent moiety, the two fluorescent proteins show high identity. Thus, in the case of ppluGFP2 as well, it is assumed that the imidazole ring on the side chain of $His^{52}$ is located at the arrangement capable of "π-π-stacking" with the p-hydroxyphenyl group (phenol ring) derived from $Tyr^{56}$ included in the p-hydroxybenzylideneimidazolinone structure of the formed fluorescent moiety. Accordingly, the effect to be obtained in ppluGFP2 is essentially equivalent to that obtained by replacing $His^{52}$ with another amino acid in CpYGFP.

With regard to the fluorescent properties of the wild-type ppluGFP2, it has been reported that its fluorescent peak wavelength is 502 nm and its peak wavelength on an excitation spectrum is 482 nm. When compared with the wild type CpYGFP as shown in FIG. 2 having a fluorescence peak wavelength of 517 nm and a peak wavelength on an excitation spectrum of 509 nm, both values of the wild-type ppluGFP2 are shifted to the short wavelength side. In the two above fluorescent proteins, it is assumed that the imidazole ring on the side chain of His$^{52}$ is located at the arrangement capable of "π-π-stacking" with the p-hydroxybenzylideneimidazolinone structure of the fluorescent moiety. However, as apparent measurement results, the effect of shifting a fluorescence peak wavelength and a peak wavelength on an excitation spectrum to the long wavelength side (red shift) caused by the aforementioned "π-π-stacking" is not high in the wild-type ppluGFP2.

For example, aqGFP exhibits a fluorescence peak wavelength of 504 nm and a peak wavelength on an excitation spectrum of 470 to 475 nm. EGFP (enhanced GFP), wherein the fluorescent moiety has been converted to an ionized form, exhibits a fluorescence peak wavelength of 507 to 509 nm and a peak wavelength on an excitation spectrum of 485 nm. Hence, the fluorescence peak wavelength and peak wavelength on an excitation spectrum of aqGFP, which is contributed by a neutral form, are shifted to the short wavelength side, when compared with those of EGFP. That is, these results demonstrate that, if a neutral form highly contributes to the form of a fluorescent moiety, the observed fluorescence peak wavelength and peak wavelength on an excitation spectrum are shifted to the short wavelength side.

Taking into consideration a mechanism of shifting such a fluorescence peak wavelength and a peak wavelength on an excitation spectrum, which reflects a difference in contribution of a neutral form and an ionized form, such a neutral form more highly contributes to wild-type ppluGFP2, and thus it is considered that the effect of shifting such a fluorescence peak wavelength and a peak wavelength on an excitation spectrum to the long wavelength side (red shift) caused by the aforementioned "π-π-stacking" is not apparently reflected on the spectrum. In other words, even in the case of such wild-type ppluGFP2, it is considered that the assumption that the imidazole ring on the side chain of His$^{52}$ is located at a position capable of "π-π-stacking" with a p-hydroxyphenyl group (phenol ring) derived from Tyr$^{56}$ does not contradict the fact that the effect of shifting such a peak wavelength is not obtained on the fluorescence spectrum or on the excitation spectrum.

Accordingly, the effect of replacing the aforementioned His$^{52}$ with another amino acid on the ppluGFP2 is substantially equivalent to that on the CpYGFP. If the His$^{52}$ of the ppluGFP2 is replaced with a chain structure amino acid having no π-electron conjugated systems, such as Ala, Val, Ile, Leu, Gly, Cys, Met, Ser, or Thr, so as to eliminate the interaction caused by "π-π-stacking", the fluorescence peak wavelengths of the obtained modified fluorescent protein on the fluorescence spectrum and on the excitation spectrum are apparently not different from those of wild-type ppluGFP2. However, the entire form of the fluorescence spectrum of the modified fluorescent protein is changed, and the color tone obtained by integration of such forms is changed and is blue shifted by the aforementioned substitution. Likewise, the His$^{52}$ of the ppluGFP2 is replaced with an amino acid having no π-electron conjugated systems, such as Asp, Glu, Asn, or Gln, so as to eliminate the interaction caused by "π-π-stacking", the fluorescence peak wavelengths of the obtained modified fluorescent protein on the fluorescence spectrum and on the excitation spectrum are apparently not different from those of wild-type ppluGFP2. However, the entire form of the fluorescence spectrum of the modified fluorescent protein is changed, and the color tone obtained by integration of such forms is changed and is blue shifted by the aforementioned replacement.

On the other hand, if the His$^{52}$ of the ppluGFP2 is replaced with an aromatic amino acid having a greater π-electron conjugated system, such as Phe, Tyr, or Trp, so as to increase the interaction caused by the "π-π-stacking", the fluorescence peak wavelengths of the obtained modified fluorescent protein on the fluorescence spectrum and on the excitation spectrum are even apparently shifted to the long wavelength side (red-shifted), when compared with the wavelengths of wild-type ppluGFP2.

A method of shifting a fluorescence peak wavelength and a peak wavelength on an excitation spectrum to the long wavelength side (red shift) utilizing the interaction caused by the "π-π-stacking" is also applied to a modified fluorescent protein YFP based on the aqGFP.

In the case of this YFP-type modified fluorescent protein, with respect to the p-hydroxyphenyl group (phenol ring) derived from Tyr$^{66}$ of "SYG" constituting the fluorescent moiety of the aqGFP, Thr$^{203}$ existing in a β$_{10}$ strand is replaced with an amino acid residue having a π-electron conjugated system, such as His, Phe, or Tyr, so that the "π-π-stacking" can be induced. In the three-dimensional structure of YFP based on aqGFP, such a β$_{10}$ strand is located close to the fluorescent moiety, and thus the aforementioned induction of the "π-π-stacking" incidentally occurs. Accordingly, YFP has been practically problematic in that the formation efficiency of a fluorescent moiety exhibiting a desired fluorescence peak wavelength is influenced by the environment wherein cyclization and dehydration processes progress.

In contrast, in the three-dimensional structure of CpYGFP, for example, the orientation of the side chain of His$^{52}$ comprised in an α helix-like secondary structure (α$_1$-helix) including "GYG" is univocally determined during cyclization and dehydration processes occurred to the "GYG". Thus, when His$^{52}$ is replaced with Phe, Tyr, or Trp, an aromatic ring group existing on the side chain of such an amino acid residue substantially has the same orientation as that of an imidazole ring existing on the side chain of His$^{52}$. That is to say, a fluorescent moiety is formed form the "GYG", and at the same time, the aromatic ring group existing on the side chain of such an amino acid residue is automatically positioned at an orientation capable of "π-π-stacking".

As a result, in the modified fluorescent protein of the first embodiment of the present invention wherein His$^{52}$ is replaced with Phe, Tyr, or Trp, the influence caused by the environment wherein cyclization and dehydration processes progress on the formation efficiency of a fluorescent moiety exhibiting a shift to a desired long wavelength side can be suppressed to such an extent that it does not cause a practical problem.

In ppluGFP2 also, the partial amino acid sequence (amino acids at positions 49-63) of the helix-like secondary structure (α$_1$-helix) including "GYG" shows extremely high identity with the α$_1$-helix of CpYGFP (amino acids at positions 47-61). Thus, in a modified fluorescent protein wherein His$^{54}$ is replaced with Phe, Tyr or Trp, the influence caused by the environment wherein cyclization and dehydration processes progress on the formation efficiency of a fluorescent moiety exhibiting a shift to a desired long wavelength side can be suppressed to such an extent that it does not cause a practical problem.

A method of changing the fluorescence wavelength of the GFP-like fluorescent protein of the second embodiment of the present invention is one of methods of producing a modified fluorescent protein based on the GFP-like fluorescent protein from *Chiridius poppei*, CpYGFP, or the GFP-like fluorescent protein from *Pontellina plutellina*, ppluGFP2, which shifts the color tone of a fluorescence emitted from such wild-type GFP-like fluorescent proteins, namely the maximum fluorescence wavelength (fluorescence peak wavelength) observed on their fluorescence spectra, to the short wavelength side (blue shift).

In the second embodiment of the present invention, "GYG" constituting the fluorescent moiety of either CpYGFP or ppluGFP2 is changed to "GWG", so that the formed fluorescent moiety can be changed from a p-hydroxybenzylidene-imidazolinone structure to an indole-3-yl-methylideneimidazolinone structure, and as a result, the fluorescence peak wavelength of the obtained modified fluorescent protein can be shifted to the short wavelength side, when compared with that of a wild-type fluorescent protein (blue shift).

In both cases of CFP obtained by replacing "SYG" constituting the fluorescent moiety of aqGFP with "SWG," and BFP obtained by replacing the "SYG" with "SHG," the fluorescence peak wavelength of the obtained modified fluorescent protein is shifted to the short wavelength side, when compared with that of a wild-type fluorescent protein (blue shift), by changing the fluorescent moiety itself. However, with regard to the fluorescence spectrum and excitation spectrum of such CFP and BFP, at least two peaks closely come into contact with one another, so as to constitute a broad multimodal peak. Such two or more peaks are cause by different states, and it is assumed that a certain type of equilibrium relation exists between the two states. In general, when such peaks are distributed at the same level of abundance ratio in such two or more states, the entire shape of a spectrum is often changed due to a change in the abundance ratio by an extrinsic factor.

In contrast, as described in the exemplary embodiments below, the fluorescence spectrum or excitation spectrum of the modified fluorescent protein of the second embodiment of the present invention exhibits a monomodal peak, which is considered to be originated from a substantially single state. That is, the modified fluorescent protein of the second embodiment of the present invention exhibits light absorption to a substantially single state and fluorescence. Thus, induction of a change in the shape of the spectrum due to an extrinsic factor is prevented.

In addition, it is assumed that the fluorescent moiety of the modified fluorescent protein of the second embodiment of the present invention is an indole-3-yl-methylideneimidazolinone structure formed from "GWG." The fluorescence peak wavelength thereof is 460 nm. The fluorescence peak wavelength of a CFP-type fluorescent protein also having such an indole-3-yl-methylideneimidazolinone structure as a fluorescent moiety is 476 to 485 nm. Thus, when the fluorescence peak wavelength of the modified fluorescent protein of the second embodiment of the present invention is compared with that of the CFP-type fluorescent protein, the shifted amount (blue shift) to the short wavelength side of the aforementioned modified fluorescent protein is superior to that of the CFP-type fluorescent protein. Even if the fluorescence peak wavelength of the modified fluorescent protein of the second embodiment of the present invention is compared with the fluorescence peak wavelength of BFP having a 1H-imidazole-4-yl-methylideneimidazolinone structure as a fluorescent moiety that is 440 to 448 nm, the shifted amount (blue shift) to the short wavelength side of the aforementioned modified fluorescent protein is substantially equivalent to that of BFP.

The modified fluorescent proteins obtained by applying the methods of the first and second embodiments of the present invention are produced in the form of recombinant proteins, using a gene obtained by performing site-directed mutagenesis on the gene encoding the wild-type fluorescent protein. At that time, as the gene encoding the wild-type fluorescent protein, for example, as a gene encoding CpYGFP from *Chiridius poppei*, DNA having the following nucleotide sequence, which corresponds to cDNA prepared from mRNA encoding the CpYGFP, can be used.

```
AGAACACTCA GTGTATCCAG TTTTCCGTCC TACTACAAAC                              40

ATG ACA ACC TTC AAA ATC GAG TCC CGG ATC CAT GGC AAC CTC AAC GGG         88
 M   T   T   F   K   I   E   S   R   I   H   G   N   L   N   G
 1               5                   10                  15

GAG AAG TTC GAG TTG GTT GGA GGT GGA GTA GGT GAG GAG GGT CGC CTC        136
 E   K   F   E   L   V   G   G   G   V   G   E   E   G   R   L
                 20                  25                  30

GAG ATT GAG ATG AAG ACT AAA GAT AAA CCA CTG GCA TTC TCT CCC TTC        184
 E   I   E   M   K   T   K   D   K   P   L   A   F   S   P   F
             35                  40                  45

CTG CTG TCC CAC TGC ATG GGT TAC GGG TTC TAC CAC TTC GCC AGC TTC        232
 L   L   S   H   C   M   G   Y   G   F   Y   H   F   A   S   F
         50                  55                  60

CCA AAG GGG ACT AAG AAC ATC TAT CTT CAT GCT GCA ACA AAC GGA GGT        280
 P   K   G   T   K   N   I   Y   L   H   A   A   T   N   G   G
 65                  70                  75                  80

TAC ACC AAC ACC AGG AAG GAG ATC TAT GAA GAC GGC GGC ATC TTG GAG        328
 Y   T   N   T   R   K   E   I   Y   E   D   G   G   I   L   E
                     85                  90                  95

GTC AAC TTC CGT TAC ACT TAC GAG TTC AAC AAG ATC ATC GGT GAC GTC        386
 V   N   F   R   Y   T   Y   E   F   N   K   I   I   G   D   V
                 100                 105                 110

GAG TGC ATT GGA CAT GGA TTC CCA AGT CAG AGT CCG ATC TTC AAG GAC        424
 E   C   I   G   H   G   F   P   S   Q   S   P   I   F   K   D
             115                 120                 125
```

-continued

```
ACG ATC GTG AAG TCG TGT CCC ACG GTG GAC CTG ATG TTG CCG ATG TCC    472
 T   I   V   K   S   C   P   T   V   D   L   M   L   P   M   S
    130                 135                 140

GGG AAC ATC ATC GCC AGC TCC TAC GCT AGA GCC TTC CAA CTG AAG GAC    520
 G   N   I   I   A   S   S   Y   A   R   A   F   Q   L   K   D
145                     150                 155                 160

GGC TCT TTC TAC ACG GCA GAA GTC AAG AAC AAC ATA GAC TTC AAG AAT    568
 G   S   F   Y   T   A   E   V   K   N   N   I   D   F   K   N
                165                 170                 175

CCA ATC CAC GAG TCC TTC TCG AAG TCG GGG CCC ATG TTC ACC CAC AGA    616
 P   I   H   E   S   F   S   K   S   G   P   M   F   T   H   R
            180                 185                 190

CGT GTC GAG GAG ACT CAC ACC AAG GAG AAC CTT GCC ATG GTG GAG TAC    664
 R   V   E   E   T   H   T   K   E   N   L   A   M   V   E   Y
        195                 200                 205

CAG CAG GTT TTC AAC AGC GCC CCA AGA GAC ATG TAG                    700
 Q   Q   V   F   N   S   A   P   R   D   M   *
    210                 215

AATGTGGAAC GAAACCTTTT TTTCTGATTA CTTTCTCTGT TGACTCCACA              750

TTCGGAACTT GTATAAATAA GTTCAGTTTA AA                                 782
```

This nucleotide sequence (SEQ ID NO: 3) is disclosed in the pamphlet of International Publication WO 2005/095599. A vector, pBluescript II SK-NFP, produced by inserting the gene encoding CpYGFP into the multicloning site of a cloning vector, pBluescript II SK, was subjected to international deposition under the Budapest Treaty with International Patent Organism Depositary in the National Institute of Advanced Industrial Science and Technology, an Independent Administrative Institution under the Ministry of Economy, Trade and Industry (the AIST Tsukuba Central 6, Higashi 1-1-1, Tsukuba, Ibaraki, Japan, postal code: 305-8566) under accession No. FERM BP-08681 (on Mar. 31, 2004).

On the other hand, the nucleotide sequence of a gene encoding ppluGFP2 from *Pontellina plutellina* has been published (Reference 9: SHAGIN et al., Mol. Biol. Evol., (2004), Vol. 21, No. 5, pp. 841-850). Specifically, the aforementioned nucleotide sequence was registered under GenBank accession No. AY268072. In addition, an expression vector (a product named as Cop-Green™) produced by inserting the gene encoding ppluGFP2 into a series of plasmids in a form capable of recombinant expression is commercially available from EVRQGEN. Into such a commercially available expression vector, DNA comprising a nucleotide sequence converted to the following humanized codon is inserted as a gene encoding ppluGFP2.

Sequence of the Humanized Version of the CopGFP's Open Reading Frame

```
                                                        (SEQ ID NO: 5)
ATG CCC GCC ATG AAG ATC GAG TGC CGC ATC ACC GGC ACC CTG AAC GGC     48
 M   P   A   M   K   I   E   C   R   I   T   G   T   L   N   G     16

GTG GAG TTC GAG CTG GTG GGC GGC GGA GAG GGC ACC CCC GAG CAG GGC     96
 V   E   F   E   L   V   G   G   G   E   G   T   P   E   Q   G     32

CGC ATG ACC AAC AAG ATG AAG AGC ACC AAG GGC GCC CTG ACC TTC AGC    144
 R   M   T   N   K   M   K   S   T   K   G   A   L   T   F   S     48

CCC TAC CTG CTG AGC CAC GTG ATG GGC TAC GGC TTC TAC CAC TTC GGC    192
 P   Y   L   L   S   H   V   M   G   Y   G   F   Y   H   F   G     64

ACC TAC CCC AGC GGC TAC GAG AAC CCC TTC CTG CAC GCC ATC AAC AAC    240
 T   Y   P   S   G   Y   E   N   P   F   L   H   A   I   N   N     80

GGC GGC TAC ACC AAC ACC CGC ATC GAG AAG TAC GAG GAC GGC GGC GTG    288
 G   G   Y   T   N   T   R   I   E   K   Y   E   D   G   G   V     96

CTG CAC GTG AGC TTC AGC TAC CGC TAC GAG GCC GGC CGC GTG ATC GGC    336
 L   H   V   S   F   S   Y   R   Y   E   A   G   R   V   I   G    112

GAC TTC AAG GTG GTG GGC ACC GGC TTC CCC GAG GAC AGC GTG ATC TTC    384
 D   F   K   V   V   G   T   G   F   P   E   D   S   V   I   F    128

ACC GAC AAG ATC ATC CGC AGC AAC GCC ACC GTG GAG CAC CTG CAC CCC    432
 T   D   K   I   I   R   S   N   A   T   V   E   H   L   H   P    144

ATG GGC GAT AAC GTG CTG GTG GGC AGC TTC GCC CGC ACC TTC AGC CTG    480
```

```
                              -continued
M    G    D    N    V    L    V    G    S    F    A    R    T    F    S    L         160

CGC  GAC  GGC  GGC  TAC  TAC  AGC  TTC  GTG  GTG  GAC  AGC  CAC  ATG  CAC  TTC        528
R    D    G    G    Y    Y    S    F    V    V    D    S    H    M    H    F         176

AAG  AGC  GCC  ATC  CAC  CCC  AGC  ATC  CTG  CAG  AAC  GGG  GGC  CCC  ATG  TTC        576
K    S    A    I    H    P    S    I    L    Q    N    G    G    P    M    F         192

GCC  TTC  CGC  CGC  GTG  GAG  GAG  CTG  CAC  AGC  AAC  ACC  GAG  CTG  GGC  ATC        624
A    F    R    R    V    E    E    L    H    S    N    T    E    L    G    I         208

GTG  GAG  TAC  CAG  CAC  GCC  TTC  AAG  ACC  CCG  ATC  GCA  TTC  GCC  TGA             669
V    E    Y    Q    H    A    F    K    T    P    I    A    F    A    *              223
```

In the modified fluorescent proteins produced by applying the methods of the first and second embodiments of the present invention, one to several specific amino acids are replaced with other amino acids in the amino acid sequence of the aforementioned wild-type fluorescent protein. Using available gene DNA comprising a known nucleotide sequence as a template, site-directed mutagenesis is carried out according to a method described in the exemplary embodiments below, so as to produce such a modified fluorescent protein in the form of a recombinant protein. In particular, such recombinant expression can be performed on all of such wild-type fluorescent proteins. Moreover, the modified site does not affect the protein folding. Thus, such a modified fluorescent protein can be produced in a host capable of recombinant expression of a wild-type fluorescent protein in the form of a mature fluorescent protein actually emitting fluorescence at the same efficiency as that of the wild-type fluorescent protein.

For example, modified fluorescent proteins produced by applying the methods of the first and second embodiments of the present invention to CpYGFP from *Chiridius poppei* can be recombinantly expressed as mature fluorescent proteins emitting fluorescence in human cells according to the method disclosed in the pamphlet of International Publication WO 2005/095599. Moreover, such mature fluorescent proteins can also be recombinantly expressed as fluorescent marker proteins or as fused proteins obtained by fusion with other proteins in host cells. The method applied at that time is substantially equivalent to the method disclosed in the pamphlet of International Publication WO 2005/095599.

EXEMPLARY EMBODIMENTS

The present invention will be specifically described in the following exemplary embodiments. The following exemplary embodiments are provided as several examples of the best embodiment of the present invention, and are not intended to limit the scope of the invention.

I. Determination of Three-Dimensional Structure of the GFP-Like Fluorescent Protein from *Chiridius poppei*, CpYGFP In order to determine the three-dimensional structure of the GFP-like fluorescent protein from *Chiridius poppei*, CpYGFP, crystallization was carried out using a purified sample of recombinant CpYGFP. The obtained crystals were used in X-ray crystal structure analysis.

(I-1) Preparation of Purified Sample of Recombinant CpYGFP

In accordance with the method disclosed in the pamphlet of International Publication WO 2005/095599, a gene encoding CpYGFP from *Chiridius poppei* was inserted into a commercially available plasmid, pET101/D-TOPO (manufactured by Invitrogen), so as to produce an expression vector, pET101-NFP, which was available for recombinant expression of the CpYGFP in *Escherichia coli*.

At that time, the gene encoding CpYGFP from *Chiridius poppei* was prepared by the PCR method using, as a template, the gene, which had already been cloned into pBluescript II SK-NFP (FERM BP-08681). It is to be noted that the vector, pBluescript II SK-NFP, produced by inserting the gene (cDNA) encoding CpYGFP into the multicloning site of a cloning vector, pBluescript II SK, was subjected to international deposition under the Budapest Treaty with in the National Institute of Advanced Industrial Science and Technology, an Independent Administrative Institution under the Ministry of Economy, Trade and Industry (the AIST Tsukuba Central 6, Higashi 1-1-1, Tsukuba, Ibaraki, Japan, postal code: 305-8566) under accession No. FERM BP-08681 (on Mar. 31, 2004).

Figure 7:
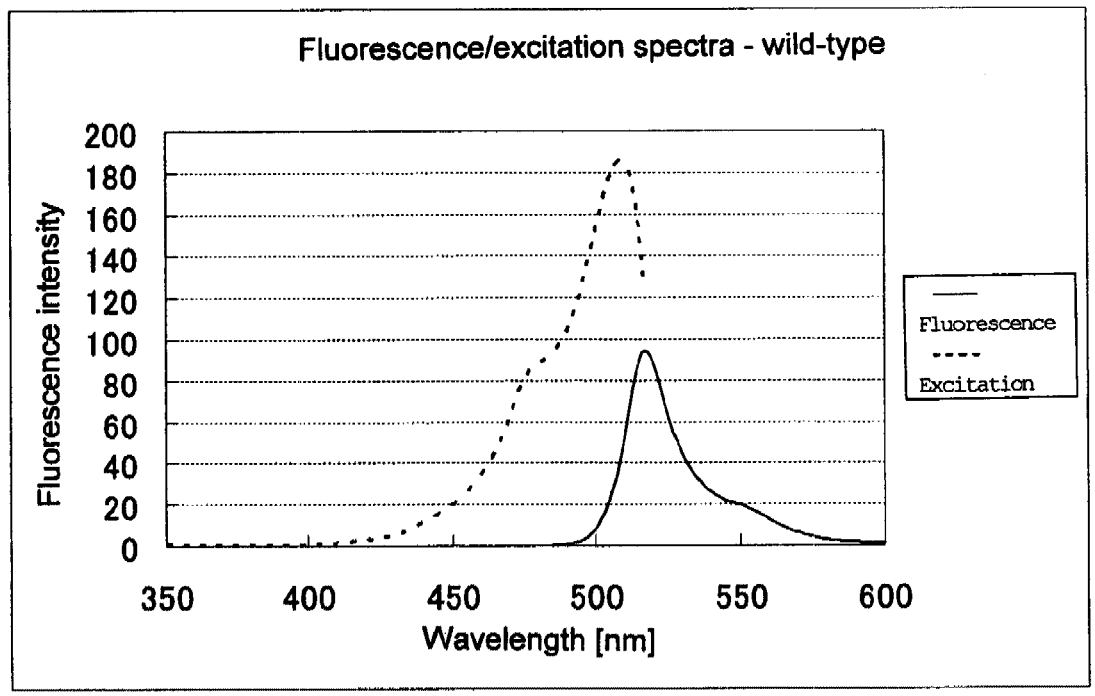

First, *Escherichia coli* was transformed, using pET101-NFP, a recombinant expression vector for the CpYGFP, as shown in FIG. 7. Thereafter, clone selection was performed on the transformed *Escherichia coli*, using an ampicillin resistance gene as a selective marker.

With regard to the selected clone, expression of the inserted gene was induced from a promoter originated from the vector, pET101/D-TOPO, using IPTG. Two and four hours after such induction, the presence or absence of recombinant expression of a fluorescent protein was confirmed. In addition, after completion of the expression induction by IPTG, based on the fact that a colony of the transformed strain exhibited fluorescence when ultraviolet ray was irradiated to the colony, it was confirmed that the recombinant fluorescent protein expressed therein had folded in the shape of a mature protein.

In accordance with the procedures and conditions disclosed in the pamphlet of International Publication WO 2005/095599, the transformed *Escherichia coli* retaining the recombinant expression vector pET101-NFP for CpYGFP from *Chiridius poppei* was cultured in a large scale, and the recombinant fluorescent protein produced as a result of the expression induction with IPTG was then separated and purified. The recombinant CpYGFP purified by such a separation and purification process was recovered, and it was then used as a purified sample protein in crystallization.

Subsequently, a solution that contained the recombinant CpYGFP purified to such an extent that it was observed as a single band in SDS-PAGE was concentrated to a protein concentration of 23 mg/ml by centrifugation.

(I-2) Crystallization

Crystallization was carried out by a sitting drop vapor diffusion method. 100 μl of a reservoir solution, and a mixture of 1 μl of a protein solution and 1 μl of a precipitant solution having the same composition as that of the reservoir solution used as a drop, were prepared. They were retained at 18° C. for approximately 1 week, so that the solvent (water) in the drop was reduced and the protein was concentrated, thereby causing precipitation of crystals.

In order to optimize crystallization conditions, the composition of the reservoir solution was variously changed. Among the thus prepared compositions, the composition of the reservoir solution that caused precipitation of crystals under the aforementioned conditions was selected. By this screening process, it was found that a columnar or block crystal with a size of 0.1 to 0.2 mm was precipitated, when 0.1 M CAPS (pH 10.5), 0.2 M $Li_2SO_4$, and 2.2 M $(NH_4)_2SO_4$ were used as the composition of the reservoir solution/the precipitant solution. The aforementioned crystal size is available for an X-ray diffractometer using synchrotron radiation, which is used as an X-ray light source as described below.

(I-3) X-Ray Crystal Structure Analysis

The symmetry and lattice constants of the crystal of the recombinant CpYGFP were determined. As a result, it was found that it has a space group was $C222_1$ with lattice constants of a=113.5 Å, b=133.5 Å, and c=108.7 Å.

X-ray diffraction intensity was measured using an X-ray diffractometer set up at the beamline BL-6A of Photon Factory at High Energy Accelerator Research Organization, KEK, Inter-university Collaborative Institute. The used X-ray light source (synchrotron radiation) had a wavelength λ=0.9799 Å. A CCD detector with the arrangement of two-dimensional matrix shape was employed for the measurement of the diffraction pattern and its intensity.

X-ray diffraction was measured in a state where the crystals were cooled to 100 K. A solution obtained by mixing glycerol and the reservoir solution used for the crystallization at a ratio of 3:7 (volume ratio) was used as a cryo-protectant. First, the crystal of protein was immersed in the cryo-protectant for approximately 10 seconds, so as to form a coated layer with the cryo-protectant on the surface of the crystal. Subsequently, the crystal of the protein being protected by the treatment was exposed to a stream of dry nitrogen, which had been adjusted to 100 K, so as to instantly freeze out the crystal. The frozen crystal, which was maintained in a state cooled with 100 K dry nitrogen, was subjected to the measurement of X-ray diffraction.

Programs, MOSFLM and SCALA (CCP4) were used in the data processing of the detected diffraction pattern and intensity data. Table 1 shows the statistical values of diffraction intensity data. The crystal had a space group: $C222_1$ with lattice constants: a=113.5 Å, b=133.5 Å, and c=108.7 Å; and the data with resolution of 1.9 Å were collected therefrom.

TABLE 1

Statistical values of diffraction intensity data

| | |
|---|---|
| Resolution range [Å] | 30-1.9 (2.00-1.90) |
| Nunber of measurements | 383411 (55090) |
| Number of reflections | 65109 (9438) |
| Completeness [%] | 99.9 (100.0) |
| Rmerge [%] | 0.073 (0.291) |
| I/σ (I) | 18.2 (5.2) |

In the crystal structure analysis of the recombinant CpYGFP based on the obtained diffraction intensity data, a molecular replacement method was applied using the coordinate data of DsRed that was assumed to have a similar structure to that of the CpYGFP, so as to determine an initial phase therefor. It is to be noted that the coordinate date of DsRed used as the model is published as ID 1GGX in the Protein Data Bank. In addition, program CNX was used to determine the protein molecule position by the molecular replacement method. A three-dimensional electron density map was produced based on the determined phase data. Thereafter, the program CNX and three-dimensional graphics software XtalView were used to refine the structural model.

In the crystal of the space group $C222_1$, it was confirmed that two protein molecules exist in each asymmetric unit, and that a dimeric form is formed with the proteins which have rotational symmetry as to each of the crystallographic 2-fold rotation axes, respectively. With regard to the atomic coordinate of the refined structural model, the statistical values thereof are summarized in Table 2.

TABLE 2

Statistical values of refined structural model

| | |
|---|---|
| Resolution range used [Å] | 30-1.90 |
| Number of reflections working (free) | 65081 (3281) |
| $R_{work}$ | 0.204 |
| $R_{free}$ | 0.231 |
| Number of protein atoms/A.U. | 3442 |
| Number of solvent atoms/A.U. | 451 |
| R.m.s. deviation in bond length [Å] | 0.0081 |
| R.m.s. deviation in bond angle [°] | 1.53 |
| Average B-factor [Å²] | 9.9 |
| B-factor on Wilson plot [Å²] | 23.2 |

Figure 3:
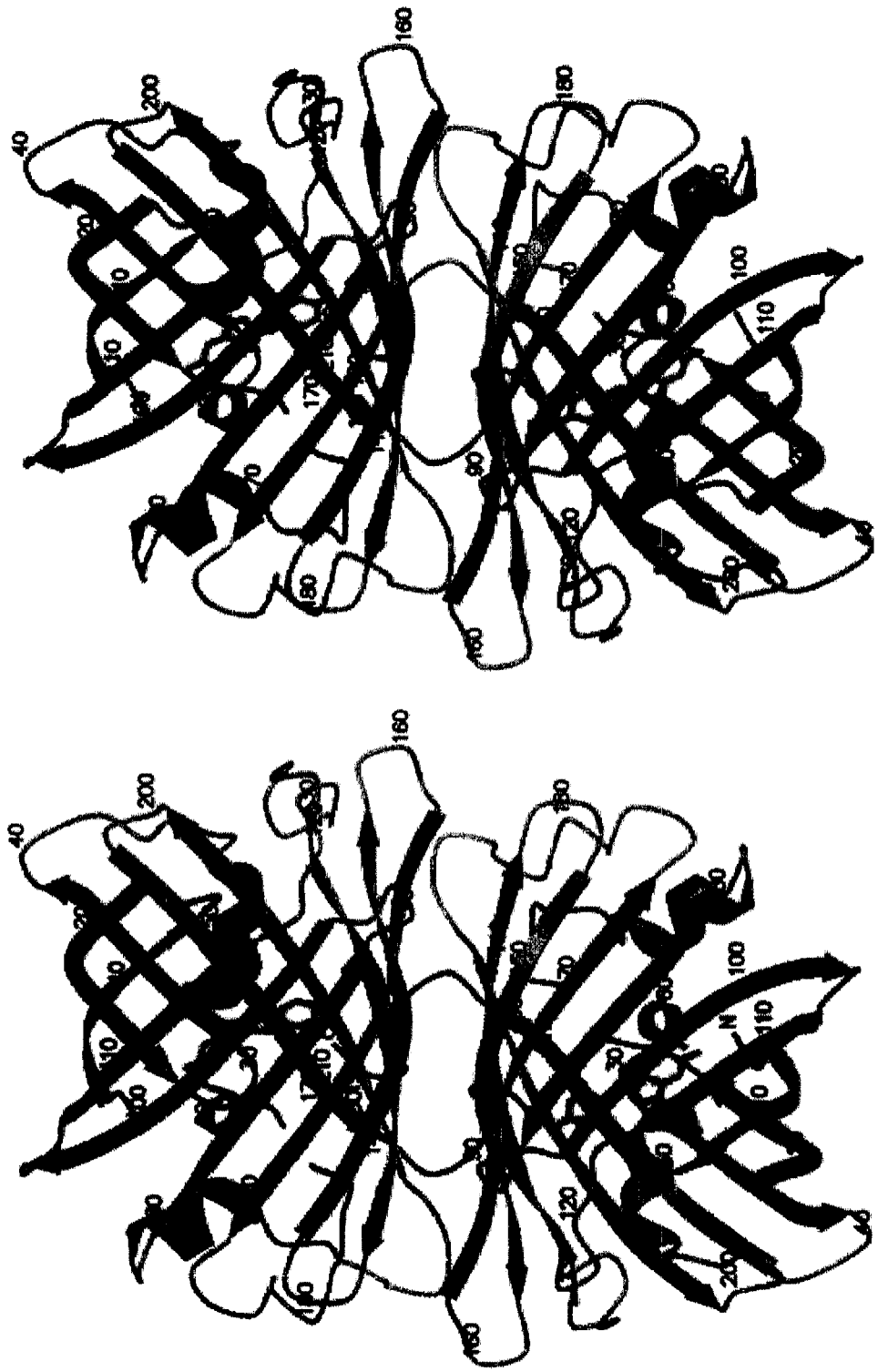
FIG. 3 is a view showing the crystal structure of the GFP-like fluorescent protein from *Chiridius poppei*, CpYGFP, which is a stereoscopic view illustrated in the form of a ribbon model, the entire structure of CpYGFP existing as a dimmer in the unit cell of a crystal.

FIG. 3 shows the three-dimensional structure of a peptide main chain in said refined structural model in the form of a ribbon model. The p-hydroxybenzylideneimidazolinone structure of a fluorescent moiety is shown in detail. In particular, FIG. 4 shows a local structure including the p-hydroxybenzylideneimidazolinone structure of the fluorescent moiety and the configuration of amino acid residues located around the aforementioned fluorescent moiety. The fluorescent moiety of the recombinant CpYGFP, namely, the detailed coordinate data of the crystal structure as shown in FIG. 3, has been registered as ID code of 2DD7 in the Protein Data Bank. Based on such a coordinate data, the crystal structure is expressed as a three-dimensional graphics, so that not only the entire image as shown in FIG. 3, but also the partial structure as shown in FIG. 4 can be referred more in detail.

In addition, with regard to the after-mentioned modified protein H52D as well, the detailed coordinate data of the equally-refined crystal structure has been registered as ID code of 2DD9 in the Protein Data Bank.

As shown in FIG. 4, the imidazole ring on the side chain of His[52] was overlapped with a p-hydroxyphenyl group (phenol ring) derived from the side chain of Tyr[56] in the p-hydroxybenzylideneimidazolinone structure of a fluorescent moiety formed from GYG. That is to say, the p-hydroxyphenyl group (phenol ring) and the imidazole ring adapted a relative configuration capable of interaction (π-π-stacking) with each other via their overlapped π-electrons.

Moreover, the hydroxyl group (—OH; phenolic hydroxyl group) of the hydroxyphenyl group (phenol ring) was adjacent to the hydroxyl group (—OH; alcoholic hydroxyl group) on the side chain of Thr[136], and thus the distance between them was short enough to form a hydrogen bond. Furthermore, water molecules existed at a position capable of forming a hydrogen bond with respect to the hydroxyl group of the hydroxyphenyl group (phenol ring).

On the other hand, the oxo-oxygen (=O) of the imidazolinone ring was adjacent to the amino nitrogen atom of the guanidyl group on the side chain of Arg[85], and thus the distance between them was short enough to form a hydrogen bond. Furthermore, water molecules existed at a position capable of forming a hydrogen bond with respect to the oxo-oxygen (=O) of the imidazolinone ring.

The aforementioned possible interaction (hydrogen bond) suggested that the hydroxyl group on the side chain of Thr[135] and the amino nitrogen atom of the guanidyl group on the side chain of Arg$^{85}$ played important roles in the following equilibrium between the ionized form and the neutral form, wherein the p-hydroxybenzylideneimidazolinone structure of a fluorescent moiety is stabilized in the ionized form.

Equilibrium between the ionized form and the neutral form in p-hydroxybenzylideneimidazolinone structure derived from "XYG," a cyclic structure is formed between >C=O at the C-terminus of X(Gly$^{55}$) and —NH— of the N-terminus of Gly$^{57}$ due to cyclization and dehydration. Thus, the dihedral angle (φ,ψ) of the peptide main chain in this region differs from the dihedral angle (φ,ψ) of the α helix. That is to say, as described below, the site of G$^{55}$Y$^{56}$G$^{57}$

[Chemical formula 8]

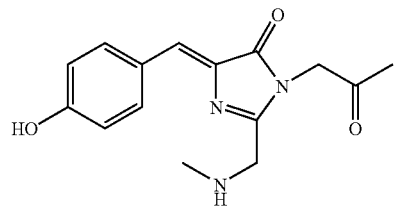 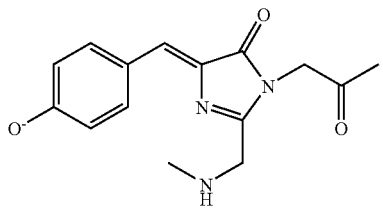

neutral form                  ionized form

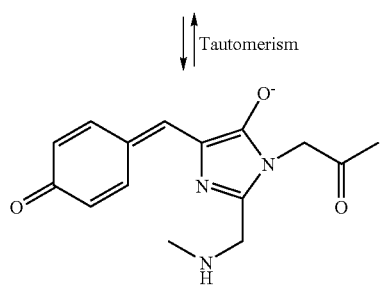

The analyzed crystal structure of the recombinant CpYGFP adopted a "β can" structure, wherein 11 β strands constituted a barrel form, and an α helix was disposed by penetrating from the upper portion to the lower portion of the center portion of the barrel form. This "βscan" structure was commonly found in DsRed used as a model for the molecular replacement method and in GFP from *Aequorea victoria* (hereinafter abbreviated as aqGFP). With regard to a fluorescent moiety, "GYG" was used as "XYG," and a p-hydroxybenzylideneimidazolinone structure was indeed autocatalytically formed therefrom. In the aqGFP, it was assumed that the "X$^{65}$Y$^{66}$G$^{67}$" initially formed a secondary structure corresponding to the α helix, and that after protein folding, Arg$^{96}$ contained in a β$_4$ strand and Glu$^{222}$ contained in a β$_{11}$ strand are involved in a cyclization process. Similarly, even in the recombinant CpYGFP, Arg$^{85}$ contained in a β$_4$ strand and Glu$^{207}$ contained in a β$_{11}$ strand are located close to a fluorescent moiety.

When the aforementioned cyclization process progresses, among hydrogen bonds formed between —NH— at position α of an n$^{th}$ number of amino acid residue and >C=O at the C-terminus of an (n–4)$^{th}$ number of amino acid residue, a hydrogen bond in a chain associated with the site of G$^{55}$Y$^{56}$G$^{57}$ is lost.

A winding of the α helix having a common secondary structure, which is found in proteins, consists of 3.6 amino acid residues, and during such a single winding, a helix goes ahead for 5.6 Å. In addition, since a hydrogen bond is formed between —NH— at position α of the n$^{th}$ number of amino acid residue and >C=O at the C-terminus of the (n–4)$^{th}$ number of amino acid residue, there are no cases where the side chain of the n$^{th}$ number of amino acid residue is overlapped with the side chain of the (n–4)$^{th}$ number of amino acid residue. On the other hand, in a fluorescent moiety region transitions to a "distorted configuration," wherein >C=O at the C-terminus of Gly$^{55}$ is adjacent to —NH— at position α of Gly$^{57}$.

Folding after translation (transition to distorted configuration)

[Chemical formula 9]

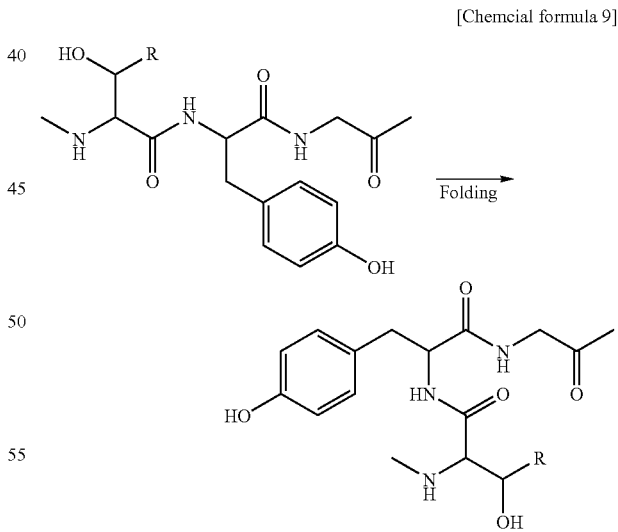

It is assumed that, together with this structural change, the imidazole ring on the side chain of His$^{52}$ can be overlapped with the p-hydroxyphenyl group (phenol ring) on the side chain of Tyr$^{56}$. Finally, after completion of the cyclization and dehydration reaction, >C=O at the C-terminus of His$^{52}$ and >C=O at the C-terminus of Tyr$^{56}$ become adjacent to the guanidino group on the side chain of Arg$^{85}$ contained in a β$_4$ strand, whereas —NH— at the N-terminus of Tyr$^{56}$ becomes adjacent to the carboxyl group on the side chain of Glu[207] in a $\beta_{11}$ strand. In this configuration, the imidazole ring on the side chain of His[52] can be overlapped with the p-hydroxyphenyl group (phenol ring) on the side chain of Tyr[56] at an interval between the two rings of approximately 3 Å. If adapting such a configuration wherein such types of aromatic rings are laminated in parallel, a structurally stable state, referred to as "π-π-stacking," is obtained. At that time, an interaction is generated between two π-electron conjugated systems.

II. Production of Modified Proteins

If the aforementioned "π-π-stacking" is achieved, an interaction is generated between two π-electron conjugated systems. As a result, both the peak wavelength (fluorescence wavelength) of the fluorescence of the p-hydroxybenzylideneimidazolinone structure of a fluorescent moiety, and the peak wavelength observed on an excitation spectrum, are shifted to the longer wavelength side, when compared with that of a case where such "π-π-stacking" is not achieved. In reality, three types of modified proteins, namely, a modified form (H53T) obtained by replacing His, an amino acid residue at position 52, with Thr, a modified form (H52F) obtained by replacing His with Phe, and a modified form (H52D) obtained by replacing His with Asp, were produced by recombinant expression. Thereafter, in terms of fluorescent properties, a comparison was made among such modified forms.

(II-1) Construction of Recombinant Expression Vector for Modified Proteins

A gene encoding wild-type CpYGFP inserted into a recombinant expression vector, pET101-NFP for CpYGFP from *Chiridius poppei*, disclosed in the pamphlet of International Publication WO 2005/095599, was used as a template. Genes encoding the three types of modified proteins, H53T, H52F, and H52D, were prepared by site-directed mutagenesis.

In order to replace a codon CAC encoding His[52] with each of a codon GAT encoding Asp, a codon ACC encoding Thr, and a codon TTC encoding Phe, the following primers were used to produce DNA fragments by the PCR method. That is to say, as forward primers for PCR, the three types of primers as indicated below, the 5'-termini of which were replaced with the aforementioned codons, were used. On the other hand, as reverse primers, a primer comprising a nucleotide sequence complementary to the partial nucleotide sequence (nucleotides 125-153; the following partial sequence) on the side upstream of the codon CAC encoding His[52] was used.

```
                                              (SEQ ID NO: 21)
5'- A CTG GCA TTC TCT CCC TTC CTG CTG TCC -3'

3'- T GAC CGT AAG AGA GGG AAG GAC GAC AGG -5'

Leu Ala Phe Ser Pro Phe Leu Leu Ser
         45                  50
```

Specifically, as such forward primers for PCR, the following three types of primers were respectively used:
for the point mutation of H52D,
CpYGFP/H52D UP (30 mer):

```
                                              (SEQ ID NO: 20)
5'- GAT TGC ATG GGT TAC GGG TTC TAC CAC TTC -3'
``` for the point mutation of H52T,
CpYGFP/H52T UP (30 mer):

```
                                              (SEQ ID NO: 19)
5'- ACC TGC ATG GGT TAC GGG TTC TAC CAC TTC -3'
``` for the point mutation of H52F,
CpYGFP/H52F UP (30 mer):

```
                                              (SEQ ID NO: 18)
5'- TTC TGC ATG GGT TAC GGG TTC TAC CAC TTC -3';
```

On the other hand, as a common reverse primer,
a reverse primer: CpYGFP/LP153 (28 mer) was used.

```
                                              (SEQ ID NO: 21)
5'-GGA CAG CAG GAA GGG AGA GAA TGC CAG T-3'
```

Using the recombinant expression vector pET101-NFP for CpYGFP as a template, a PCR amplified product of approximately 6.4 kbp corresponding to the entire length of the plasmid was prepared under the following conditions. Table 3 shows the temperature conditions applied to the PCR reaction, and Table 4 shows the composition of a reaction solution. Taking into consideration the point that the nucleotide length to be extended was long (approximately 6.4 kbp), a sufficiently long time was selected as an extension time.

TABLE 3

Temperature conditions for PCR reaction:
Apparatus used: Mastercycler Gradient (Eppendorf)

| Cycle operation | Temperature (° C.) | Time | |
|---|---|---|---|
| denature | 96 | 1 min | |
| anneal | 60 | 5 sec | |
| extention | 68 | 6 min 30 sec | 15 times |
| denature | 96 | 5 sec | |
| extention | 68 | 6 min 30 sec | |
| store | 10 | Overnight (14 hrs) | |

TABLE 4

Composition of reaction solution

| Component | Concentration of stock solution | Mixed amount (μL) | Final concentration |
|---|---|---|---|
| H$_2$O | | 48.75 | |
| Pyro Buffer | 10× | 7.5 | 1× |
| dNTP | 2 mM | 7.5 | 0.2 mM |
| Pyrobest DNA Pol. | 5 u/μL | 0.75 | 0.05 u/μL |
| Forward primer | 10 μM | 1.5 | 0.2 μM |
| CpYGFP/LP153 | 10 μM | 1.5 | 0.2 μM |
| Template plasmid | 1 μg/μL | 7.5 | 1 ng/μL |
| Total | | 75.0 | |

The prepared PCR amplified product was purified by the following procedures.

A PCR reaction was carried out using 25 μL each of a reaction solution. Thereafter, the total 3 reaction solutions were gathered, and 5 μL of a reaction solution was collected. The obtained reaction solution was electrophoresed on 0.7% agarose gel. As a result, a PCR amplified product with a molecular weight of interest of approximately 6.4 kbp was confirmed.

Subsequently, a DNA product was concentrated from the reaction solution using MinElute PCR Purification Kit (manufactured by QIAGEN). 5 volumes (350 μL) of PB buffer were added to 1 volume (70 μL) of the reaction solution. The thus obtained mixture was subjected to vortex, and it was then transferred to a MinElute column. The mixture was centrifuged for 30 seconds. The precipitated DNA was sedimented, and a supernatant was eliminated. The precipitated DNA was washed with 0.7 mL of PE buffer, and it was then centrifuged (15,000 rpm) for 1 minute. Thereafter, 20 μL of EB buffer was added to the resultant, and the obtained mixture was then left at rest at a room temperature for 1 minute. Thereafter, the reaction product was centrifuged (15,000 rpm) for 1 minute, and a supernatant was then recovered.

3 μL of 10× Buffer (500 mM Tris/HCl (pH 9.5), 100 mM MgCl$_2$, 50 mM DTT), 3 μL of 50% glycerol, and 3 μL of 75 mM ATP were added to the recovered DNA solution, and the obtained mixture was subjected to vortex. Thereafter, 1 μL of T4 PNK (Polynucleotide kinase) was added to the resultant, and the obtained mixture was then incubated at 37° C. for approximately 30 minutes.

After 3 μL of 10× loading dye solution had been added to the resultant, 33 μL of the DNA solution in each lane was electrophoresed on 0.7% TAE agarose gel. A band of interest with a size of approximately 6.4 kbp was cut out of the gel. The cut gel section was centrifuged (7,000 rpm) for 10 minutes using Ultrafree-DA (manufactured by MILLIPORE), so that a DNA solution was extracted from the gel section and it was collected in a 1.5-mL eppen tube. From the extract, the DNA product was concentrated using MinElute PCR Purification Kit (manufactured by QIAGEN). 5 volumes of PB buffer were added to 1 volume of the reaction solution. The thus obtained mixture was subjected to vortex, and it was then transferred to a MinElute column. The mixture was centrifuged for 30 seconds. The precipitated DNA was sedimented, and a supernatant was eliminated. The precipitated DNA was washed with 0.7 mL of PE buffer, and it was then centrifuged (15,000 rpm) for 1 minute. Thereafter, 10 μL of EB buffer was further added to the resultant, and the obtained mixture was then left at rest at a room temperature for 1 minute. Thereafter, the reaction product was centrifuged (15,000 rpm) for 1 minute, and a supernatant was then recovered. The recovered supernatant was used as a solution containing purified double-stranded DNA.

1 μL of the purified double-stranded DNA solution was mixed with 1 μL of Ligation high (manufactured by Toyobo), and a ligation reaction was then carried out at 16° C. overnight. As a result of the ligation reaction, both ends of the double-stranded DNA were ligated, so as to construct a cyclic plasmid. Each plasmid had the same structure as that of the recombinant expression vector pET101-NFP for CpYGFP used as a template, except for the introduced point mutation. Thus, this acted as a recombinant expression vector for each modified protein.

After completion of the ligation, the total amount of ligation solution (2 μL) was transformed to TOP10 cell, and it was then inoculated on an LB plate containing Carbenicillin. The next morning, several colonies comprising genes resistant to the aforementioned agent, which existed in the plasmid vector, were collected. The thus collected colonies were inoculated into an LB medium containing Carbenicillin, so that the transformed Escherichia coli was allowed to proliferate, thereby proliferating the plasmid vector. The collected transformed Escherichia coli was disintegrated, and DNA was then recovered therefrom. A cyclic DNA molecule (plasmid vector) having a molecular weight of interest of approximately 6.4 kbp was isolated and purified.

In order to confirm the nucleotide sequence of a gene encoding each modified protein, which was contained in each of the purified plasmid vectors, a region encoding a modified protein contained in the aforementioned plasmid vector was used as a template, and a DNA fragment was amplified by PCR, so as to produce a sample used for sequencing.

As primers used in the PCR at that time, the following forward primer pET-UP1 (28 mer):

5'-CACCATGACAACCTTCAAAATCGAGTCC-3' (SEQ ID NO: 28)

and the following reverse primer SalI-LP1 (35 mer):

(SEQ ID NO: 29)
5'-CTCGTCGACCTACATGTCTCTTGGGGCGCTGTTGA-3' were used. These primers are disclosed in the pamphlet of International Publication WO 2005/095599. Using the aforementioned primers, the amplified product with a nucleotide length of 673 bp was prepared.

The sample used for sequencing, prepared from the 673-bp DNA fragment, was subjected to a commercially available sequencing apparatus, ABI PRISM 310 Genetic Analyzer, so that both sequencing from the 5'-terminal side and sequencing from the 3'-terminal side were conducted.

The results of the sequence analysis from the 5'-terminal side were put together with the results of the sequence analysis from the 3'-terminal side. Thereafter, it was confirmed that site-directed mutagenesis of interest had been introduced into the nucleotide sequence of the region encoding such a modified protein, and that the aforementioned nucleotide sequence did not comprise errors made during the PCR amplification.

(II-2) Recombinant Expression of Modified Proteins

Using the recombinant expression vector pET101-CpYGFP-H53T for the H53T modified protein, the recombinant expression vector pET101-CpYGFP-H52F for the H52F modified protein, and the recombinant expression vector pET101-CpYGFP-H52D for the H52D modified protein, all of which had been prepared and purified by the aforementioned procedures, modified proteins were produced by the following procedures.

First, using the vector for the recombinant expression of each modified protein, Escherichia coli BL21-CodonPlus™ (DE3)-RIL Competent Cells (manufactured by Staratagene) was transformed. The transformed Escherichia coli, into which the expression vector of interest had been introduced, was selected using a drug resistance gene originated from the vector pET101/D-TOPO.

The thus selected transformed Escherichia coli was pre-cultured at 37° C. in a liquid medium, to which an agent, Carbenicillin, had been added, until OD$_{600}$ indicating a cell mass density in the medium reached 0.6. When such OD$_{600}$ reached 0.6, IPTG was added to the medium at the final concentration of 1 mM, and the culture temperature was then decreased. The culture was further continued. That is to say, using IPTG, expression of a gene encoding each modified protein was induced from a promoter originated from the vector pET101/D-TOPO. After completion of the expression induction by IPTG, the H52T modified protein was cultured at 25° C. for 20 hours, the H52D modified protein was cultured at 30° C. for 16 hours, and the H52F modified protein was cultured at 30° C. for 16 hours. After completion of such culture, the culture was terminated, and cells were then collected by centrifugation. The collected cell mass was washed with 20 mM Tris-HCl (pH 8.5), and it was then frozen at −80° C. for preservation.

Each of the frozen transformed *Escherichia coli* was thawed, and it was then suspended in 20 mM Tris-HCl (pH 8.0), followed by ultrasonic disintegration. After completion of the disintegration of the cell mass, it was centrifuged at 10,000×g, and a supernatant containing a soluble fraction was fractionated. As a result of SDS-PAGE analysis, a new band of 25 kDa, which corresponded to the molecular weight of the modified protein of interest, was found in the aforementioned supernatant.

Each modified protein contained in the aforementioned supernatant was purified in the following three-stage purification processes, in accordance with the procedures for purifying the recombinant CpYGFP disclosed in International Publication WO 2005/095599, using a HiTrap-DEAE column (Amersham Biosciences), a HiTrap-phenyl column (Amersham Biosciences), and a gel filtration column Superdex 75 (Amersham Biosciences).

Step 1:
A supernatant containing each modified protein was subjected to an anion exchange column HiTrap DEAE (manufactured by Amersham Biosciences), and the aforementioned modified protein was then recovered in 1%-5% B buffer fraction under elution conditions (A buffer: 20 mM Tris-HCl, pH 8.5; B buffer: 1 M NaCl in A buffer; linear gradient 0%-15% B buffer (0-150 mM NaCl concentration)).

Step 2:
Subsequently, the recovered fraction was subjected to an affinity column HiTrap-phenyl column (Amersham Biosciences), and the three above types of modified proteins were then recovered in 65% B-38% B (H52T), 62% B-0% B (H52F), and 46% B-0% B (H52D) fractions under elution conditions (A buffer: 50 mM Tris-HCl, pH 8.0; B buffer: 0.7 M $Na_2SO_4$ in A buffer; linear gradient 100%-0% B buffer (0.7 M-0 M $Na_2SO_4$ concentration)).

Step 3:
Further, each of the recovered fractions was previously subjected to centrifugal concentration under conditions of VIVASPIN20 and MW of 10,000 cut. The concentrated sample was subjected to gel filtration using Superdex 75 (manufactured by Amersham Biosciences), so that the modified protein was purified and then recovered in the form of a fraction exhibiting absorption at a wavelength of 490 nm under elution conditions (buffer: 20 mM Tris-HCl, pH 8.0, 0.2 M NaCl). Thereafter, the protein contained in the recovered fraction was subjected to SDS analysis. As a result, it was confirmed that only a protein exhibiting a band of a molecular weight of approximately 24-25 kDa on the SDS electrophoresis was contained therein.

It was confirmed that all these solution samples of the purified modified proteins emitted a yellow-green fluorescence under irradiation of a Dark Reader light (wavelength range: 420 nm to 500 nm).

(II-3) Fluorescent Properties of Recombinant Modified Proteins

A solution sample dissolved in 25 mM Tris-HCl (pH 8.0) and 0.1 M NaCl was used to measure the fluorescence spectrum and excitation spectrum of a purified modified protein. For comparison, the fluorescence spectrum and excitation spectrum of wild-type CpYGFP were also measured using a solution sample dissolved in the aforementioned buffer solution. The fluorescence spectrum was measured at a room temperature (25° C.) using a fluorescence measurement apparatus F-4500 manufactured by HITACHI. On the other hand, the excitation spectrum was measured by monitoring the fluorescence intensity in the maximum peak wavelength of the fluorescence spectrum.

The fluorescence spectrum and excitation spectrum of the wild-type CpYGFP, H52T modified protein, H52D modified protein, and H52F modified protein are shown in FIGS. 7-1 and 7-2. The maximum peak wavelength ($\lambda_{em.max}$) on the fluorescence spectrum and the peak wavelength ($\lambda_{ex.peak}$) on the excitation spectrum are shown in Table 5.

TABLE 5

Maximum peak wavelength on fluorescence spectrum and peak wavelength on excitation spectrum

|  | $\lambda_{em.MAX}$ (nm) | $\lambda_{ex.peak}$ (nm) |
|---|---|---|
| Wild type | 517.0 | 509.0 |
| H52T | 511.2 | 495.4 |
| H52F | 521.8 | 513.6 |
| H52D | 511.0 | 499.2 & 408.2 |

When compared with the fluorescence spectrum of the wild-type CpYGFP, the fluorescence spectrum of the H52T modified protein wherein $His^{52}$ was replaced with Thr was blue-shifted. Likewise, the peak on the excitation spectrum was also blue-shifted. These results demonstrated that, in the case of the fluorescent moiety of the wild-type CpYGFP, the imidazole ring on the side chain of $His^{52}$ was overlapped with a p-hydroxyphenyl group (phenol ring) derived from the side chain of $Tyr^{56}$ in the p-hydroxybenzylideneimidazolinone structure, and thus that the "π-π-stacking" was actually achieved and the interaction between two π-electron conjugated systems was thereby generated.

Similarly, the aforementioned "π-π-stacking" did not contribute to the fluorescence spectrum of the H52D modified protein wherein $His^{52}$ was replaced with Asp, and thus the aforementioned fluorescence spectrum was also blue-shifted, when compared with the wild-type CpYGFP. In addition, two peaks were observed on the excitation spectrum of the H52D modified protein. It was considered that the peak at a wavelength of 499.2 nm corresponded to absorption caused by a fluorescent moiety exhibiting an ionized form. On the other hand, it was considered that the peak at a wavelength of 408.2 nm corresponded to absorption caused by a fluorescent moiety exhibiting a neutral form. That is to say, since Asp having ability to donate protons was located close to the p-hydroxyphenyl group (phenol ring) derived from the side chain of $Tyr^{56}$, the ionization ratio of the phenolic hydroxyl group of the aforementioned p-hydroxyphenyl group decreased. As a result, it was considered that the peak corresponding to the absorption caused by the fluorescent moiety exhibiting a neutral form was observed on the excitation spectrum.

On the other hand, when compared with the fluorescence spectrum of the wild-type CpYGFP, the fluorescence spectrum of the H52F modified protein wherein $His^{52}$ was replaced with Phe was red-shifted. Likewise, the peak on the excitation spectrum was also red-shifted. These results suggested that, in the case of the fluorescent moiety of the wild-type CpYGFP, the benzene ring on the side chain of Phe was actually overlapped with a p-hydroxyphenyl group (phenol ring) derived from the side chain of $Tyr^{56}$ in the p-hydroxybenzylideneimidazolinone structure, and thus that the "π-π-stacking" was achieved and the interaction between two π-electron conjugated systems was thereby generated.

From the above results, when $His^{52}$ was replaced with Phe, Tyr, or Trp having a benzene ring, a hydroxyphenyl group (phenol ring), or an indole ring, which enabled the "π-π-stacking" and had a wider π-electron conjugated system than that of the imidazole ring on the side chain of $His^{52}$, it was predicted that the fluorescence of the obtained modified form, namely, an H52F, H52Y, or H52W modified form, exhibited the same level of peak wavelength, or was red-shifted, when compared with the fluorescence of the wild-type CpYGFP.

On the other hand, when His$^{52}$ was replaced with Ala (side chain: CH$_3$—), Val (side chain: CH$_3$—CH(CH$_3$)—), Ile (side chain: C$_2$H$_5$—CH(CH$_3$)—), Leu (side chain: CH$_3$—CH(CH$_3$)—CH$_2$—), Gly (no side chain), cysteine (side chain: HS—CH$_2$—), methionine (CH$_3$—S—C$_2$H$_4$—), serine (side chain: HO—CH$_2$—), or threonine (side chain: CH$_3$—CH(OH)—), which did not cause the "π-π-stacking," it was predicted that the fluorescence of such a modified form was blue-shifted, when compared with the fluorescence of the wild-type CpYGFP.

Moreover, when His$^{52}$ was replaced with Asp (side chain: —CH$_2$—COOH) or Glu (side chain: —CH$_2$—CH$_2$—COOH), which did not cause the "π-π-stacking" and had a carboxyl group having ability to donate a proton on the side chain, it was predicted that the fluorescence of such a modified form was blue-shifted, when compared with the fluorescence of the wild-type CpYGFP. Furthermore, when His$^{52}$ was replaced with Asn (side chain: —CH$_2$—CO—NH$_2$) or Gln (side chain: —CH$_2$—CH$_2$—CO—NH$_2$), which did not cause the "π-π-stacking," it was predicted that the fluorescence of such a modified form was blue-shifted, when compared with the fluorescence of the wild-type CpYGFP.

III. Production of Modified Protein, into Fluorescent Moiety of which Mutation has been Introduced With regard to the aforementioned fluorescent moiety, His$^{52}$ causing the "π-π-stacking" was replaced with another amino acid residue, and at the same time, Tyr$^{56}$ in "GYG" forming the fluorescent moiety was replaced with Trp, so as to produce a modified protein, thereby obtaining very interesting results.

Specifically, a modified protein produced by replacing Tyr$^{56}$ in "GYG" forming the fluorescent moiety of the wild-type CpYGFP with Trp corresponded to CFP produced by replacing Tyr$^{66}$ in "SYG" forming the fluorescent moiety of the aforementioned aqGFP with Trp. The fluorescence spectrum showed a form wherein two fluorescence peaks having a small energy difference were overlapped with each other, and it was predicted that such two peaks having a small energy difference would also be overlapped with each other on the corresponding excitation spectrum. However, when such a modified protein was actually produced by replacing the "GYG" forming the fluorescent moiety of the wild-type CpYGFP with "GWG" and its fluorescence spectrum and excitation spectrum were measured, it was unexpectedly found that a single peak was shown in both spectra.

(III-1) Construction of Recombinant Expression Vector for Modified Protein, into Fluorescent Moiety of which Mutation has been Introduced A gene encoding the wild-type CpYGFP inserted into the recombinant expression vector pET101-NFP for CpYGFP from *Chiridius poppei*, disclosed in the pamphlet of International Publication WO 2005/095599, was used as a template. Using such a template, a gene encoding a modified protein wherein "GYG" forming the fluorescent moiety was replaced with "GWG" was prepared by site-directed mutagenesis.

Specifically, genes encoding total three types of modified proteins, namely, a Y56W modified protein produced by replacing Tyr$^{56}$ with Trp, a Y56W, V194S modified protein produced by replacing Val$^{194}$ with Ser in addition to the aforementioned substitution, and a Y56W, V194S, T136A modified protein produced by replacing Thr$^{136}$ with Ala, were successively prepared.

(a) Construction of Recombinant Expression Vector for the Y56W Modified Protein

In order to replace a codon TAC encoding Yyr$^{56}$ with a codon TGG encoding Trp, a DNA fragment was produced by the PCR method using the primers indicated below. That is to say, as a PCR forward primer, the following primer, the 5'-terminus of which had been replaced with the aforementioned codon, was used.

As such a PCR forward primer,
for point mutation of Y56W,
CpYGFP/Y56W UP (27 mer):

(SEQ ID NO: 22)
5'-<u>TGG</u> GGG TTC TAC CAC TTC GCC AGC TTC -3'

On the other hand, as a reverse primer, a primer comprising a nucleotide sequence complementary to a partial nucleotide sequence (nucleotides 135-165; the following partial sequence) located on the side upstream of a codon TAC encoding Tyr$^{56}$ was used.

5'-C TCT CCC TTC CTG CTG TCC CAC TGC ATG GGT-3'

(SEQ ID NO: 23)
3'-G AGA GGG AAG GAC GAC AGG GTG ACG TAC CCA-5'

Ser Pro Phe Leu Leu Ser His Cys Met Gly
50                                    55

That is to say, as a PCR reverse primer, CpYGFP LP165 (31 mer) comprising the following nucleotide sequence was used.

(SEQ ID NO: 23)
5'-ACC CAT GCA GTG GGA CAG CAG GAA GGG AGA G-3'

Using the recombinant expression vector pET101-NFP for CpYGFP as a template, a PCR amplified product with a size of approximately 6.4 kbp that corresponded to the entire length of the aforementioned plasmid was prepared under the conditions described in (II-1) above. In addition, the following steps, which were performed after completion of the PCR amplification, were also carried out in accordance with the conditions and procedures described in (II-1) above:

purification of the prepared PCR amplified product;

production of a cyclic plasmid from the purified PCR amplified product of approximately 6.4 kbp via a ligation reaction;

transformation of TOP10 cell and amplification of the plasmid by culture; and the recovery of the amplified plasmid, and the sequencing of the nucleotide sequence of its protein coding region.

A recombinant expression vector pET101-CpYGFP-Y56W for the Y56W modified protein was prepared and was then purified by the aforementioned procedures.

(b) Construction of Recombinant Expression Vector for the Y56W, V194S Modified Protein In order to replace a codon GTC encoding VAl$^{194}$ with a codon AGC encoding Ser as well as the aforementioned substitution of Tyr$^{56}$ with Trp, a DNA fragment was produced by the PCR method using the primers indicated below. That is to say, as a PCR reverse primer, the following primer, to the complementary nucleotide sequence of which the aforementioned codon substitution had been performed, was used.

For point mutation of V194S,
as a PCR reverse primer,
CpYGFP V194S LP (25 mer):

(SEQ ID NO: 25)
5'-C CTC G<u>CT</u> ACG TCT GTG GGT GAA CAT-3' was used. When translation was performed using the complementary strand thereof, the following replacement of amino acid residues was carried out.

5' ATG TTC ACC CAC AGA CGT AGC GAG G-3'

(SEQ ID NO: 25)
3'-TAC AAG TGG GTG TCT GCA <u>TC</u>G CTC C-5'

Met Phe Thr His Arg Arg Ser Glu
190                          195

On the other hand, as a forward primer,
CpYGFP UP587 (28 mer):

(SEQ ID NO: 24)
5'-AG ACT CAC ACC AAG GAG AAC CTT GCC AT-3'

Glu Thr His Thr Lys Glu Asn Leu Ala Met
200                                 205 was used, and a primer comprising a nucleotide sequence corresponding to a partial nucleotide sequence (a portion ranging from nucleotides 587 to 614) located on the side immediately downstream of the codon GTC encoding Val[194] was used.

Using the recombinant expression vector pET101-CpYGFP-Y56W for the Y56W modified protein as a template, a PCR amplified product with a size of approximately 6.4 kbp that corresponded to the entire length of the aforementioned plasmid was prepared under the conditions described in (II-1) above. In addition, the following steps, which were performed after completion of the PCR amplification, were also carried out in accordance with the conditions and procedures described in (II-1) above:

purification of the prepared PCR amplified product;

production of a cyclic plasmid from the purified PCR amplified product of approximately 6.4 kbp via a ligation reaction;

transformation of TOP10 cell and amplification of the plasmid by culture; and the recovery of the amplified plasmid, and the sequencing of the nucleotide sequence of a protein coding region.

A recombinant expression vector pET101-CpYGFP-Y56W, V194S for the Y56W, V194S modified protein was prepared and was then purified by the aforementioned procedures.

(c) Construction of Recombinant Expression Vector for Y56W, V194S, T136A Modified Protein In order to replace a codon ACG encoding Thr[136] with a codon GCC encoding Ala, as well as the aforementioned substitution of Tyr[56] with Trp and substitution of Val[194] with Ser, a DNA fragment was produced by the PCR method using the primers indicated below. That is to say, as a PCR reverse primer, the following primer, to the complementary nucleotide sequence of which the aforementioned codon substitution had been performed, was used.

For the point mutation of T136A,
used as a reverse primer was
CpYGFP T136A LP (22 mer):

(SEQ ID NO: 27)
5'-CAC GGC GGG ACA CGA CTT CAC G-3',

When translation was performed using the complementary strand thereof, the following replacement of amino acid residues was carried out.

5'-C GTG AAG TCG TGT CCC <u>GCC</u> GTG-3'

(SEQ ID NO: 27)
3'-G CAC TTC AGC ACA GGG <u>CGG</u> CAC-5'

Val Lys Ser Cys Pro Ala Val
                    135

On the other hand, as a forward primer,
CpYGFP UP412 (21 mer):

5'-GAC CTG ATG TTG CCG ATG TCC-3'  (SEQ ID NO: 26)

Asp Lue Met Leu Pro Met Ser
                140 was used, and thus, such a primer comprising a nucleotide sequence corresponding to a partial nucleotide sequence (a portion ranging from nucleotides 412 to 432) comprising a codon GTC encoding Asp[138] at the 5'-terminus thereof was used.

Using the recombinant expression vector pET101-CpYGFP-Y56W, V194S for the Y56W, V194S modified protein as a template, a PCR amplified product with a size of approximately 6.4 kbp that corresponded to the entire length of the aforementioned plasmid was prepared under the conditions described in (II-1) above. In addition, the following steps, which were performed after completion of the PCR amplification, were also carried out in accordance with the conditions and procedures described in (II-1) above:

purification of the prepared PCR amplified product;

production of a cyclic plasmid from the purified PCR amplified product of approximately 6.4 kbp via a ligation reaction;

transformation of TOP10 cell and amplification of the plasmid by culture; and the recovery of the amplified plasmid, and the sequencing of the nucleotide sequence of a protein coding region.

A recombinant expression vector pET101-CpYGFP-Y56W, V194S, T136A for the Y56W, V194S, T136A modified protein was prepared and was then purified by the aforementioned procedures.

After completion of the preparation and purification of the recombinant expression vector pET101-CpYGFP-Y56W for the Y56W modified protein, the recombinant expression vector pET101-CpYGFP-Y56W, V194S for the Y56W, V194S modified protein, and the recombinant expression vector pET101-CpYGFP-Y56W, V194S, T136A for the Y56W, V194S, T136A modified protein, the nucleotide sequence of the mutation-introduced site of each of the above proteins was confirmed by the following procedures.

In order to confirm the nucleotide sequence of a gene encoding each modified protein contained in the purified plasmid vector, using a region encoding such a modified protein contained in the aforementioned plasmid vector as a template, a DNA fragment was amplified by PCR, so as to produce a sample used in sequence analysis.

At that time, PCR primers, namely, a forward primer pET-UP1 (28 mer):

5'-CACCATGACAACCTTCAAAATCGAGTCC-3' (SEQ ID NO: 28)

and a reverse primer SalI-LP1 (35 mer):

(SEQ ID NO: 29)
5'-CTCGTCGACCTACATGTCTCTTGGGGCGCTGTTGA-3', which are disclosed in the pamphlet of International Publication WO 2005/095599, were used to prepare an amplified product with a base length of 673 bp.

The sequence analysis sample prepared from the aforementioned 673-bp DNA fragment was subjected to a commercially available sequence apparatus, ABI PRISM 310 Genetic Analyzer, so that both the sequence from the 5'-terminal side and the sequence from the 3'-terminal side were analyzed.

The results of the sequence analysis from the 5'-terminal side were put together with the results of the sequence analysis from the 3'-terminal side. Thereafter, it was confirmed that site-directed mutagenesis of interest had been introduced into the nucleotide sequence of the region encoding such a modified protein, and that the aforementioned nucleotide sequence did not comprise errors made during the PCR amplification.

(III-2) Recombinant Expression of Modified Proteins

Using the recombinant expression vector pET101-CpYGFP-Y56W for the Y56W modified protein, the recombinant expression vector pET101-CpYGFP-Y56W, V194S for the Y56W, V194S modified protein, and the recombinant expression vector pET101-CpYGFP-Y56W, V194S, T136A for the Y56W, V194S, T136A modified protein, all of which had been prepared and purified by the aforementioned procedures, modified proteins were produced by the following procedures.

First, using the recombinant vector for each modified protein, *Escherichia coli* BL21-CodonPlus™ (DE3)-RIL Competent Cells (manufactured by Staratagene) was transformed. The transformed *Escherichia coli*, into which an expression vector of interest had been introduced, was selected using a drug resistance gene originated from the vector pEP101/D-TOPO.

The thus selected transformed *Escherichia coli* was precultured at 37° C. in a liquid medium, to which an agent, Carbenicillin, had been added, until $OD_{600}$ indicating a cell mass density in the medium reached 0.6. When such $OD_{600}$ reached 0.6, IPTG was added to the medium at the final concentration of 1 mM, and the culture temperature was then decreased. The culture was further continued. That is to say, using IPTG, expression of a gene encoding each modified protein was induced from a promoter originated from the vector pET101/D-TOPO. After completion of the expression induction by IPTG, the cells for the Y56W, V194S modified protein were cultured at 25° C. for 5 hours, and the cells for the Y56W, V194S, T136A modified protein were cultured at 25° C. for 5 hours. After completion of such culture, the culture was terminated, and cells were then collected by centrifugation. The collected cell mass was washed with 20 mM Tris-HCl (pH 8.5), and it was then frozen at −80° C. for storage.

Each of the frozen transformed *Escherichia coli* was thawed, and it was then suspended in 20 mM Tris-HCl (pH 8.0), followed by ultrasonic lysis. After completion of the cell lysis, it was centrifuged at 10,000×g, and a supernatant containing a soluble fraction was fractionated. As a result of SDS-PAGE analysis, a new band of 25 kDa, which corresponded to the molecular weight of the modified protein of interest, was found in the aforementioned supernatant.

Each modified protein contained in the supernatant was separated into a soluble protein from the *Escherichia coli* used as a host and into a recombinant protein in accordance with the procedures for purifying the recombinant CpYGFP disclosed in International Publication WO 2005/095599, using a HiTrap-DEAE column (Amersham Biosciences).

HiTrap-DEAE Column Purification Step:

The supernatant containing each modified protein was subjected to an anion exchange column HiTrap DEAE (manufactured by Amersham Biosciences), and it was eluted under elution conditions (A buffer: 20 mM Tris-HCl, pH 8.5; B buffer: 1 M NaCl in A buffer; linear gradient 0%-20% B buffer (0-200 mM NaCl concentration)).

In both cases of the Y56W, V194S modified protein and the Y56W, V194S, T136A modified protein, a supernatant containing a soluble fraction was injected into the column, and an eluent was then supplied under the aforementioned elution conditions, so as to divide the solution including the washing fraction into fractions of predetermined liquid amounts. Thereafter, the presence or absence of a fluorescent protein was confirmed in each fraction. At that time, an excitation light with a wavelength of 365 nm was applied, and as a result, the presence of a fluorescent protein emitting a blue fluorescence was confirmed.

Separately, it was confirmed that several soluble proteins from the *Escherichia coli* used as a host, which may be recovered in the washing fraction, did not exhibit fluorescent properties. Thus, the confirmed fluorescent protein was a recombinantly expressed modified protein. That is to say, such a modified protein was recovered in <1% B buffer fraction (washing fraction)>.

(III-3) Fluorescent Properties of Recombinant Modified Proteins

With regard to the aforementioned column-purified modified proteins, the fluorescence spectrum and excitation spectrum thereof were measured using a solution sample diluted with 20 mM Tris-HCl (pH 8.5). The fluorescence spectrum was measured at a room temperature (25° C.) using a fluorescence measurement apparatus F-4500 manufactured by HITACHI. On the other hand, the excitation spectrum was measured by monitoring the fluorescence intensity in the maximum peak wavelength of the fluorescence spectrum.

Figure 8:
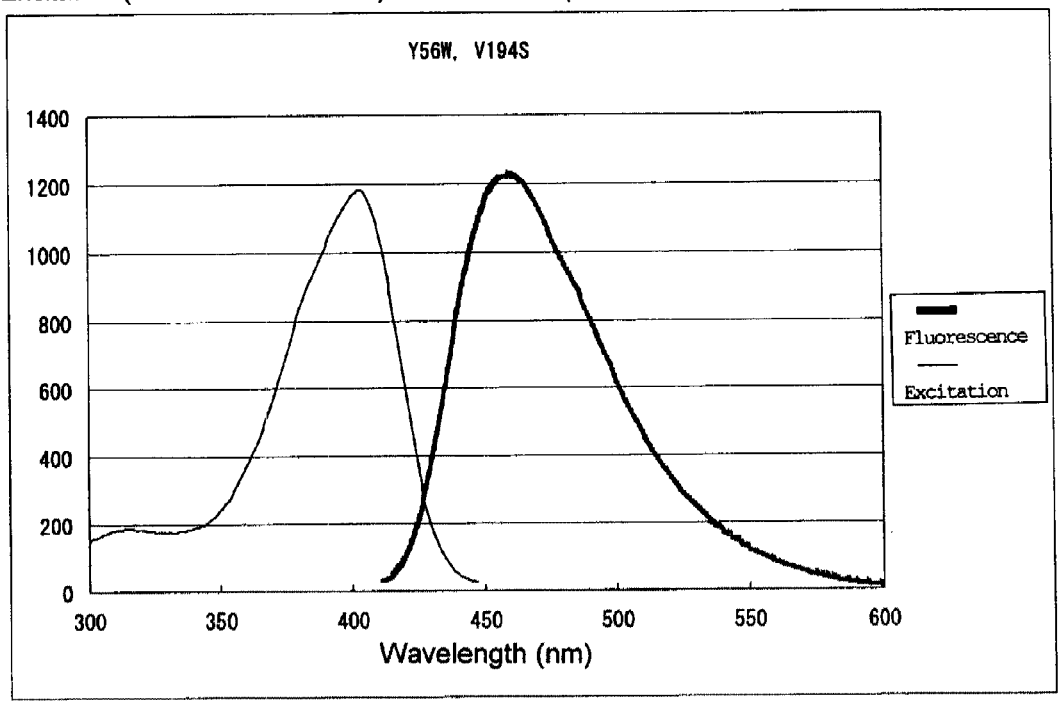
FIG. 8 is a view showing the shapes of the fluorescence/excitation spectra of the modified fluorescent protein, CpYGFP-Y56W, V194S, which is obtained by replacing "GYG" constituting the fluorescent moiety of the GFP-like fluorescent protein from *Chiridius poppei*, CpYGFP, with "GWG"
Figure 9:
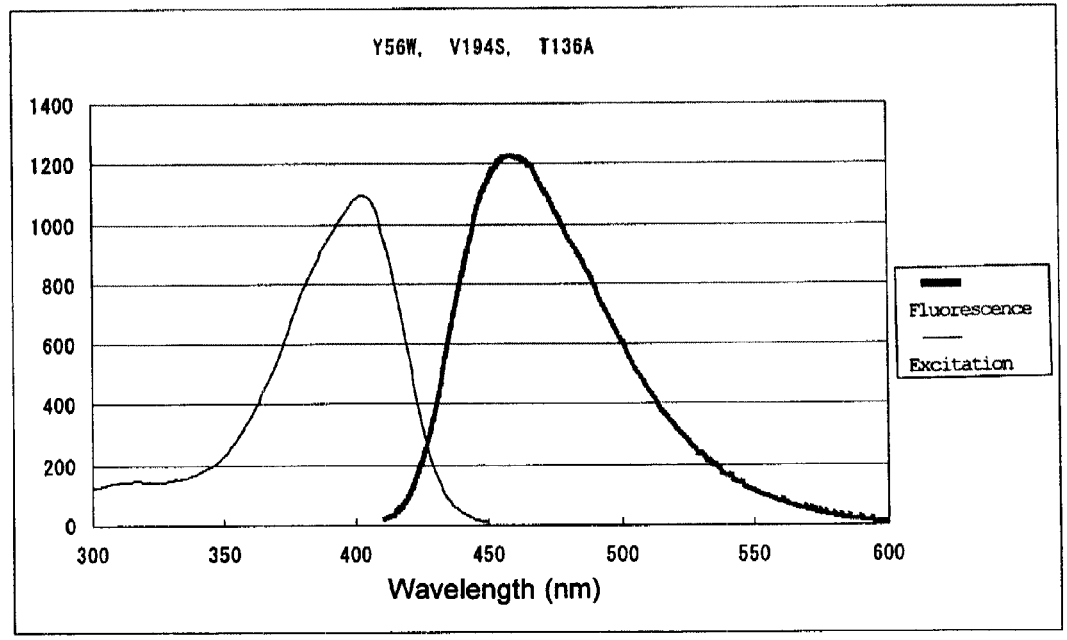
FIG. 9 is a view showing the shapes of the fluorescence/excitation spectra of a modified fluorescent protein, CpYGFP-Y56W, V194S, T136A, which is obtained by replacing "GYG" constituting the fluorescent moiety of the GFP-like fluorescent protein, CpYGFP from *Chiridius poppei*, with "GWG".

The fluorescence spectrum and excitation spectrum of each of the Y56W, V194S modified protein and the Y56WV194S, T136A modified protein are shown in FIGS. 8 and 9. The maximum peak wavelength ($\lambda_{em.MAX}$) on the fluorescence spectrum and the peak wavelength ($\lambda_{ex.peak}$) on the excitation spectrum are shown in Table 6.

TABLE 6

Maximum peak wavelength on fluorescence spectrum and peak wavelength on excitation spectrum

|  | $\lambda_{em.MAX}$ (nm) | $\lambda_{ex.peak}$ (nm) |
|---|---|---|
| Wild type | 517 | 509 |
| Y56W | 460 | 403 |
| Y56W, V194S | 460 | 403 |
| Y56W, V194S, T136A | 459 | 403 |

When compared with the fluorescence spectrum of the wild-type CpYGFP, the fluorescence spectrum of each of the three above types of modified proteins wherein $Tyr^{56}$ was replaced with Trp was blue-shifted. Likewise, the peak on the excitation spectrum was also blue-shifted. These results demonstrated that the fluorescent moiety of the wild-type CpYGFP had a p-hydroxybenzylideneimidazolinone structure, but that the fluorescent moiety of each of the three above types of modified proteins had an indole-3-yl-methylidene-imidazolinone structure as a result of the substitution of Tyr[56] with Trp. Thus, the tendency of such "blue-shift" was similar to that of CFP towards aqGFP.

It is noted that both the fluorescence spectrum and excitation spectrum of CFP show a form obtained by overlapping two fluorescence peaks having only a small energy difference. As a factor for giving such two types of peaks, it is suggested that two fluorescent states (photoexcited states) coexist and that a certain equilibrium state exists between the two fluorescent states (photoexcited states). On the other hand, in the case of the three above types of modified proteins, both the fluorescence spectrum and excitation spectrum apparently have a shape comprising a single peak. That is to say, it is assumed that a single fluorescence state (photoexcited state) is involved therein. Specifically, it is considered that the fluorescence state (photoexcited state) involved in the fluorescence spectrum and excitation spectrum of the three above types of modified proteins corresponds to the fluorescence state (photoexcited state) that gives a peak on a higher energy side among the two fluorescence states (photoexcited states) observed in CFP.

With regard to the fluorescence state (photoexcited state) that gives a peak on a lower energy side among the two fluorescence states (photoexcited states) observed in CFP, it is assumed that, in the indole-3-yl-methylideneimidazolinone structure as a fluorescent moiety, the π-electron conjugated system of the indole ring is connected with the π-electron conjugated system of the imidazolinone ring via an idene-type connecting portion, and that greater delocalization is generated in such an excited state. On the other hand, with regard to the fluorescence state (photoexcited state) that gives a peak on a higher energy side among the two fluorescence states (photoexcited states) observed in CFP, it is assumed that such contribution of the delocalization between the aforementioned two π-electron conjugated systems is small.

When the fluorescence state (photoexcited state) involved in the fluorescence spectrum and excitation spectrum of the three above types of modified proteins is compared with the fluorescence state (photoexcited state) that gives a peak on a higher energy side between the two fluorescence states (photoexcited states) observed in CFP, it gives a peak to a much higher energy side. Thus, it is assumed that contribution of delocalization between the π-electron conjugated system of the indole ring and the π-electron conjugated system of the imidazolinone ring via an idene-type connecting portion is much less, or that the indole ring and the imidazolinone ring do not exist on a single plane and thus it becomes difficult to achieve delocalization via an idene-type connecting portion.

The fluorescence peak wavelength of a modified protein produced by replacing "GYG" forming the fluorescent moiety of CpYGFP with "GWG" is blue-shifted, when compared with the fluorescence peak wavelength of a modified protein produced by replacing "SYG" forming the fluorescent moiety of aqGFP with "SWG." Thus, the blue fluorescence of the modified protein has the comparable level of color tone (blue) with that of BFP.

INDUSTRIAL APPLICABILITY

The fluorescent protein of the present invention, the fluorescence wavelength of which has been changed by modification, can be used as an in vivo fluorescent marker protein capable of expressing in host cells in an in vitro culture system using mammalian cells, as with the wild-type CpYGFP.

SEQUENCE LISTING

<160> NUMBER OF SEQ ID NOS: 32

<210> SEQ ID NO 1
<211> LENGTH: 219
<212> TYPE: PRT
<213> ORGANISM: Chiridius poppei
<220> FEATURE:
<223> OTHER INFORMATION: Monomeric peptide of fluorescent protein CpYGFP
      from Chiridius poppei

<400> SEQUENCE: 1

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser His Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

```
Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
130                 135                 140

Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 2
<211> LENGTH: 660
<212> TYPE: DNA
<213> ORGANISM: Chiridius poppei
<220> FEATURE:
<223> OTHER INFORMATION: ORF sequence encoding a monomeric peptide of
      fluorescent protein CpYGFP from Chiridius poppei

<400> SEQUENCE: 2 atg aca acc ttc aaa atc gag tcc cgg atc cat ggc aac ctc aac ggg     48
Met Thr Thr Phe Lys Ile Glu Ser Arg Ile His Gly Asn Leu Asn Gly
1               5                   10                  15 gag aag ttc gag ttg gtt gga ggt gga gta ggt gag gag ggt cgc ctc     96
Glu Lys Phe Glu Leu Val Gly Gly Gly Val Gly Glu Glu Gly Arg Leu
            20                  25                  30 gag att gag atg aag act aaa gat aaa cca ctg gca ttc tct ccc ttc    144
Glu Ile Glu Met Lys Thr Lys Asp Lys Pro Leu Ala Phe Ser Pro Phe
        35                  40                  45 ctg ctg tcc cac tgc atg ggt tac ggg ttc tac cac ttc gcc agc ttc    192
Leu Leu Ser His Cys Met Gly Tyr Gly Phe Tyr His Phe Ala Ser Phe
    50                  55                  60 cca aag ggg act aag aac atc tat ctt cat gct gca aca aac gga ggt    240
Pro Lys Gly Thr Lys Asn Ile Tyr Leu His Ala Ala Thr Asn Gly Gly
65                  70                  75                  80 tac acc aac acc agg aag gag atc tat gaa gac ggc ggc atc ttg gag    288
Tyr Thr Asn Thr Arg Lys Glu Ile Tyr Glu Asp Gly Gly Ile Leu Glu
                85                  90                  95 gtc aac ttc cgt tac act tac gag ttc aac aag atc atc ggt gac gtc    336
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac    384
Glu Cys Ile Gly His Gly Phe Pro Ser Gln Ser Pro Ile Phe Lys Asp
        115                 120                 125 acg atc gtg aag tcg tgt ccc acg gtg gac ctg atg ttg ccg atg tcc    432
Thr Ile Val Lys Ser Cys Pro Thr Val Asp Leu Met Leu Pro Met Ser
130                 135                 140 ggg aac atc atc gcc agc tcc tac gct aga gcc ttc caa ctg aag gac    480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat    528
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga    576
Pro Ile His Glu Ser Phe Ser Lys Ser Gly Pro Met Phe Thr His Arg
            180                 185                 190
```

```
cgt gtc gag gag act cac acc aag gag aac ctt gcc atg gtg gag tac         624
Arg Val Glu Glu Thr His Thr Lys Glu Asn Leu Ala Met Val Glu Tyr
        195                 200                 205 cag cag gtt ttc aac agc gcc cca aga gac atg tag                         660
Gln Gln Val Phe Asn Ser Ala Pro Arg Asp Met *
    210                 215

<210> SEQ ID NO 3
<211> LENGTH: 782
<212> TYPE: DNA
<213> ORGANISM: Chiridius poppei
<220> FEATURE:
<223> OTHER INFORMATION: cDNA prepared from mRNA encoding a monomeric
      peptide of fluorescent protein CpYGFP from Chiridius poppei

<400> SEQUENCE: 3
agaacactca gtgtatccag ttttccgtcc tactacaaac                              40 atg aca acc ttc aaa atc gag tcc cgg atc cat ggc aac ctc aac ggg          88
Met Thr Thr Phe Lys Ile Glu Ser Arg Ile His Gly Asn Leu Asn Gly
 1               5                  10                  15 gag aag ttc gag ttg gtt gga ggt gga gta ggt gag gag ggt cgc ctc         136
Glu Lys Phe Glu Leu Val Gly Gly Gly Val Gly Glu Glu Gly Arg Leu
             20                  25                  30 gag att gag atg aag act aaa gat aaa cca ctg gca ttc tct ccc ttc         184
Glu Ile Glu Met Lys Thr Lys Asp Lys Pro Leu Ala Phe Ser Pro Phe
         35                  40                  45 ctg ctg tcc cac tgc atg ggt tac ggg ttc tac cac ttc gcc agc ttc         232
Leu Leu Ser His Cys Met Gly Tyr Gly Phe Tyr His Phe Ala Ser Phe
     50                  55                  60 cca aag ggg act aag aac atc tat ctt cat gct gca aca aac gga ggt         280
Pro Lys Gly Thr Lys Asn Ile Tyr Leu His Ala Ala Thr Asn Gly Gly
 65                  70                  75                  80 tac acc aac acc agg aag gag atc tat gaa gac ggc ggc atc ttg gag         328
Tyr Thr Asn Thr Arg Lys Glu Ile Tyr Glu Asp Gly Gly Ile Leu Glu
                 85                  90                  95 gtc aac ttc cgt tac act tac gag ttc aac aag atc atc ggt gac gtc         376
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac         424
Glu Cys Ile Gly His Gly Phe Pro Ser Gln Ser Pro Ile Phe Lys Asp
        115                 120                 125 acg atc gtg aag tcg tgt ccc acg gtg gac ctg atg ttg ccg atg tcc         472
Thr Ile Val Lys Ser Cys Pro Thr Val Asp Leu Met Leu Pro Met Ser
    130                 135                 140 ggg aac atc atc gcc agc tcc tac gct aga gcc ttc caa ctg aag gac         520
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat         568
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga         616
Pro Ile His Glu Ser Phe Ser Lys Ser Gly Pro Met Phe Thr His Arg
            180                 185                 190 cgt gtc gag gag act cac acc aag gag aac ctt gcc atg gtg gag tac         664
Arg Val Glu Glu Thr His Thr Lys Glu Asn Leu Ala Met Val Glu Tyr
        195                 200                 205 cag cag gtt ttc aac agc gcc cca aga gac atg tag                         700
Gln Gln Val Phe Asn Ser Ala Pro Arg Asp Met *
    210                 215 aatgtggaac gaaaccttt ttttctgatta ctttctctgt tgactccaca                   750
```
ttcggaactt gtataaataa gttcagttta aa    782

<210> SEQ ID NO 4
<211> LENGTH: 222
<212> TYPE: PRT
<213> ORGANISM: Pontellina plumata
<220> FEATURE:
<223> OTHER INFORMATION: Monomeric peptide of fluorescent protein
      ppluGFP2 from Pontellina plumata

<400> SEQUENCE: 4

Met Pro Ala Met Lys Ile Glu Cys Arg Ile Thr Gly Thr Leu Asn Gly
1               5                   10                  15

Val Glu Phe Glu Leu Val Gly Gly Gly Glu Gly Thr Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Ile Ala Phe Ala
    210                 215                 220

<210> SEQ ID NO 5
<211> LENGTH: 669
<212> TYPE: DNA
<213> ORGANISM: Artificial Sequence
<220> FEATURE:
<223> OTHER INFORMATION: Human codon-optimized DNA sequence encoding a
      monomeric peptide of fluorescent protein ppluGFP2 from
      Pontellina plumata

<400> SEQUENCE: 5 atg ccc gcc atg aag atc gag tgc cgc atc acc ggc acc ctg aac ggc    48
Met Pro Ala Met Lys Ile Glu Cys Arg Ile Thr Gly Thr Leu Asn Gly
1               5                   10                  15 gtg gag ttc gag ctg gtg ggc ggc gga gag ggc acc ccc gag cag ggc    96
Val Glu Phe Glu Leu Val Gly Gly Gly Glu Gly Thr Pro Glu Gln Gly
            20                  25                  30 cgc atg acc aac aag atg aag agc acc aag ggc gcc ctg acc ttc agc   144
Arg Met Thr Asn Lys Met Lys Ser Thr Lys Gly Ala Leu Thr Phe Ser
        35                  40                  45 ccc tac ctg ctg agc cac gtg atg ggc tac ggc ttc tac cac ttc ggc   192

```
Pro Tyr Leu Leu Ser His Val Met Gly Tyr Gly Phe Tyr His Phe Gly
        50                  55                  60 acc tac ccc agc ggc tac gag aac ccc ttc ctg cac gcc atc aac aac        240
Thr Tyr Pro Ser Gly Tyr Glu Asn Pro Phe Leu His Ala Ile Asn Asn
 65                  70                  75                  80 ggc ggc tac acc aac acc cgc atc gag aag tac gag gac ggc ggc gtg        288
Gly Gly Tyr Thr Asn Thr Arg Ile Glu Lys Tyr Glu Asp Gly Gly Val
                 85                  90                  95 ctg cac gtg agc ttc agc tac cgc tac gag gcc ggc cgc gtg atc ggc        336
Leu His Val Ser Phe Ser Tyr Arg Tyr Glu Ala Gly Arg Val Ile Gly
            100                 105                 110 gac ttc aag gtg gtg ggc acc ggc ttc ccc gag gac agc gtg atc ttc        384
Asp Phe Lys Val Val Gly Thr Gly Phe Pro Glu Asp Ser Val Ile Phe
        115                 120                 125 acc gac aag atc atc cgc agc aac gcc acc gtg gag cac ctg cac ccc        432
Thr Asp Lys Ile Ile Arg Ser Asn Ala Thr Val Glu His Leu His Pro
    130                 135                 140 atg ggc gat aac gtg ctg gtg ggc agc ttc gcc cgc acc ttc agc ctg        480
Met Gly Asp Asn Val Leu Val Gly Ser Phe Ala Arg Thr Phe Ser Leu
145                 150                 155                 160 cgc gac ggc ggc tac tac agc ttc gtg gtg gac agc cac atg cac ttc        528
Arg Asp Gly Gly Tyr Tyr Ser Phe Val Val Asp Ser His Met His Phe
                165                 170                 175 aag agc gcc atc cac ccc agc atc ctg cag aac ggg ggc ccc atg ttc        576
Lys Ser Ala Ile His Pro Ser Ile Leu Gln Asn Gly Gly Pro Met Phe
            180                 185                 190 gcc ttc cgc cgc gtg gag gag ctg cac agc aac acc gag ctg ggc atc        624
Ala Phe Arg Arg Val Glu Glu Leu His Ser Asn Thr Glu Leu Gly Ile
        195                 200                 205 gtg gag tac cag cac gcc ttc aag acc ccg atc gca ttc gcc tga            669
Val Glu Tyr Gln His Ala Phe Lys Thr Pro Ile Ala Phe Ala *
    210                 215                 220

<210> SEQ ID NO 6
<211> LENGTH: 219
<212> TYPE: PRT
<213> ORGANISM: Artificial Sequence
<220> FEATURE:
<223> OTHER INFORMATION: Monomeric peptide of modified fluorescent
      protein CpYGFP-H52F

<400> SEQUENCE: 6

Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Phe Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140
```

```
Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 7
<211> LENGTH: 660
<212> TYPE: DNA
<213> ORGANISM: Artificial Sequence
<220> FEATURE:
<223> OTHER INFORMATION: DNA sequence encoding a monomeric peptide of
      modified fluorescent protein CpYGFP-H52F

<400> SEQUENCE: 7 atg aca acc ttc aaa atc gag tcc cgg atc cat ggc aac ctc aac ggg      48
Met Thr Thr Phe Lys Ile Glu Ser Arg Ile His Gly Asn Leu Asn Gly
 1               5                  10                  15 gag aag ttc gag ttg gtt gga ggt gga gta ggt gag gag ggt cgc ctc      96
Glu Lys Phe Glu Leu Val Gly Gly Gly Val Gly Glu Glu Gly Arg Leu
                20                  25                  30 gag att gag atg aag act aaa gat aaa cca ctg gca ttc tct ccc ttc     144
Glu Ile Glu Met Lys Thr Lys Asp Lys Pro Leu Ala Phe Ser Pro Phe
            35                  40                  45 ctg ctg tcc ttc tgc atg ggt tac ggg ttc tac cac ttc gcc agc ttc     192
Leu Leu Ser Phe Cys Met Gly Tyr Gly Phe Tyr His Phe Ala Ser Phe
        50                  55                  60 cca aag ggg act aag aac atc tat ctt cat gct gca aca aac gga ggt     240
Pro Lys Gly Thr Lys Asn Ile Tyr Leu His Ala Ala Thr Asn Gly Gly
65                  70                  75                  80 tac acc aac acc agg aag gag atc tat gaa gac ggc ggc atc ttg gag     288
Tyr Thr Asn Thr Arg Lys Glu Ile Tyr Glu Asp Gly Gly Ile Leu Glu
                85                  90                  95 gtc aac ttc cgt tac act tac gag ttc aac aag atc atc ggt gac gtc     336
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac     384
Glu Cys Ile Gly His Gly Phe Pro Ser Gln Ser Pro Ile Phe Lys Asp
        115                 120                 125 acg atc gtg aag tcg tgt ccc acg gtg gac ctg atg ttg ccg atg tcc     432
Thr Ile Val Lys Ser Cys Pro Thr Val Asp Leu Met Leu Pro Met Ser
    130                 135                 140 ggg aac atc atc gcc agc tcc tac gct aga gcc ttc caa ctg aag gac     480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat     528
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga     576
Pro Ile His Glu Ser Phe Ser Lys Ser Gly Pro Met Phe Thr His Arg
            180                 185                 190 cgt gtc gag gag act cac acc aag gag aac ctt gcc atg gtg gag tac     624
Arg Val Glu Glu Thr His Thr Lys Glu Asn Leu Ala Met Val Glu Tyr
        195                 200                 205 cag cag gtt ttc aac agc gcc cca aga gac atg tag                     660
```

```
Gln Gln Val Phe Asn Ser Ala Pro Arg Asp Met   *
    210                 215
```

<210> SEQ ID NO 8
<211> LENGTH: 219
<212> TYPE: PRT
<213> ORGANISM: Artificial Sequence
<220> FEATURE:
<223> OTHER INFORMATION: Monomeric peptide of modified fluorescent
      protein CpYGFP-H52T

<400> SEQUENCE: 8

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser Thr Cys Met Gly Tyr Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140

Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215
```

<210> SEQ ID NO 9
<211> LENGTH: 660
<212> TYPE: DNA
<213> ORGANISM: Artificial Sequence
<220> FEATURE:
<223> OTHER INFORMATION: DNA sequence encoding a monomeric peptide of
      modified fluorescent protein CpYGFP-H52T

<400> SEQUENCE: 9

```
atg aca acc ttc aaa atc gag tcc cgg atc cat ggc aac ctc aac ggg      48
Met Thr Thr Phe Lys Ile Glu Ser Arg Ile His Gly Asn Leu Asn Gly
1               5                   10                  15 gag aag ttc gag ttg gtt gga ggt gga gta ggt gag gag ggt cgc ctc      96
Glu Lys Phe Glu Leu Val Gly Gly Gly Val Gly Glu Glu Gly Arg Leu
            20                  25                  30 gag att gag atg aag act aaa gat aaa cca ctg gca ttc tct ccc ttc     144
Glu Ile Glu Met Lys Thr Lys Asp Lys Pro Leu Ala Phe Ser Pro Phe
        35                  40                  45 ctg ctg tcc acc tgc atg ggt tac ggg ttc tac cac ttc gcc agc ttc     192
```

-continued

```
Leu Leu Ser Thr Cys Met Gly Tyr Gly Phe Tyr His Phe Ala Ser Phe
     50                  55                  60 cca aag ggg act aag aac atc tat ctt cat gct gca aca aac gga ggt      240
Pro Lys Gly Thr Lys Asn Ile Tyr Leu His Ala Ala Thr Asn Gly Gly
 65                  70                  75                  80 tac acc aac acc agg aag gag atc tat gaa gac ggc ggc atc ttg gag      288
Tyr Thr Asn Thr Arg Lys Glu Ile Tyr Glu Asp Gly Gly Ile Leu Glu
                 85                  90                  95 gtc aac ttc cgt tac act tac gag ttc aac aag atc atc ggt gac gtc      336
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac      384
Glu Cys Ile Gly His Gly Phe Pro Ser Gln Ser Pro Ile Phe Lys Asp
        115                 120                 125 acg atc gtg aag tcg tgt ccc acg gtg gac ctg atg ttg ccg atg tcc      432
Thr Ile Val Lys Ser Cys Pro Thr Val Asp Leu Met Leu Pro Met Ser
    130                 135                 140 ggg aac atc atc gcc agc tcc tac gct aga gcc ttc caa ctg aag gac      480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat      528
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga      576
Pro Ile His Glu Ser Phe Ser Lys Ser Gly Pro Met Phe Thr His Arg
            180                 185                 190 cgt gtc gag gag act cac acc aag gag aac ctt gcc atg gtg gag tac      624
Arg Val Glu Glu Thr His Thr Lys Glu Asn Leu Ala Met Val Glu Tyr
        195                 200                 205 cag cag gtt ttc aac agc gcc cca aga gac atg tag                      660
Gln Gln Val Phe Asn Ser Ala Pro Arg Asp Met *
    210                 215
```

<210> SEQ ID NO 10
<211> LENGTH: 219
<212> TYPE: PRT
<213> ORGANISM: Artificial Sequence
<220> FEATURE:
<223> OTHER INFORMATION: Monomeric peptide of modified fluorescent
      protein CpYGFP-H52D

<400> SEQUENCE: 10

```
Met Thr Thr Phe Lys Ile Glu Ser Arg Ile His Gly Asn Leu Asn Gly
  1               5                  10                  15

Glu Lys Phe Glu Leu Val Gly Gly Val Gly Glu Glu Gly Arg Leu
                 20                  25                  30

Glu Ile Glu Met Lys Thr Lys Asp Lys Pro Leu Ala Phe Ser Pro Phe
             35                  40                  45

Leu Leu Ser Asp Cys Met Gly Tyr Gly Phe Tyr His Phe Ala Ser Phe
         50                  55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140
```

```
Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 11
<211> LENGTH: 660
<212> TYPE: DNA
<213> ORGANISM: Artificial Sequence
<220> FEATURE:
<223> OTHER INFORMATION: DNA sequence encoding a monomeric peptide of
      modified fluorescent protein CpYGFP-H52D

<400> SEQUENCE: 11 atg aca acc ttc aaa atc gag tcc cgg atc cat ggc aac ctc aac ggg     48
Met Thr Thr Phe Lys Ile Glu Ser Arg Ile His Gly Asn Leu Asn Gly
1               5                   10                  15 gag aag ttc gag ttg gtt gga ggt gga gta ggt gag gag ggt cgc ctc     96
Glu Lys Phe Glu Leu Val Gly Gly Gly Val Gly Glu Glu Gly Arg Leu
            20                  25                  30 gag att gag atg aag act aaa gat aaa cca ctg gca ttc tct ccc ttc    144
Glu Ile Glu Met Lys Thr Lys Asp Lys Pro Leu Ala Phe Ser Pro Phe
        35                  40                  45 ctg ctg tcc gat tgc atg ggt tac ggg ttc tac cac ttc gcc agc ttc    192
Leu Leu Ser Asp Cys Met Gly Tyr Gly Phe Tyr His Phe Ala Ser Phe
50                  55                  60 cca aag ggg act aag aac atc tat ctt cat gct gca aca aac gga ggt    240
Pro Lys Gly Thr Lys Asn Ile Tyr Leu His Ala Ala Thr Asn Gly Gly
65                  70                  75                  80 tac acc aac acc agg aag gag atc tat gaa gac ggc ggc atc ttg gag    288
Tyr Thr Asn Thr Arg Lys Glu Ile Tyr Glu Asp Gly Gly Ile Leu Glu
                85                  90                  95 gtc aac ttc cgt tac act tac gag ttc aac aag atc atc ggt gac gtc    336
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac    384
Glu Cys Ile Gly His Gly Phe Pro Ser Gln Ser Pro Ile Phe Lys Asp
        115                 120                 125 acg atc gtg aag tcg tgt ccc acg gtg gac ctg atg ttg ccg atg tcc    432
Thr Ile Val Lys Ser Cys Pro Thr Val Asp Leu Met Leu Pro Met Ser
    130                 135                 140 ggg aac atc atc gcc agc tcc tac gct aga gcc ttc caa ctg aag gac    480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat    528
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga    576
Pro Ile His Glu Ser Phe Ser Lys Ser Gly Pro Met Phe Thr His Arg
            180                 185                 190 cgt gtc gag gag act cac acc aag gag aac ctt gcc atg gtg gag tac    624
Arg Val Glu Glu Thr His Thr Lys Glu Asn Leu Ala Met Val Glu Tyr
        195                 200                 205 cag cag gtt ttc aac agc gcc cca aga gac atg tag                    660
```

```
Gln Gln Val Phe Asn Ser Ala Pro Arg Asp Met  *
    210                 215
```

<210> SEQ ID NO 12
<211> LENGTH: 219
<212> TYPE: PRT
<213> ORGANISM: Artificial Sequence
<220> FEATURE:
<223> OTHER INFORMATION: Monomeric peptide of modified fluorescent
      protein CpYGFP-Y56W

<400> SEQUENCE: 12

```
Met Thr Thr Phe Lys Ile Glu Ser Arg Ile His Gly Asn Leu Asn Gly
1               5                   10                  15

Glu Lys Phe Glu Leu Val Gly Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser His Cys Met Gly Trp Gly Phe Tyr His Phe Ala Ser Phe
    50                  55                  60

Pro Lys Gly Thr Lys Asn Ile Tyr Leu His Ala Ala Thr Asn Gly Gly
65                  70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140

Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215
```

<210> SEQ ID NO 13
<211> LENGTH: 660
<212> TYPE: DNA
<213> ORGANISM: Artificial Sequence
<220> FEATURE:
<223> OTHER INFORMATION: DNA sequence encoding a monomeric peptide of
      modified fluorescent protein CpYGFP-Y56W

<400> SEQUENCE: 13

```
atg aca acc ttc aaa atc gag tcc cgg atc cat ggc aac ctc aac ggg      48
Met Thr Thr Phe Lys Ile Glu Ser Arg Ile His Gly Asn Leu Asn Gly
1               5                   10                  15 gag aag ttc gag ttg gtt gga ggt gga gta ggt gag gag ggt cgc ctc      96
Glu Lys Phe Glu Leu Val Gly Gly Gly Val Gly Glu Glu Gly Arg Leu
            20                  25                  30 gag att gag atg aag act aaa gat aaa cca ctg gca ttc tct ccc ttc     144
Glu Ile Glu Met Lys Thr Lys Asp Lys Pro Leu Ala Phe Ser Pro Phe
        35                  40                  45 ctg ctg tcc cac tgc atg ggt tgg ggg ttc tac cac ttc gcc agc ttc     192
```

```
                                            -continued

Leu Leu Ser His Cys Met Gly Trp Gly Phe Tyr His Phe Ala Ser Phe
     50                  55                  60 cca aag ggg act aag aac atc tat ctt cat gct gca aca aac gga ggt        240
Pro Lys Gly Thr Lys Asn Ile Tyr Leu His Ala Ala Thr Asn Gly Gly
 65                  70                  75                  80 tac acc aac acc agg aag gag atc tat gaa gac ggc ggc atc ttg gag        288
Tyr Thr Asn Thr Arg Lys Glu Ile Tyr Glu Asp Gly Gly Ile Leu Glu
                 85                  90                  95 gtc aac ttc cgt tac act tac gag ttc aac aag atc atc ggt gac gtc        336
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac        384
Glu Cys Ile Gly His Gly Phe Pro Ser Gln Ser Pro Ile Phe Lys Asp
        115                 120                 125 acg atc gtg aag tcg tgt ccc acg gtg gac ctg atg ttg ccg atg tcc        432
Thr Ile Val Lys Ser Cys Pro Thr Val Asp Leu Met Leu Pro Met Ser
    130                 135                 140 ggg aac atc atc gcc agc tcc tac gct aga gcc ttc caa ctg aag gac        480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat        528
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga        576
Pro Ile His Glu Ser Phe Ser Lys Ser Gly Pro Met Phe Thr His Arg
            180                 185                 190 cgt gtc gag gag act cac acc aag gag aac ctt gcc atg gtg gag tac        624
Arg Val Glu Glu Thr His Thr Lys Glu Asn Leu Ala Met Val Glu Tyr
        195                 200                 205 cag cag gtt ttc aac agc gcc cca aga gac atg tag                        660
Gln Gln Val Phe Asn Ser Ala Pro Arg Asp Met  *
    210                 215

<210> SEQ ID NO 14
<211> LENGTH: 219
<212> TYPE: PRT
<213> ORGANISM: Artificial Sequence
<220> FEATURE:
<223> OTHER INFORMATION: Monomeric peptide of modified fluorescent
      protein CpYGFP-Y56W, V194S

<400> SEQUENCE: 14

Met Thr Thr Phe Lys Ile Glu Ser Arg Ile His Gly Asn Leu Asn Gly
 1               5                  10                  15

Glu Lys Phe Glu Leu Val Gly Gly Val Gly Glu Gly Arg Leu
             20                  25                  30

Glu Ile Glu Met Lys Thr Lys Asp Lys Pro Leu Ala Phe Ser Pro Phe
         35                  40                  45

Leu Leu Ser His Cys Met Gly Trp Gly Phe Tyr His Phe Ala Ser Phe
     50                  55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140
```

```
Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Ser Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 15
<211> LENGTH: 660
<212> TYPE: DNA
<213> ORGANISM: Artificial Sequence
<220> FEATURE:
<223> OTHER INFORMATION: DNA sequence encoding a monomeric peptide of
      modified fluorescent protein CpYGFP-Y56W, V194S

<400> SEQUENCE: 15 atg aca acc ttc aaa atc gag tcc cgg atc cat ggc aac ctc aac ggg       48
Met Thr Thr Phe Lys Ile Glu Ser Arg Ile His Gly Asn Leu Asn Gly
1               5                   10                  15 gag aag ttc gag ttg gtt gga ggt gga gta ggt gag gag ggt cgc ctc       96
Glu Lys Phe Glu Leu Val Gly Gly Gly Val Gly Glu Glu Gly Arg Leu
                20                  25                  30 gag att gag atg aag act aaa gat aaa cca ctg gca ttc tct ccc ttc      144
Glu Ile Glu Met Lys Thr Lys Asp Lys Pro Leu Ala Phe Ser Pro Phe
            35                  40                  45 ctg ctg tcc cac tgc atg ggt tgg ggg ttc tac cac ttc gcc agc ttc      192
Leu Leu Ser His Cys Met Gly Trp Gly Phe Tyr His Phe Ala Ser Phe
        50                  55                  60 cca aag ggg act aag aac atc tat ctt cat gct gca aca aac gga ggt      240
Pro Lys Gly Thr Lys Asn Ile Tyr Leu His Ala Ala Thr Asn Gly Gly
65                  70                  75                  80 tac acc aac acc agg aag gag atc tat gaa gac ggc ggc atc ttg gag      288
Tyr Thr Asn Thr Arg Lys Glu Ile Tyr Glu Asp Gly Gly Ile Leu Glu
                85                  90                  95 gtc aac ttc cgt tac act tac gag ttc aac aag atc atc ggt gac gtc      336
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac      384
Glu Cys Ile Gly His Gly Phe Pro Ser Gln Ser Pro Ile Phe Lys Asp
        115                 120                 125 acg atc gtg aag tcg tgt ccc acg gtg gac ctg atg ttg ccg atg tcc      432
Thr Ile Val Lys Ser Cys Pro Thr Val Asp Leu Met Leu Pro Met Ser
130                 135                 140 ggg aac atc atc gcc agc tcc tac gct aga gcc ttc caa ctg aag gac      480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat      528
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga      576
Pro Ile His Glu Ser Phe Ser Lys Ser Gly Pro Met Phe Thr His Arg
            180                 185                 190 cgt agc gag gag act cac acc aag gag aac ctt gcc atg gtg gag tac      624
Arg Ser Glu Glu Thr His Thr Lys Glu Asn Leu Ala Met Val Glu Tyr
        195                 200                 205 cag cag gtt ttc aac agc gcc cca aga gac atg tag                      660
Gln Gln Val Phe Asn Ser Ala Pro Arg Asp Met
```

```
Gln Gln Val Phe Asn Ser Ala Pro Arg Asp Met *
    210                 215
```

<210> SEQ ID NO 16
<211> LENGTH: 219
<212> TYPE: PRT
<213> ORGANISM: Artificial Sequence
<220> FEATURE:
<223> OTHER INFORMATION: Monomeric peptide of modified fluorescent
      protein CpYGFP-Y56W, V194S, T136A

<400> SEQUENCE: 16

```
Met Thr Thr Phe Lys Ile Glu Ser Arg Ile His Gly Asn Leu Asn Gly
1               5                   10                  15

Glu Lys Phe Glu Leu Val Gly Gly Val Gly Glu Glu Gly Arg Leu
            20                  25                  30

Glu Ile Glu Met Lys Thr Lys Asp Lys Pro Leu Ala Phe Ser Pro Phe
        35                  40                  45

Leu Leu Ser His Cys Met Gly Trp Gly Phe Tyr His Phe Ala Ser Phe
    50                  55                  60

Pro Lys Gly Thr Lys Asn Ile Tyr Leu His Ala Ala Thr Asn Gly Gly
65              70                  75                  80

Tyr Thr Asn Thr Arg Lys Glu Ile Tyr Glu Asp Gly Gly Ile Leu Glu
                85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Ala Val Asp Leu Met Leu Pro Met Ser
    130                 135                 140

Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Ser Glu Glu Thr His Thr Lys Glu Asn Leu Ala Met Val Glu Tyr
        195                 200                 205

Gln Gln Val Phe Asn Ser Ala Pro Arg Asp Met
    210                 215
```

<210> SEQ ID NO 17
<211> LENGTH: 660
<212> TYPE: DNA
<213> ORGANISM: Artificial Sequence
<220> FEATURE:
<223> OTHER INFORMATION: DNA sequence encoding a monomeric peptide of
      modified fluorescent protein CpYGFP-Y56W, V194S, T136A

<400> SEQUENCE: 17

```
atg aca acc ttc aaa atc gag tcc cgg atc cat ggc aac ctc aac ggg    48
Met Thr Thr Phe Lys Ile Glu Ser Arg Ile His Gly Asn Leu Asn Gly
1               5                   10                  15 gag aag ttc gag ttg gtt gga ggt gga gta ggt gag gag ggt cgc ctc    96
Glu Lys Phe Glu Leu Val Gly Gly Gly Val Gly Glu Glu Gly Arg Leu
            20                  25                  30 gag att gag atg aag act aaa gat aaa cca ctg gca ttc tct ccc ttc   144
Glu Ile Glu Met Lys Thr Lys Asp Lys Pro Leu Ala Phe Ser Pro Phe
        35                  40                  45 ctg ctg tcc cac tgc atg ggt tgg ggg ttc tac cac ttc gcc agc ttc   192
```

```
                Leu Leu Ser His Cys Met Gly Trp Gly Phe Tyr His Phe Ala Ser Phe
                     50                  55                  60 cca aag ggg act aag aac atc tat ctt cat gct gca aca aac gga ggt         240
Pro Lys Gly Thr Lys Asn Ile Tyr Leu His Ala Ala Thr Asn Gly Gly
 65                  70                  75                  80 tac acc aac acc agg aag gag atc tat gaa gac ggc ggc atc ttg gag         288
Tyr Thr Asn Thr Arg Lys Glu Ile Tyr Glu Asp Gly Gly Ile Leu Glu
                 85                  90                  95 gtc aac ttc cgt tac act tac gag ttc aac aag atc atc ggt gac gtc         336
Val Asn Phe Arg Tyr Thr Tyr Glu Phe Asn Lys Ile Ile Gly Asp Val
            100                 105                 110 gag tgc att gga cat gga ttc cca agt cag agt ccg atc ttc aag gac         384
Glu Cys Ile Gly His Gly Phe Pro Ser Gln Ser Pro Ile Phe Lys Asp
        115                 120                 125 acg atc gtg aag tcg tgt ccc gcc gtg gac ctg atg ttg ccg atg tcc         432
Thr Ile Val Lys Ser Cys Pro Ala Val Asp Leu Met Leu Pro Met Ser
    130                 135                 140 ggg aac atc atc gcc agc tcc tac gct aga gcc ttc caa ctg aag gac         480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat         528
Gly Ser Phe Tyr Thr Ala Glu Val Lys Asn Asn Ile Asp Phe Lys Asn
                165                 170                 175 cca atc cac gag tcc ttc tcg aag tcg ggg ccc atg ttc acc cac aga         576
Pro Ile His Glu Ser Phe Ser Lys Ser Gly Pro Met Phe Thr His Arg
            180                 185                 190 cgt agc gag gag act cac acc aag gag aac ctt gcc atg gtg gag tac         624
Arg Ser Glu Glu Thr His Thr Lys Glu Asn Leu Ala Met Val Glu Tyr
        195                 200                 205 cag cag gtt ttc aac agc gcc cca aga gac atg tag                         660
Gln Gln Val Phe Asn Ser Ala Pro Arg Asp Met  *
    210                 215

<210> SEQ ID NO 18
<211> LENGTH: 30
<212> TYPE: DNA
<213> ORGANISM: Artificial Sequence
<220> FEATURE:
<223> OTHER INFORMATION: forward PCR primer for site-selected mutation
      to replace codon "CAC" coding His52 with "TTC" coding Phe: CpYGFP
      H52F UP

<400> SEQUENCE: 18 ttc tgc atg ggt tac ggg ttc tac cac ttc                                  30
Phe Cys Met Gly Tyr Gly Phe Tyr His Phe
 1               5                  10

<210> SEQ ID NO 19
<211> LENGTH: 30
<212> TYPE: DNA
<213> ORGANISM: Artificial Sequence
<220> FEATURE:
<223> OTHER INFORMATION: forward PCR primer for site-selected mutation
      to replace codon "CAC" coding His52 with "ACC" coding Thr: CpYGFP
      H52T UP

<400> SEQUENCE: 19 acc tgc atg ggt tac ggg ttc tac cac ttc                                  30
Thr Cys Met Gly Tyr Gly Phe Tyr His Phe
 1               5                  10

<210> SEQ ID NO 20
<211> LENGTH: 30
<212> TYPE: DNA
<213> ORGANISM: Artificial Sequence
```

-continued

```
<220> FEATURE:
<223> OTHER INFORMATION: forward PCR primer for site-selected mutation
      to replace codon "CAC" coding His52 with "GAT" coding Thr: CpYGFP
      H52D UP

<400> SEQUENCE: 20 gat tgc atg ggt tac ggg ttc tac cac ttc                              30
Asp Cys Met Gly Tyr Gly Phe Tyr His Phe
 1               5                  10

<210> SEQ ID NO 21
<211> LENGTH: 28
<212> TYPE: DNA
<213> ORGANISM: Artificial Sequence
<220> FEATURE:
<223> OTHER INFORMATION: Reverse PCR primer for site-selected mutation
      targeted to the codon "CAC" coding His52: CpYGFP LP 153

<400> SEQUENCE: 21
ggacagcagg aagggagaga atgccagt                                       28

<210> SEQ ID NO 22
<211> LENGTH: 27
<212> TYPE: DNA
<213> ORGANISM: Artificial Sequence
<220> FEATURE:
<223> OTHER INFORMATION: forward PCR primer for site-selected mutation
      to replace codon "TAC" coding Tyr56 with "TGG" coding Trp:
      CpYGFP/Y56W UP

<400> SEQUENCE: 22 tgg ggg ttc tac cac ttc gcc agc ttc                                  27
Trp Gly Phe Tyr His Phe Ala Ser Phe
 1               5

<210> SEQ ID NO 23
<211> LENGTH: 31
<212> TYPE: DNA
<213> ORGANISM: Artificial Sequence
<220> FEATURE:
<223> OTHER INFORMATION: Reverse PCR primer for site-selected mutation
      targeted to the codon "TAC" coding Tyr56: CpYGFP LP165

<400> SEQUENCE: 23
acccatgcag tgggacagca ggaagggaga g                                   31

<210> SEQ ID NO 24
<211> LENGTH: 28
<212> TYPE: DNA
<213> ORGANISM: Artificial Sequence
<220> FEATURE:
<223> OTHER INFORMATION: forward PCR primer for site-selected mutation
      targeted to codon "GTC" coding Val194: CpYGFP UP587

<400> SEQUENCE: 24 ag act cac acc aag gag aac ctt gcc at                                28
   Thr His Thr Lys Glu Asn Leu Ala
       1               5

<210> SEQ ID NO 25
<211> LENGTH: 25
<212> TYPE: DNA
<213> ORGANISM: Artificial Sequence
<220> FEATURE:
<223> OTHER INFORMATION: Reverse PCR primer for site-selected mutation
      to replace the codon "GTC" coding Val194 with "AGC" coding Ser:
      CpYGFP V194S LP

<400> SEQUENCE: 25
```

```
cctcgctacg tctgtgggtg aacat                                           25
```

<210> SEQ ID NO 26
<211> LENGTH: 21
<212> TYPE: DNA
<213> ORGANISM: Artificial Sequence
<220> FEATURE:
<223> OTHER INFORMATION: forward PCR primer for site-selected mutation
      targeted to codon "ACG" coding Thr136: CpYGFP UP412

<400> SEQUENCE: 26

```
gac ctg atg ttg ccg atg tcc                                           21
Asp Leu Met Leu Pro Met Ser
 1               5
```

<210> SEQ ID NO 27
<211> LENGTH: 22
<212> TYPE: DNA
<213> ORGANISM: Artificial Sequence
<220> FEATURE:
<223> OTHER INFORMATION: Reverse PCR primer for site-selected mutation
      to replace the codon "ACG" coding Thr136 with "GCC" coding Ala:
      CpYGFP T136A LP

<400> SEQUENCE: 27

```
cacggcggga cacgacttca cg                                              22
```

<210> SEQ ID NO 28
<211> LENGTH: 28
<212> TYPE: DNA
<213> ORGANISM: Artificial Sequence
<220> FEATURE:
<223> OTHER INFORMATION: forward PCR primer for preparation of DNA
      fragment to be used for sequencing the ORF therein: pET-UP1

<400> SEQUENCE: 28

```
caccatgaca accttcaaaa tcgagtcc                                        28
```

<210> SEQ ID NO 29
<211> LENGTH: 35
<212> TYPE: DNA
<213> ORGANISM: Artificial Sequence
<220> FEATURE:
<223> OTHER INFORMATION: reverse PCR primer for preparation of DNA
      fragment to be used for sequencing the ORF therein: Sal I-LP1

<400> SEQUENCE: 29

```
ctcgtcgacc tacatgtctc ttggggcgct gttga                                35
```

<210> SEQ ID NO 30
<211> LENGTH: 660
<212> TYPE: DNA
<213> ORGANISM: Artificial Sequence
<220> FEATURE:
<223> OTHER INFORMATION: DNA sequence encoding a monomeric peptide of
      modified fluorescent protein CpYGFP-H52X
<220> FEATURE:
<221> NAME/KEY: mutation
<222> LOCATION: 154..156
<223> OTHER INFORMATION: wherein n is a, t, g, or c; and wherein Xaa is
      Phe, Tyr, Trp, Ala, Val, Ile, Leu, Gly, Cys, Met, Ser, Thr, Asp,
      Glu, Asn and Gln

<400> SEQUENCE: 30

```
atg aca acc ttc aaa atc gag tcc cgg atc cat ggc aac ctc aac ggg       48
Met Thr Thr Phe Lys Ile Glu Ser Arg Ile His Gly Asn Leu Asn Gly
 1               5                  10                  15 gag aag ttc gag ttg gtt gga ggt gga gta ggt gag gag ggt cgc ctc       96
Glu Lys Phe Glu Leu Val Gly Gly Gly Val Gly Glu Glu Gly Arg Leu
```

```
                    20                  25                  30
gag att gag atg aag act aaa gat aaa cca ctg gca ttc tct ccc ttc          144
Glu Ile Glu Met Lys Thr Lys Asp Lys Pro Leu Ala Phe Ser Pro Phe
         35                  40                  45 ctg ctg tcc nnn tgc atg ggt tac ggg ttc tac cac ttc gcc agc ttc          192
Leu Leu Ser Xaa Cys Met Gly Tyr Gly Phe Tyr His Phe Ala Ser Phe
 50                  55                  60 cca aag ggg act aag aac atc tat ctt cat gct gca aca aac gga ggt          240
Pro Lys Gly Thr Lys Asn Ile Tyr Leu His Ala Ala Thr Asn Gly Gly
 65                  70                  75                  80 tac acc aac acc agg aag gag atc tat gaa gac ggc ggc atc ttg gag          288
Tyr Thr Asn Thr Arg Lys Glu Ile Tyr Glu Asp Gly Gly Ile Leu Glu
             85                  90                  95 gtc aac ttc cgt tac act tac gag ttc aac aag atc atc ggt gac gtc          336
Val Asn Phe Arg Tyr Thr Tyr Glu Phe Asn Lys Ile Ile Gly Asp Val
        100                 105                 110 gag tgc att gga cat gga ttc cca agt cag agt ccg atc ttc aag gac          384
Glu Cys Ile Gly His Gly Phe Pro Ser Gln Ser Pro Ile Phe Lys Asp
            115                 120                 125 acg atc gtg aag tcg tgt ccc acg gtg gac ctg atg ttg ccg atg tcc          432
Thr Ile Val Lys Ser Cys Pro Thr Val Asp Leu Met Leu Pro Met Ser
130                 135                 140 ggg aac atc atc gcc agc tcc tac gct aga gcc ttc caa ctg aag gac          480
Gly Asn Ile Ile Ala Ser Ser Tyr Ala Arg Ala Phe Gln Leu Lys Asp
145                 150                 155                 160 ggc tct ttc tac acg gca gaa gtc aag aac aac ata gac ttc aag aat          528
Gly Ser Phe Tyr Thr Ala Glu Val Lys Asn Asn Ile Asp Phe Lys Asn
            165                 170                 175 cca atc cac gag tcc ttc tcg aag tcg ggg ccc atg ttc acc cac aga          576
Pro Ile His Glu Ser Phe Ser Lys Ser Gly Pro Met Phe Thr His Arg
            180                 185                 190 cgt gtc gag gag act cac acc aag gag aac ctt gcc atg gtg gag tac          624
Arg Val Glu Glu Thr His Thr Lys Glu Asn Leu Ala Met Val Glu Tyr
            195                 200                 205 cag cag gtt ttc aac agc gcc cca aga gac atg tag                          660
Gln Gln Val Phe Asn Ser Ala Pro Arg Asp Met *
            210                 215
```

<210> SEQ ID NO 31
<211> LENGTH: 225
<212> TYPE: PRT
<213> ORGANISM: Artificial Sequence
<220> FEATURE:
<223> OTHER INFORMATION: DsRed fluorescent protein

<400> SEQUENCE: 31

```
Met Arg Ser Ser Lys Asn Val Ile Lys Glu Phe Met Arg Phe Lys Val
  1               5                  10                  15

Arg Met Glu Gly Thr Val Asn Gly His Glu Phe Glu Ile Glu Gly Glu
             20                  25                  30

Gly Glu Gly Arg Pro Tyr Glu Gly His Asn Thr Val Lys Leu Lys Val
         35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
             85                  90                  95

Met Asn Phe Glu Asp Gly Gly Val Val Thr Val Thr Gln Asp Ser Ser
        100                 105                 110
```

```
Leu Gly Asp Gly Cys Phe Ile Tyr Lys Val Lys Phe Ile Gly Val Asn
            115                 120                 125
Phe Pro Ser Asp Gly Pro Val Met Gln Lys Thr Met Gly Trp Glu
130                 135                 140
Ala Ser Thr Glu Arg Leu Tyr Pro Arg Asp Gly Val Leu Lys Gly Glu
145                 150                 155                 160
Ile His Lys Ala Leu Lys Leu Lys Asp Gly Gly His Tyr Leu Val Glu
                165                 170                 175
Phe Lys Ser Ile Tyr Met Ala Lys Lys Pro Val Gln Leu Pro Gly Tyr
                180                 185                 190
Tyr Tyr Val Asp Ser Lys Leu Asp Ile Thr Ser His Asn Glu Asp Tyr
                195                 200                 205
Thr Ile Val Glu Gln Tyr Glu Arg Thr Glu Gly Arg His His Leu Phe
    210                 215                 220
Leu
225
```

<210> SEQ ID NO 32
<211> LENGTH: 238
<212> TYPE: PRT
<213> ORGANISM: Artificial Sequence
<220> FEATURE:
<223> OTHER INFORMATION: aqGFP fluorescent protein

<400> SEQUENCE: 32

```
Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Ser Gly Glu
                20                  25                  30
Gly Glu Gly Asp Ala Thr Tyr Gly Lys Leu Thr Leu Lys Phe Ile Cys
            35                  40                  45
Thr Thr Gly Lys Leu Pro Val Pro Trp Pro Thr Leu Val Thr Thr Phe
    50                  55                  60
Ser Tyr Gly Val Gln Cys Phe Ser Arg Tyr Pro Asp His Met Lys Arg
65                  70                  75                  80
His Asp Phe Phe Lys Ser Ala Met Pro Glu Gly Tyr Val Gln Gln Arg
                85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Leu Glu Tyr Asn
130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
    210                 215                 220
Thr Ala Ala Gly Ile Thr His Gly Met Asp Glu Leu Tyr Lys
225                 230                 235
```

The invention claimed is:

1. A modified fluorescent protein of a GFP-like fluorescent protein from *Chiridius poppei: Chiridius poppei* yellowish-green fluorescent protein (CpYGFP),
    which is characterized in that it is any one of:
    a modified fluorescent protein comprising a full amino acid sequence wherein histidine (His) at the 52nd amino acid position is replaced with one amino acid selected from the aromatic amino acid group consisting of phenylalanine (Phe), tyrosine (Tyr) and tryptophan (Trp) in the full-length amino acid sequence (SEQ ID NO: 1) of the CpYGFP:

```
MTTFKIESRI HGNLNGEKFE LVGGGVGEEG RLEIEMKTKD        60
KPLAFSPFLL SHCMGYGFYH
FASFPKGTKN IYLHAATNGG YTNTRKEIYE DGGILEVNFR       120
YTYEFNKIIG DVECIGHGFP
SQSPIFKDTI VKSCPTVDLM LPMSGNIIAS SYARAFQLKD       180
GSFYTAEVKN NIDFKNPIHE
SFSKSGPMFT HRRVEETHTK ENLAMVEYQQ VFNSAPRDM        219
``` and exhibiting a red shifted fluorescence peak wavelength, when compared with the fluorescence peak wavelength of the CpYGFP;
    a modified fluorescent protein comprising a full amino acid sequence wherein the His at the 52nd amino acid position in the full-length amino acid sequence of the CpYGFP is replaced with one amino acid selected from the amino acid group consisting of alanine (Ala), valine (Val), isoleucine (Ile), leucine (Leu), glycine (Gly), cysteine (Cys), methionine (Met), serine (Ser) and threonine (Thr), and exhibiting a blue shifted fluorescence peak wavelength, when compared with the fluorescence peak wavelength of the CpYGFP; and
    a modified fluorescence protein comprising a full amino acid sequence wherein the His at the 52nd amino acid position in the full-length amino acid sequence of the CpYGFP is replaced with one amino acid selected from the amino acid group consisting of aspartic acid (Asp), asparagine (Asn), glutamic acid (Glu) and glutamine (Gln), and exhibiting a blue shifted fluorescence peak wavelength, when compared with the fluorescence peak wavelength of the CpYGFP.

2. The modified fluorescent protein as claimed in claim 1, which is characterized in that it is a modified fluorescent protein CpYGFP-H52F comprising a full amino acid sequence wherein the His at the 52nd amino acid position in the full-length amino acid (SEQ ID NO: 1) of the CpYGFP is replaced with Phe, and exhibiting a red shifted fluorescence peak wavelength, when compared with the fluorescence peak wavelength of the CpYGFP.

3. The modified fluorescent protein as claimed in claim 1, which is characterized in that it is a modified fluorescent protein CpYGFP-H52T comprising a full amino acid sequence wherein the His at the 52nd amino acid position in the full-length amino acid sequence (SEQ ID NO: 1) of the CpYGFP is replaced with Thr, and exhibiting a blue shifted fluorescence peak wavelength, when compared with the fluorescence peak wavelength of the CpYGFP.

4. The modified fluorescent protein according to claim 1, which is characterized in that it is a modified fluorescent protein CpYGFP-H52D comprising a full amino acid sequence wherein the His at the 52nd amino acid position in the full-length amino acid sequence (SEQ ID NO: 1) of the CpYGFP is replaced with Asp, and exhibiting a blue shifted fluorescence peak wavelength, when compared with the fluorescence peak wavelength of the CpYGFP.

5. A modified fluorescent protein of a GFP-like fluorescent protein from *Chiridius poppei: Chiridius poppei* yellowish-green fluorescent protein (CpYGFP),
    which is characterized in that it is any one of:
    a modified fluorescent protein CpYGFP-Y56W comprising a full amino acid sequence wherein tyrosine (Tyr) at the 56th amino acid position is replaced with tryptophan (Trp) in the full-length amino acid sequence (SEQ ID NO: 1) of the CpYGFP:

```
MTTFKIESRI HGNLNGEKFE LVGGGVGEEG RLEIEMKTKD        60
KPLAFSPFLL SHCMGYGFYH
FASFPKGTKN IYLHAATNGG YTNTRKEIYE DGGILEVNFR       120
YTYEFNKIIG DVECIGHGFP
SQSPIFKDTI VKSCPTVDLM LPMSGNIIAS SYARAFQLKD       180
GSFYTAEVKN NIDFKNPIHE
SFSKSGPMFT HRRVEETHTK ENLAMVEYQQ VFNSAPRDM        219
``` and exhibiting a blue shifted fluorescence peak wavelength of 460 nm or shorter, when compared with the fluorescence peak wavelength of the CpYGFP;
    a modified fluorescent protein CpYGFP-Y56W, V194S comprising a full amino acid sequence wherein the Tyr at the 56th amino acid position is replaced with Trp, and valine (Val) at the 194th amino acid position is further replaced with serine (Ser) in the full-length amino acid sequence of the CpYGFP, and exhibiting a blue shifted fluorescence peak wavelength of 460 nm or shorter, when compared with the fluorescence peak wavelength of the CpYGFP; and
    a modified fluorescence protein CpYGFP-Y56W, V194S, T136A comprising a full amino acid sequence wherein the amino acid at position 56 Tyr is replaced with Trp, the Val at the 194th amino acid position is replaced with Ser, and threonine (Thr) at the 136th amino acid position is further replaced with alanine (Ala) in the full-length amino acid sequence of the CpYGFP, and exhibiting a blue shifted fluorescence peak wavelength of 460 nm or shorter, when compared with the fluorescence peak wavelength of the CpYGFP.

* * * * *

UNITED STATES PATENT AND TRADEMARK OFFICE
CERTIFICATE OF CORRECTION

| | |
|---|---|
| PATENT NO. | : 8,278,120 B2 |
| APPLICATION NO. | : 12/162460 |
| DATED | : October 2, 2012 |
| INVENTOR(S) | : Suto |

It is certified that error appears in the above-identified patent and that said Letters Patent is hereby corrected as shown below:

In the Specification

Column 1, Line 54: Delete "can "β"." and insert -- "β can". --

Column 2, Line 5: Delete "[Chemcial formula 1]" and insert -- [Chemical formula 1] --

Column 9, Line 28: Delete "a helix (β$_2$-helix)" and insert -- α helix (α$_2$-helix) --

Column 13-14, Line 14: Delete "MTTFKTESRI" and insert -- MTTFKIESRI --

Column 13-14, Line 59: Delete "FA; 222" and insert -- FA 222; --

Column 18, Line 15: Delete "n-electron" and insert -- π-electron --

Column 19, Line 61: Delete "n-electron" and insert -- π-electron --

Column 20, Line 5: Delete "n-electron" and insert -- π-electron --

Column 20, Line 18-31: Delete "In the case........progress." and insert the same on Col. 20, Line 17, after "aqGFP.", as a continuation of the same paragraph.

Column 24, Line 33: Delete "EVRQGEN." and insert -- EVR ΩGEN. --

Column 29, Line 36: Delete ""βscan"" and insert -- "β can" --

Column 30, Line 39: Delete "[Chemcial formula 9]" and insert -- [Chemical formula 9] --

Column 36, Line 4: Delete "( $\lambda_{em.max}$)" and insert -- ($\lambda_{em.MAX}$) --

Column 36, Line 56: Delete "Phe" and insert -- Phe$^{52}$ --

Signed and Sealed this
Twenty-first Day of October, 2014

Michelle K. Lee
*Deputy Director of the United States Patent and Trademark Office*